US012680084B2

(12) United States Patent   (10) Patent No.: US 12,680,084 B2
Wu et al.                        (45) Date of Patent: Jul. 14, 2026

(54) MODULATING TLR/NF-KB AND P53 SIGNALING PATHWAYS TO ENHANCE INTERSPECIES CHIMERISM BETWEEN EVOLUTIONARYILY DISTANT SPECIES

(71) Applicant: THE BOARD OF REGENTS OF THE UNIVERSITY OF TEXAS SYSTEM, Austin, TX (US)

(72) Inventors: Jun Wu, Farmers Branch, TX (US); Canbin Zheng, Dallas, TX (US); Yingying Hu, Dallas, TX (US)

(73) Assignee: THE BOARD OF REGENTS OF THE UNIVERSITY OF TEXAS SYSTEM, Austin, TX (US)

( * ) Notice: Subject to any disclaimer, the term of this patent is extended or adjusted under 35 U.S.C. 154(b) by 650 days.

(21) Appl. No.: 17/793,150

(22) PCT Filed: Jan. 21, 2021

(86) PCT No.: PCT/US2021/014358
§ 371 (c)(1),
(2) Date: Jul. 15, 2022

(87) PCT Pub. No.: WO2021/150712
PCT Pub. Date: Jul. 29, 2021

(65) Prior Publication Data
US 2023/0073534 A1      Mar. 9, 2023

Related U.S. Application Data

(60) Provisional application No. 62/963,801, filed on Jan. 21, 2020.

(51) Int. Cl.
*C12N 5/26*        (2006.01)
*C12N 5/073*       (2010.01)
(52) U.S. Cl.
CPC .......... *C12N 5/166* (2013.01); *C12N 5/0604* (2013.01); *A01K 2207/12* (2013.01); *A01K 2207/15* (2013.01); *C12N 2501/60* (2013.01)
(58) Field of Classification Search
CPC .............................. C12N 5/166; C12N 5/0604
See application file for complete search history.

(56) References Cited

U.S. PATENT DOCUMENTS

2016/0029604 A1* 2/2016 Fahrenkrug ........ A01K 67/0275
                                              800/15
2017/0283777 A1  10/2017 Izpisua et al.
2019/0254266 A1*  8/2019 Fahrenkrug ........ C07K 14/7155

FOREIGN PATENT DOCUMENTS

WO      WO-0041561 A1 *  7/2000   ......... A01K 67/0276
WO    WO-2015168125 A1 * 11/2015   ......... A01K 67/0275
WO    WO-2017075261 A1 *  5/2017   ........... A01K 67/027

OTHER PUBLICATIONS

WO_0041561_A1_I translation pp. 1-29 (Year: 2004).*
Sarmah et al (Frontiers in Cell and Developmental Biology 2023 11:1070560. doi: 10.3389/fcell.2023.1070560; pp. 1-16) (Year: 2023).*
Blake and Steer (Hepatic Medicine: Evidence and Research 2024:16 11-29) (Year: 2024).*
Amoyel et al, "Cell competition: how to eliminate your neighbours", Development, vol. 141, pp. 988-1000, (2014).
Bayerl et al, "Tripartite Inhibition of SRC-WNT-PKC Signalling Consolidates Human Naïve Pluripotency", bioRxiv, 74 pages, May 24, 2020.
Bedzhov et al, "In vitro culture of mouse blastocysts beyond the implantation stages", Nature Protocols, vol. 9, No. 12, pp. 2732-2739, Oct. 30, 2014.
Bogliotti et al, "Efficient derivation of stable primed pluripotent embryonic stem cells from bovine blastocysts", PNAS, 6 pages, Jan. 3, 2018.
Boroviak et al, "The ability of inner-cell-mass to self-renew as embryonic stem cells is acquired following epiblast specification", nature cell biology, vol. 16, No. 6, pp. 513-525.
Bowling et al, "P53 and mTOR signalling determine fitness selection through cell competition during early mouse embryonic development", Nature Communications, vol. 9, No. 1763, 12 pages, (2018).
Bredenkamp et al, "The Cell-Surface Marker Sushi Containing Domain 2 Facilitates Establishment of Human Naïve Pluripotent Stem Cells", Stem Cell Reports, vol. 12, pp. 1212-1222, Jun. 11, 2019.
Claveria et al, "Myc-driven enddogenous cell competition in the early mammalian embryo", Nature, vol. 500, pp. 39-43, Aug. 1, 2013.
Claveria et al, "Cell Competition: Mechanisms and Physiological Roles", Annu. Rev. Cell Dev. Biol., vol. 32, pp. 411-439, Aug. 8, 2016.
Coghill et al, "Effects of microfluidic channel geometry on leukocyte rolling assays", Biomed Microdevices, vol. 15, pp. 183-193, Oct. 12, 2012.
Das et al, "Generation of human endothelium in pig embryos deficient in ETV2", nature biotechnology, vol. 38, pp. 297-302, Mar. 2020.
Dejosez et al, "Safeguards for Cell Cooperation in Mouse Embryogenesis Shown by Genome-Wide Cheater Screen", Science, vol. 341, pp. 1511-1514, Sep. 27, 2013.
Fu et al, "Domesticated cynomolgus monkey embryonic stem cells allow the generation of neonatal interspecies chimeric pigs", Protein Cell, vol. 11, No. 2, pp. 97-107, Aug. 6, 2019.
Gafni et al, "Derivation of novel human ground state naïve pluripotent stem cells", Nature, vol. 504, pp. 282-286, Dec. 12, 2013.

(Continued)

*Primary Examiner* — Marcia S Noble
(74) *Attorney, Agent, or Firm* — DLA Piper LLP US

(57)          ABSTRACT

Disclosed herein are chimeric blastocysts, such as chimeric blastocysts derived from a host blastocyst from a first mammalian species and having donor pluripotent stem cells from a second mammalian species, wherein the donor pluripotent stem cells have reduced expression or reduced biological activity of one or more proteins in the TLR/NF-kB signaling pathway or the p53 pathway. Methods of preparing chimeric blastocysts and methods of obtaining mammalian organs and tissues are also provided.

4 Claims, 35 Drawing Sheets

Specification includes a Sequence Listing.

(56)          References Cited

OTHER PUBLICATIONS

Godar et al, "Growth-Inhibitory and tumor-Suppressive Functions of p53 Depend on Its Repression of CD44 Expression", Cell, vol. 134, pp. 62-73, Jul. 11, 2008.

Goto et al, "Generation of pluripotent stem cell-derived mouse kidneys in Sall1-targeted anephric rats", nature communications, vol. 10, No. 451, 9 pages, (2019).

Guo et al, "Epigenetic resetting of human pluripotency", Development, vol. 144, pp. 2748-2763, Jun. 9, 2017.

Hackett et al, "Regulatory Principles of Pluripotency: From the Ground State Up", Cell Stem Cell, vol. 15, pp. 416-430, Oct. 2, 2014.

Hasimoto et al, "Epiblast Formation by TEAD-YAP-Dependent Expression of Pluipotency Factors and Competitive Elimination of Unspecified Cells", Developmental Cell, vol. 50, pp. 139-154, Jul. 22, 2019.

Honda et al, "Flexible adaptation of male germ cells from female iPSCs of endangered Tokudaia osimensis", Sci. Adv., vol. 3, No. e1602179, 9 pages, May 12, 2017.

Hu et al, "Transient inhibition of mTOR in human pluripotent stem cells enables robust formation of mouse-human chimeric embryos", Sci. Adv., vol. 6, No. eaaz0298, 16 pages, May 13, 2020.

Huang et al, "BMI1 enables interspecies chimerism with human pluripotent stem cells", nature communications, vol. 9, No. 4649, 11 pages, (2018).

Isotani et al, "Formation of a thymus from rat ES cells in xenogeneic nude mouse ↔rat ES chimeras", Genes to Cells, vol. 16, pp. 397-405, (2011).

Kim et al, "HISAT: a fast spliced aligner with low memory requirements", Nat Methods, vol. 12, No. 4, pp. 357-360, Apr. 1, 2016.

Kobayashi et al, "Generation of Rat Pancreas in Mouse by Interspecific Blastocyst Injection of Pluripotent Stem Cells", Cell, vol. 142, pp. 787-799, Sep. 3, 2010.

Kojima et al, The Transcriptional and Functional Properties of Mouse Epiblast Stem Cells Resemble the Anterior Primitive Streak:, Cell Stem Cell, vol. 14, pp. 107-120, Jan. 2, 2014.

Li et al, "Germline Competent Embryonic Stem Cells Derived from Rat Blastocysts", Cell, vol. 135, pp. 1299-1310, Dec. 26, 2008.

Love et al, "Moderated estimation of fold change and dispersion for RNA-seq data with DESeq2", Genome Biology, vol. 15, No. 550, 21 pages, (2014).

Martins et al, "Cell competition is a tumour suppressor mechanism in the thymus", Nature, vol. 000, 18 pages, (2014).

Meyer et al, "An ancient defense system eliminates unfit cells from developing tissues during cell competition", Science, vol. 346, No. 6214, pp. 1258236-1-1258236-8, Dec. 5, 2014.

Mitalipov et al, "Isolation and Characterization of Novel Rhesus Monkey Embryonic Stem Cell Lines", Stem Cells, ol. 24, pp. 2177-2186, (2006).

Morata et al, "Minutes: Mutants of Drosophila Autonomously Affecting Cell Division Rate", Developmental Biology, vol. 42, pp. 211-221, Oct. 1, 1974.

Nelson et al, "Manipulation of Cell-Cell Adhesion Using Bowtie-Shaped Microwells", Methods in Molecular Biology, vol. 370, 10 pages, (2007).

Nichols et al, "Naïve and Primed Puripotent States", Cell Stem Cell, vol. 4, pp. 487-492, Jun. 5, 2009.

Pertea et al, "StringTie enables improved reconstruction of a transcriptome from RNA-seq reads", nature biotechnology, vol. 33, No. 3, pp. 290-295, Mar. 2015.

Sancho et al, "Competitive Interactions Eliminate Unfit Embryonic Stem Cells at the Onset of Differentiation", Developmental Cell, vol. 26, pp. 19-30, Jul. 15, 2013.

Shakiba et al, "Cell competition during reprogramming gives rise to dominant clones", Science, vol. 365, No. 354, 11 pages, Apr. 26, 2019.

Theunissen et al, "Systematic Identification of Culture Conditions for Induction and Maintenance of Naïve Human Pluripotency", Cell Stem Cell, vol. 15, pp. 1-17, Oct. 2, 2014.

Theunissen et al, "Molecular Criteria for Defining the Naïve Human Pluripotent State", Cell Stem Cell, vol. 19, pp. 502-515, Oct. 6, 2016.

Wagstaff et al, "Mechanical cell competition kills cells via induction of lethal p53 levels", nature communications, vol. 7, No. 11373, 14 pages, Apr. 25, 2016.

Wang et al, "Human embryonic stem cells contribute to embryonic and extraebryonic lineages in mouse embryos upon inhibition of apoptosis", Cell Research, vol. 28, pp. 126-129, (2018).

Weinberger et al, "Dynamic stem cell states: naïve to primed pluripotency in rodents and humans", bioRXIV, 34 pages, Dec. 12, 2015.

Wu et al, "An alternative pluripotent state confers interspecies chimeric competency", Nature, vol. 521, pp. 316-321, May 21, 2015.

Wu et al, "Dynamic Pluripotent Stem Cell States and Their Applications", Cell Stem Cell, vol. 17, pp. 509-525, Nov. 5, 2015.

Wu et al, "Interspecies Chimerism with Mammalian Pluripotent Stem Cells", Cell, vol. 168, pp. 473-486, Jan. 26, 2017.

Xiang et al, "Extensive contribution of embryonic stem cells to the development of an evolutionary divergent host", Human Molecular Genetics, vol. 17, No. 1, pp. 27-37, Sep. 21, 2007.

Yamaguchi et al, "Interspecies organogenesis generates autologous functional islets", Nature, vol. 542, pp. 191-195, Feb. 9, 2017.

Yang et al, "Derivation of Pluripotent Stem Cells with In Vivo Embryonic and Extraembryonic Potency", Cell, vol. 169, pp. 243-257, Apr. 6, 2017.

Zhang et al, "30 years of NF-κB: a blossoming of relevance to human pathobiology", Cell, vol. 168, No. 1-2, pp. 37-57, Jan. 12, 2017.

International Search Report and Written Opinion of the International Searching Authority issued in International Application No. PCT/US2021/014358, 10 pages, dated Apr. 29, 2021.

* cited by examiner e cont.

f cont.

c

Day 1 Co-URGs d

Day 2 Co-URGs e

Day 3 Co-URGs

FIG. 11

MODULATING TLR/NF-KB AND P53 SIGNALING PATHWAYS TO ENHANCE INTERSPECIES CHIMERISM BETWEEN EVOLUTIONARYILY DISTANT SPECIES

PRIORITY

This application is a 371 National Stage of International Application No. PCT/US2021/014358, filed Jan. 21, 2021, which claims the benefit of U.S. provisional Patent Application Ser. No. 62/963,801 filed Jan. 21, 2020, the disclosures of which are incorporated by reference herein in their entireties.

REFERENCE TO AN ELECTRONIC SEQUENCE LISTING

The contents of the electronic sequence listing (426871-000181 Sequence Listing_ST25.txt; Size: 10.531 bytes; and Date of Creation: Feb. 28, 2021) is herein incorporated by reference in its entirety.

TECHNICAL FIELD

The present disclosure relates generally to interspecies chimeras from evolutionarily distant species. Compositions and methods for the preparation of interspecies chimeras and mammalian organs and tissues are provided.

BACKGROUND

Shortage of human organs for transplantation is one of the largest unmet medical needs. Human pluripotent stem cells (PSCs) offer a potential unlimited source of donor organs. Despite years of research, however, it remains infeasible to generate organs from PSCs in vitro.

To overcome this barrier, an in vivo approach known as interspecies blastocyst complementation, based on the generation of interspecies chimeras, has been developed to enable the formation of an organ from one species inside another species, which raises an intriguing possibility to produce human organs in animals. An important factor for interspecies blastocyst complementation to be successful is the ability of donor PSCs to efficiently contribute to chimera formation in the host species. Rat and mouse PSCs can efficiently contribute to interspecies chimera formation in mouse and rat, respectively, which has enabled the generation of rat pancreas, fetal heart, eye and thymus in mouse, and mouse pancreas in rat via interspecies blastocyst complementation. However, extensive chimerism between evolutionarily more distant species, such as between human and mouse or between human and pig, has not been achieved. For example, human PSCs contribute inefficiently to chimera formation in early post-implantation mice (E9.5-E10.5) and pig (E21-E28) embryos, suggesting elimination of human cells during early development. Loss of chimerism prior to the onset of organogenesis precludes successful complementation as no available donor cells remain to occupy the genetically emptied host organ niche. These results may reflect more than 90 million-year evolutionary distances among primates, rodents, and ungulates, in contrast to the approximately 21 million-year evolutionary distance between mouse and rat, indicating that a xenogeneic barrier exists between evolutionarily distant species during early development.

Successful establishment of chimerism between species that are more distant in evolution would allow for the generation of human organs and tissues for transplantation in large livestock species, for example pig, sheep, goat and cow. Thus, there exists a need for improving interspecies chimerism between species that are relatively distant in evolution.

SUMMARY OF THE INVENTION

Provided herein are chimeric blastocysts that can comprise: (i) a host blastocyst from a first mammalian species; and (ii) donor pluripotent stem cells from a second mammalian species, wherein the donor pluripotent stem cells have reduced expression or reduced biological activity of one or more proteins in the TLR/NF-kB signaling pathway or the p53 pathway. A host blastocyst can be an organogenesis disabled blastocyst. The donor pluripotent stem cells can comprise induced pluripotent stem cells and embryonic stem cells. Pluripotent stem cells are cells that can maintain an undifferentiated state indefinitely, and can differentiate into most, if not all, cells of the body. A protein in the TLR/NF-kB signaling pathway or the p53 pathway can be, for example, IL-1R1, TLR1, TLR2, TLR3, TLR4, TLR5, TLR6, TLR7, TLR8, TLR9, TLR10, TIRAP, TRAM, MAL, SARM, MYD88, IRAK1, IRAK4, TRAF6, TAK1, TAB1, TAB2, TAB3, IKK1, IKK2, NEMO, IkBa, TRIF, RIP1, TRAF3, TBK1, IKKi, IRF3, P65, P50, TP53, or combinations thereof. The first, host mammalian species and the second, donor mammalian species can be different species. The first mammalian species can be a non-primate species. The first mammalian species can be a species of the order Artiodactyla, the order Carnivora, the order Lagomorpha, the order Perissodactyla, or the order Rodentia. The first mammalian species can be a rodent or an ungulate. The ungulate can be a species of the family Suidae. The second mammalian species can be a primate.

Another embodiment provides methods of preparing a chimeric blastocyst. The method can comprise injecting a host blastocyst from a first mammalian species with donor pluripotent stem cells from a second mammalian species, wherein the donor pluripotent stem cells have reduced expression or reduced biological activity of one or more proteins in the TLR/NF-KB signaling pathway or the p53 pathway. The host blastocyst can be an organogenesis disabled blastocyst. The protein in the TLR/NF-kB pathway or the p53 pathway can be, for example, IL-1R1, TLR1, TLR2, TLR3, TLR4, TLR5, TLR6, TLR7, TLR8, TLR9, TLR10, TIRAP, TRAM, MAL, SARM, MYD88, IRAK1, IRAK4, TRAF6, TAK1, TAB1, TAB2, TAB3, IKK1, IKK2, NEMO, IkBa, TRIF, RIP1, TRAF3, TBK1, IKKi, IRF3, P65, P50, TP53, or combinations thereof. The donor pluripotent stem cells can comprise induced pluripotent stem cells or embryonic stem cells. The first mammalian species and the second mammalian species can be different species. The first mammalian species can be a non-primate species. The first mammalian species can be a species of the order Artiodactyla, the order Carnivora, the order Lagomorpha, the order Perissodactyla, or the order Rodentia. The first mammalian species can be a rodent or an ungulate. The ungulate can be a species of the family Suidae. A second mammalian species can be a primate.

Yet another embodiment provides methods of obtaining a mammalian organ or tissue The methods can comprise (i) injecting a host organogenesis disabled blastocyst from a first mammalian species with donor pluripotent stem cells from a second mammalian species to form a chimeric blastocyst, wherein the donor pluripotent stem cells have reduced expression or reduced biological activity of one or more proteins in the TLR/NF-kB signaling pathway or the p53 pathway. The chimeric blastocyst can be implanted into a pseudo-pregnant mammal. A chimeric embryo, fetus, or mammal can be obtained comprising the mammalian organ or tissue. The host blastocyst can be an organogenesis disabled blastocyst. The protein can be selected from IL-1R1, TLR1, TLR2, TLR3, TLR4, TLR5, TLR6, TLR7, TLR8, TLR9, TLR10, TIRAP, TRAM, MAL, SARM, MYD88, IRAK1, IRAK4, TRAF6, TAK1, TAB1, TAB2, TAB3, IKK1, IKK2, NEMO, IkBa, TRIF, RIP1, TRAF3, TBK1, IKKi, IRF3, P65, P50, TP53, or combinations thereof. The donor pluripotent stem cells can comprise induced pluripotent stem cells or embryonic stem cells. The first mammalian species and the second mammalian species can be different species. The first mammalian species can be a non-primate species. The first mammalian species can be a species of the order Artiodactyla, the order Carnivora, the order Lagomorpha, the order Perissodactyla, or the order Rodentia. The first mammalian species is a rodent or an ungulate. The ungulate can be a species of the family Suidae. The second mammalian species can be a primate.

Provided herein are compositions and methods for providing donor pluripotent stem cells that can overcome the xenogeneic barrier for interspecies chimerism between evolutionarily distant mammalian species.

Figure 6:
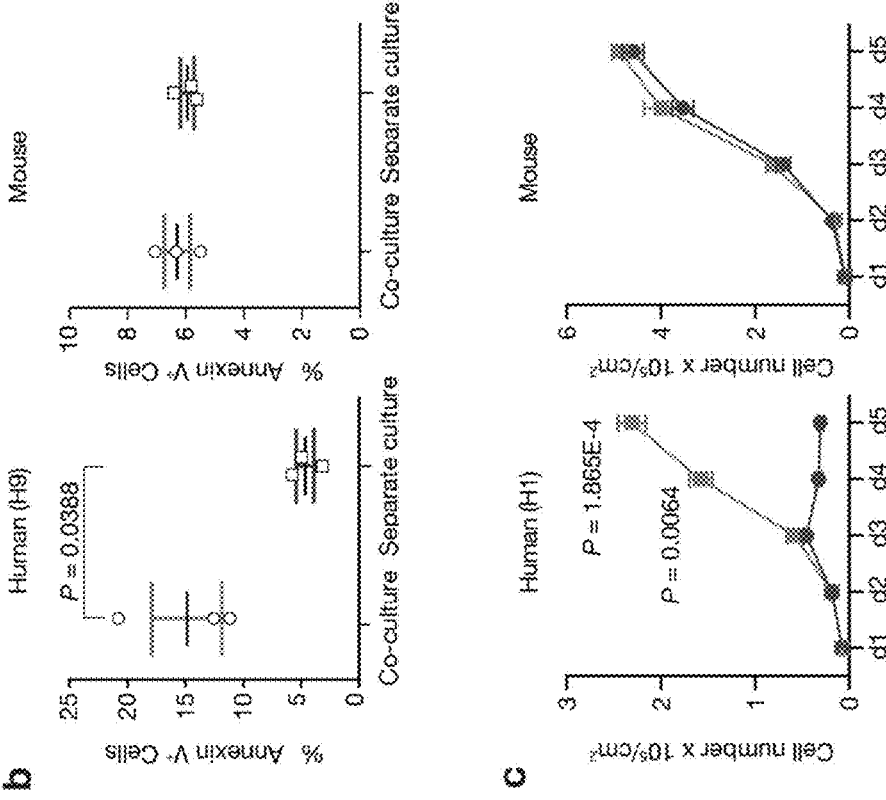
Figure 6:
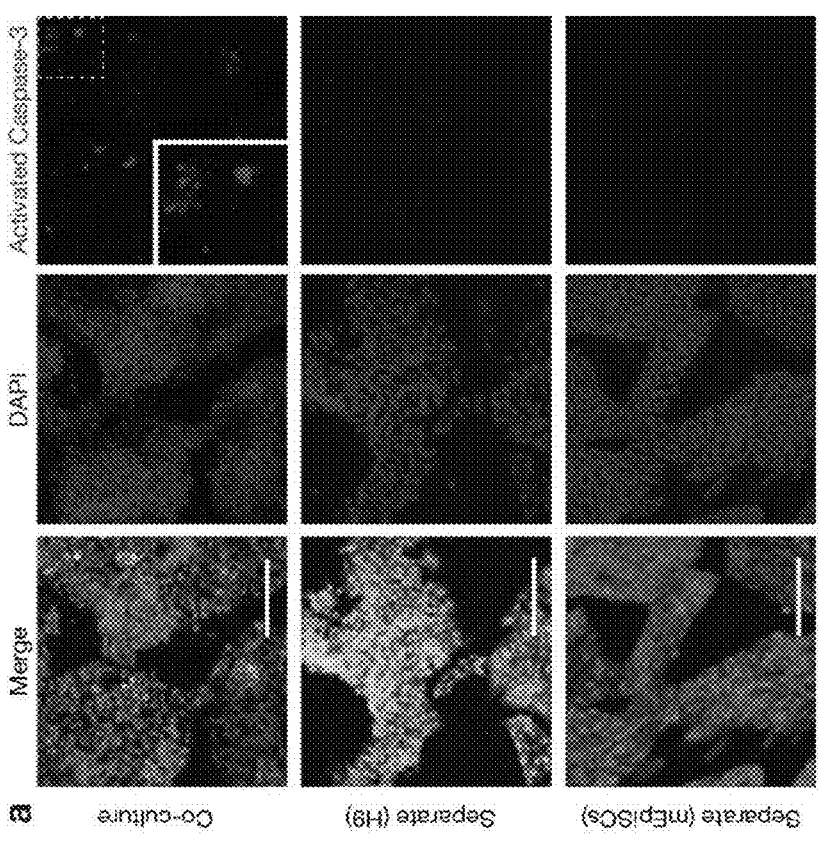
Figure 6:
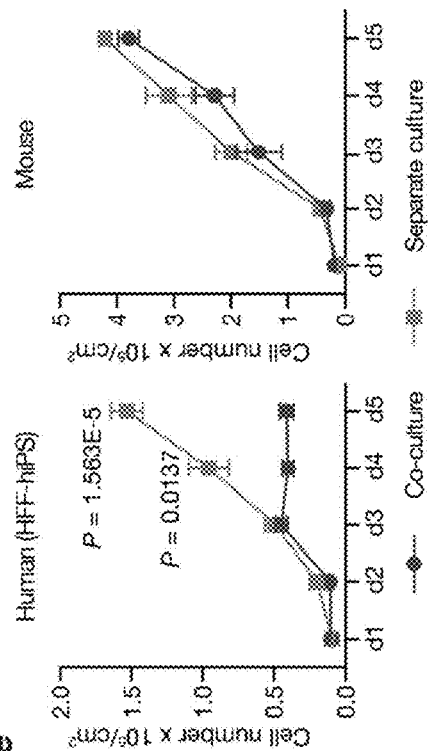
Figure 6:
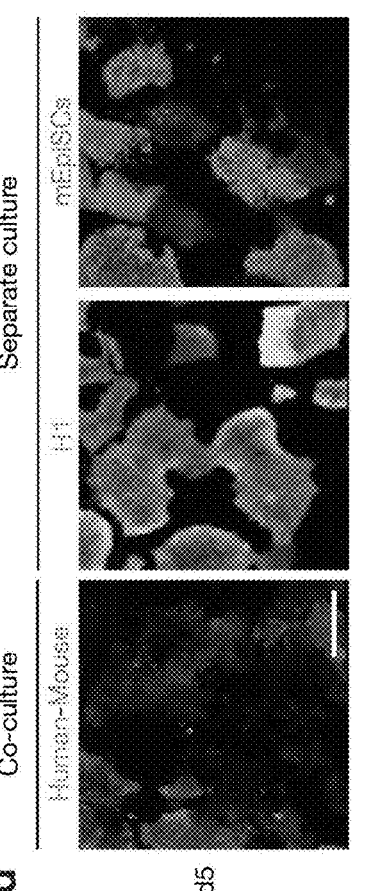
Figure 6:
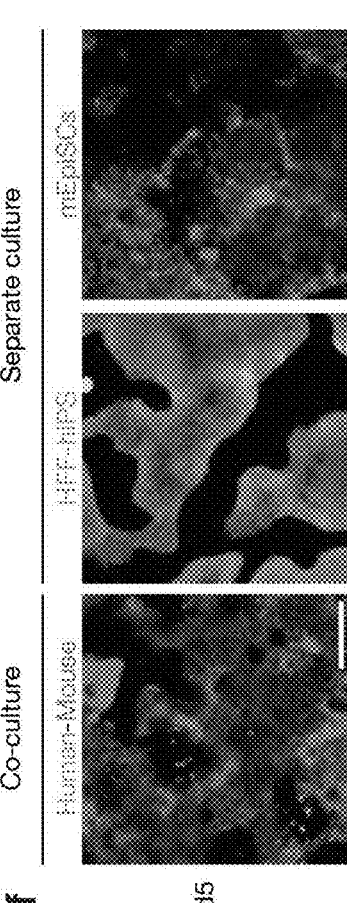

(Passage #51) and H9 hESCs (Passage #49), and HFF-hiPSCs (Passage #21) cultured in FR condition expressed pluripotency transcription factors SOX2 and OCT4. DAPI. Scale bars, 200 µm. c, Long term FR-cultured H9 hESCs (Passage #49) and HFF-hiPSCs (Passage #23) exhibited normal karyotypes. d, Flow cytometry analysis of cell cycle phase distribution of H9 hESCs and mEpiSCs after 3 days in separate-cultures and co-cultures. e, H9 hESCs maintained the expression of pluripotency markers OCT4, SOX2 and TRA-1-60 after 3 days of separate and co-cultures. f, mEpiSCs maintained the expression of pluripotency markers CD24, SOX2, SSEA1 and OCT4 after 3 days of separate and co-cultures FIG. 6 panels a-f show human-mouse primed PSC competition. a, Representative immunofluorescence images of AC3 staining in day 3 H9 hESCs and mEpiSCs separate and co-cultures. DAPI; AC3. Inset, a higher-magnification image of boxed area with dotted line. Scale bars, 200 µm. b, Dot plots showing the percentages of Annexin $V^+$ cells in co-cultured and separately cultured H9 ESCs and mE-piSCs (day 3). n=3, biological replicates, mean±s.e.m. *P<0.05. c, Growth curves of H1 hESCs and mEpiSCs over 5 days in separate (squares) and co-culture (circles). Plating ratio=4:1 (human:mouse), n=3, biological replicates, mean±s.e.m. *P<0.05, **P<0.01. d, Representative fluorescence images showing co-cultured and separately cultured H1 hESCs and mEpiSCs at day 5. Scale bar, 400 µm. e, Growth curves of HFF-hiPSCs and mEpiSCs over 5 days in separate (squares) and co-culture (circles). Plating ratio=4:1 (human:mouse), n=5, biological replicates, mean±s.e.m. *P<0.05, ***P<0.001. f, Representative fluorescence images showing co-cultured and separately cultured HFF-hiPSCs and mEpiSCs at day 5. Scale bar, 400 µm.

Figure 7:
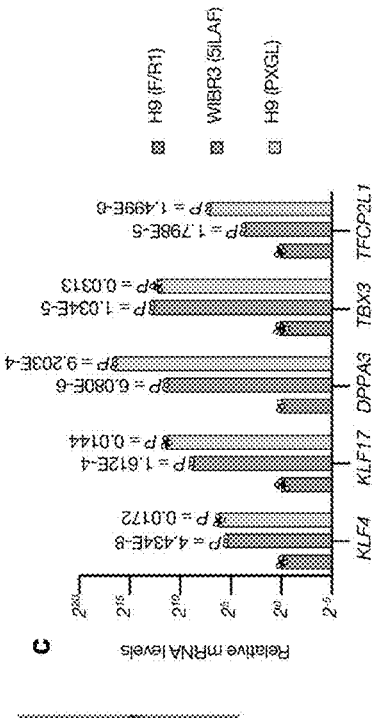
Figure 7:
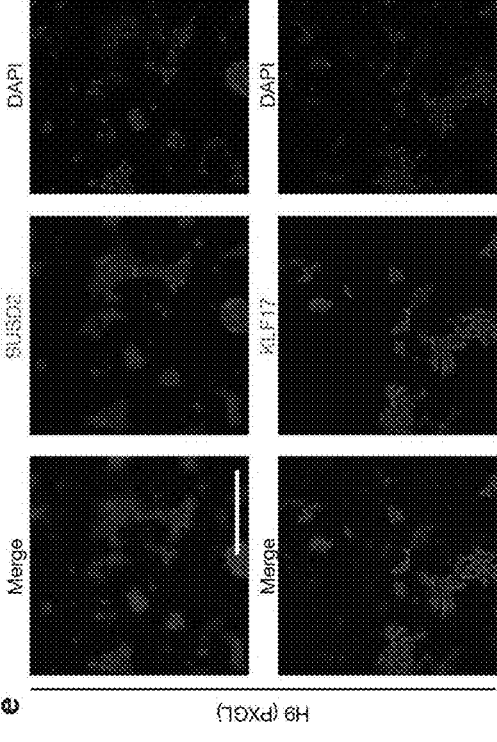
Figure 7:
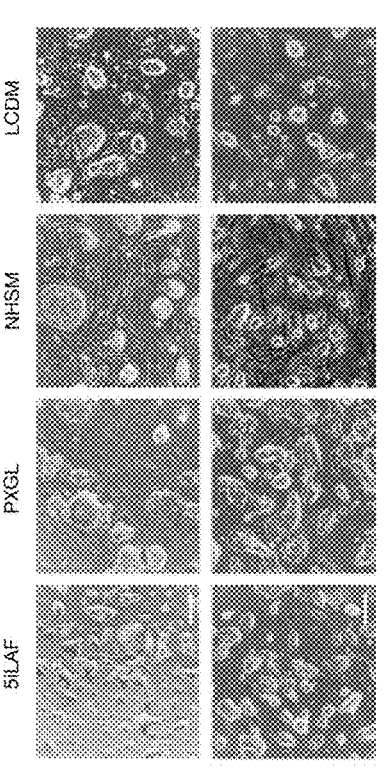
Figure 7:
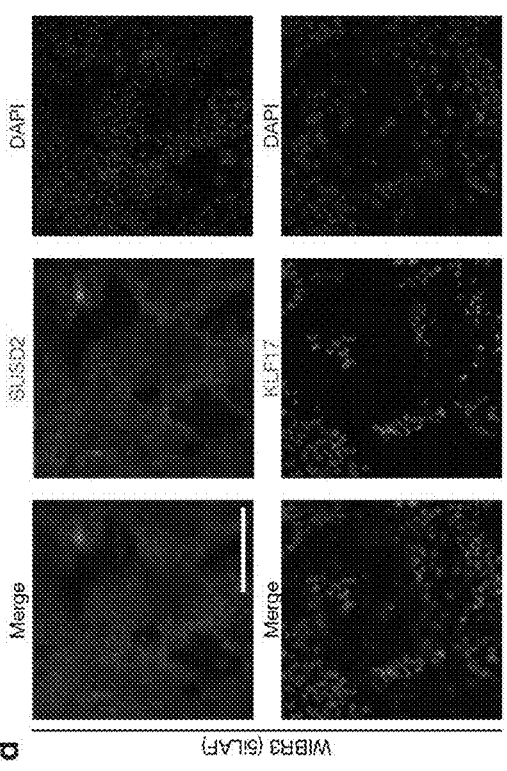
Figure 7:
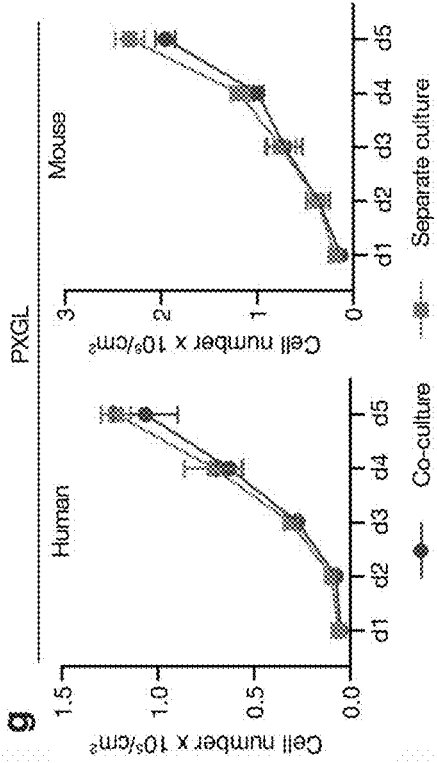
Figure 7:
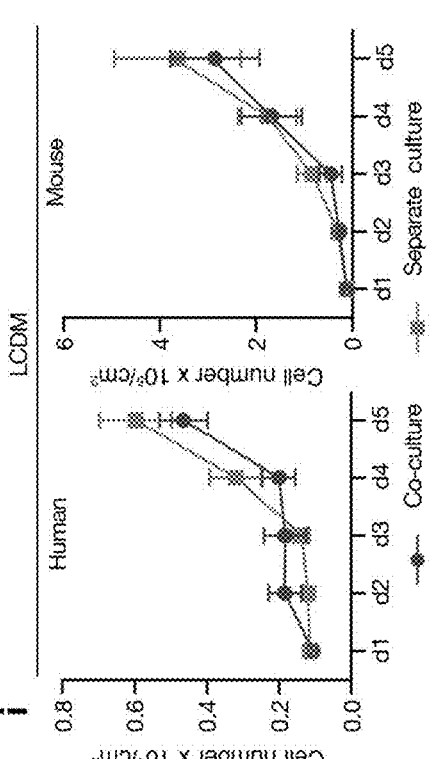
Figure 7:
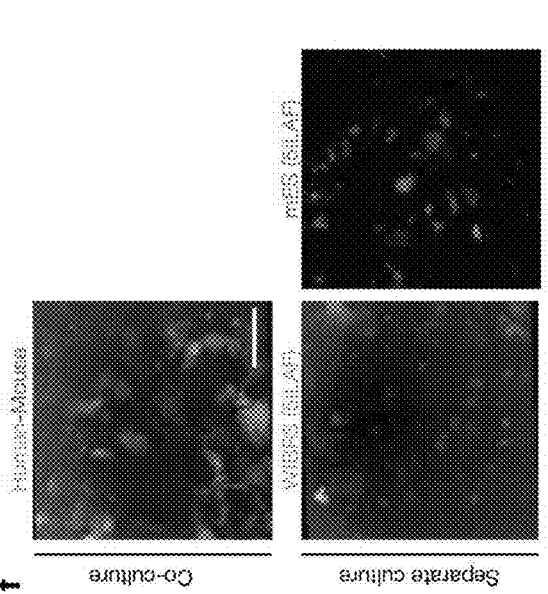
Figure 7:
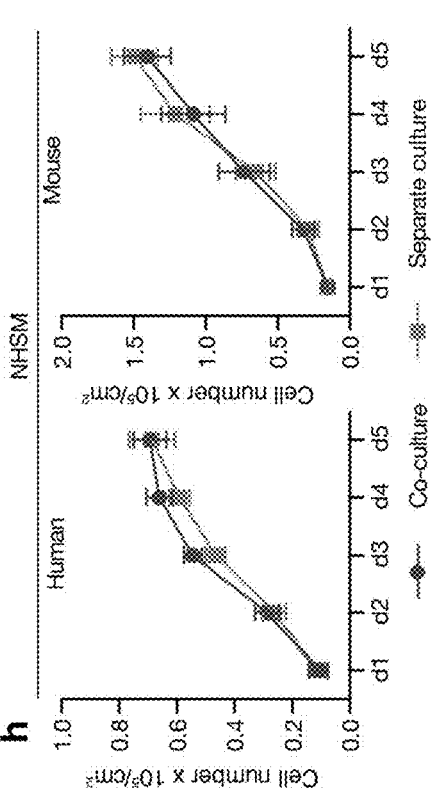
Figure 7:
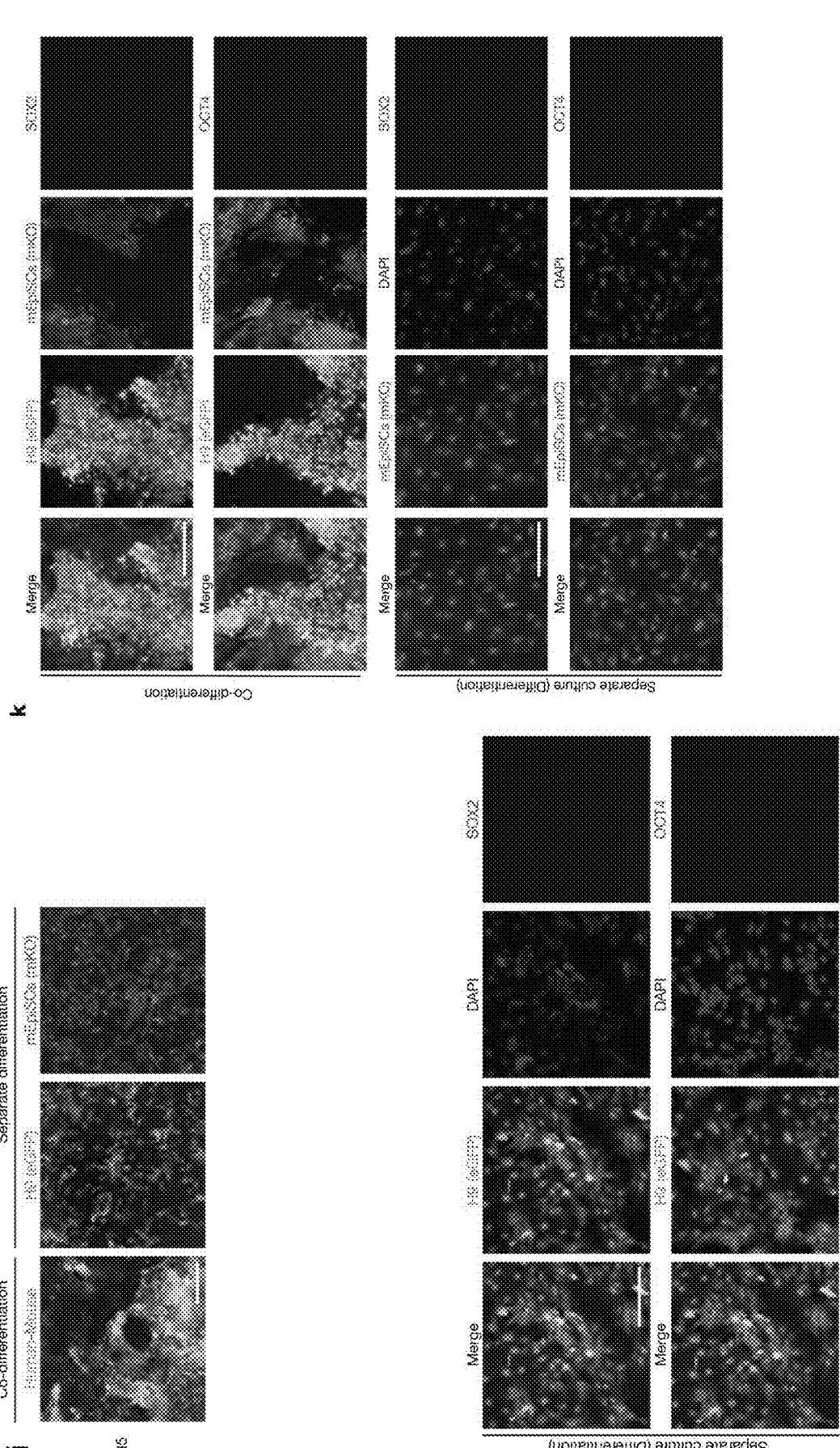

FIG. 7 panels a-l show a lack of cell competition in human-mouse naïve PSC and differentiation co-cultures. a, Representative brightfield images showing typical colony morphologies of human and mouse PSCs cultured in naïve or naïve-like (5iLAF, PXGL, NHSM and LCDM) conditions. Scale bars, 200 µm. b, A coat-color chimera generated by J1 mESCs cultured in the 5iLAF condition. c, RT-qPCR analysis of relative expression levels of selected naïve pluripotency markers in naïve WIBR3 (5iLAF) and H9 (PXGL) hESCs compared to FR-cultured H9 hESCs. n=3, biological replicates, mean±s.e.m. *P<0.001. d,e, Representative immunofluorescence images of SUSD2 and KLF17 in naïve hESCs cultured in 5iLAF (WIRB3) and PXGL (H9) conditions. Scale bars, 200 µm. f, Representative fluorescence images showing day 5 co-cultured and separately cultured naïve WIBR3 hESCs (green) and J1 mESCs under 5iLAF condition. Scale bar, 400 µm. g, Growth curves of H9 hESCs and J1 mESCs cultured under PXGL condition over 5 days in separate (squares) and co-culture (circles). n=3, biological replicates, mean #s.e.m. h, Growth curves of H9 hESCs and mESCs cultured under NHSM condition over 5 days in separate (squares) and co-culture (circles). n=3, biological replicates, mean±s.e.m. i, Growth curves of human iPS-EPSCs and mouse EPSCs (mEPSCs) cultured under LCDM condition over 5 days in separate (squares) and co-culture (circles). n=3, biological replicates, mean±s.e.m. j, Representative fluorescence images showing co-cultured and separately cultured H9 hESCs and mEpiSCs under a differentiation condition at day 5. Scale bar, 400 µm. k, l, Representative immunofluorescence images showing day5 H9 hESCs and mEpiSCs under the differentiation condition lost expression of pluripotency transcription factors SOX2 and OCT4. DAPI. Scale bars, 200 µm.

Figure 8:
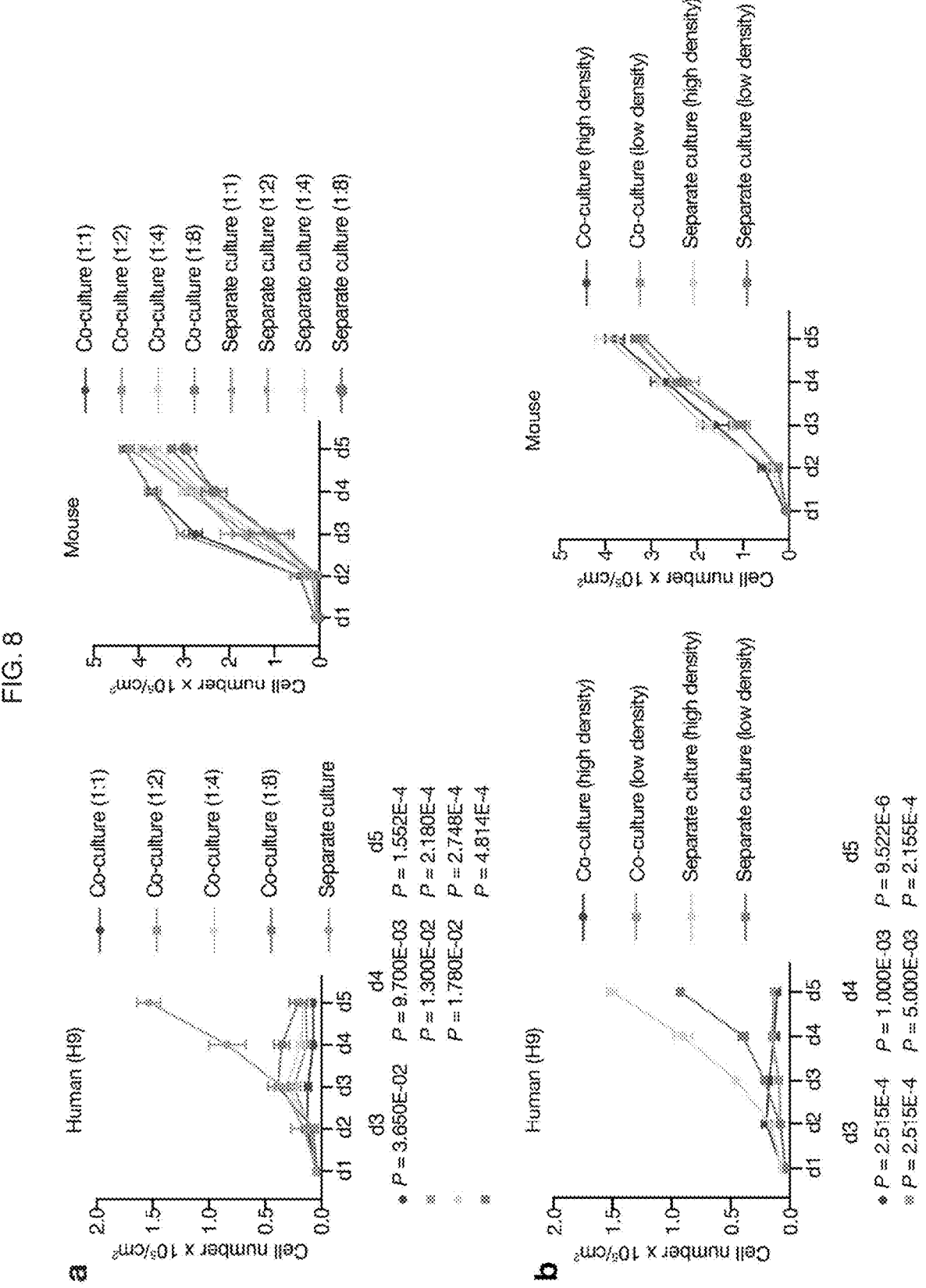
Figure 8:
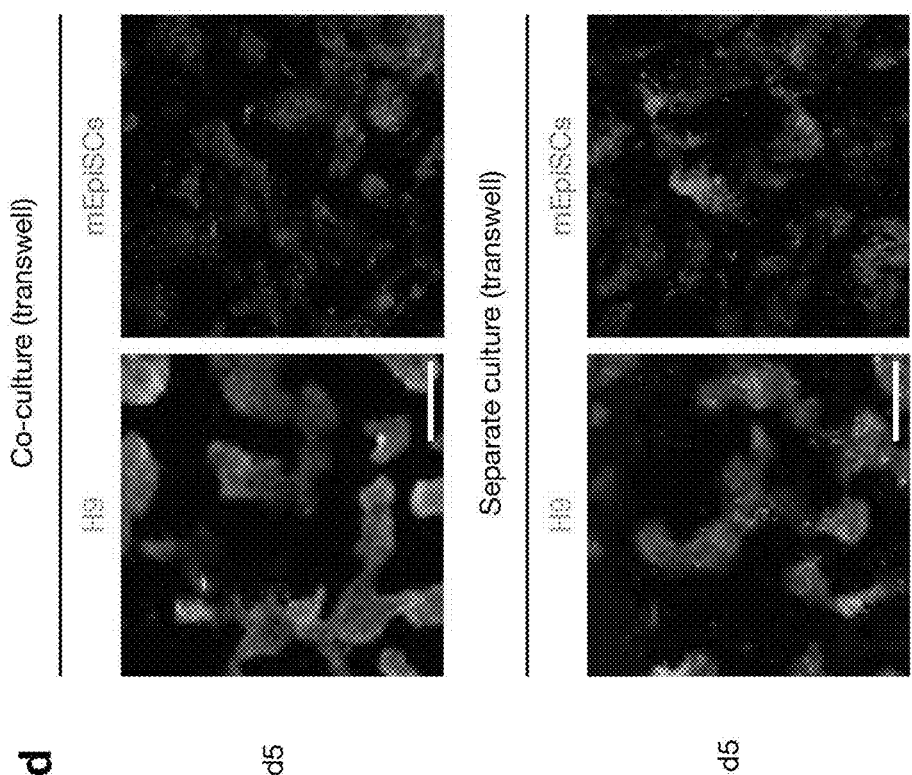
Figure 8:
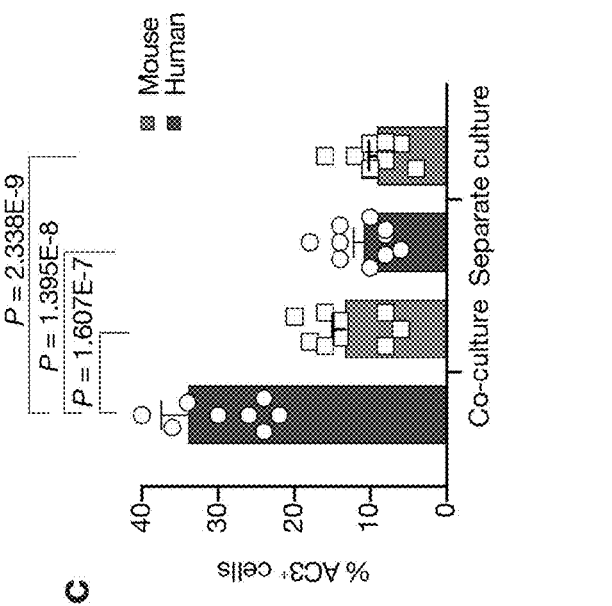
Figure 8:
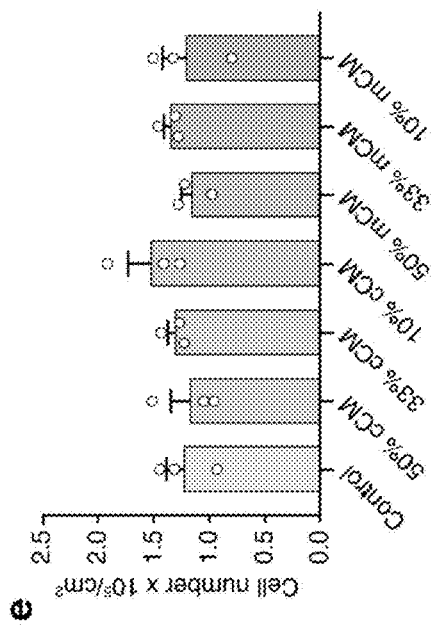

FIG. 8 panels a-e show mechanisms underlying human-mouse primed PSC competition. a, Growth curves of H9 hESCs (left) and mEpiSCs (right) plated at different ratio (mouse: human=1:1, 1:2, 1:4 and 1:8) over 5 days in separate and co-cultures. The seeding number of H9 hESCs was fixed at $1×10^4/cm^2$ while mE-piSCs seeding numbers were adjusted according to different seeding ratios. n=3, biological replicates, mean±s.e.m. *P<0.05, P<0.01, separate cultures compared with co-cultures. b, Growth curves of H9 hESCs and mEpiSCs plated at high and low densities (high $1.25×10^5/cm^2$; and low, $0.625×10^5/cm^2$, 4:1 ratio) over 5 days in separate and co-cultures. n=3, biological replicates, mean±s.e.m. P<0.01, *P<0.001. c, Quantification of apoptotic cells by counting $AC3^+$ cells of day 3 co-cultured and separately cultured H9 hESCs (first and third bars) and mEpiSCs (second and fourth bars), plating ratio=1:1 (human:mouse), n=10, 10 randomly selected fields ($318.2×318.2$ $µm^2$ each) from three independent immunostaining experiments per sample, mean±s.e.m. *P<0.001. d, Representative fluorescence images showing transwell co-cultured and separately cultured H9 hESCs and mEpiSCs at day 5. Scale bar, 400 µm. e, Day 5 live H9 hESC cell numbers/$cm^2$ after treatments with different dosages (50%, 33% and 10%) of conditioned medium (CM) collected from H9 hESCs and mEpiSCs co-cultures (cCM), or mEpiSCs separate cultures (mCM). n=3, biological replicates, mean±s.e.m.

Figure 9:
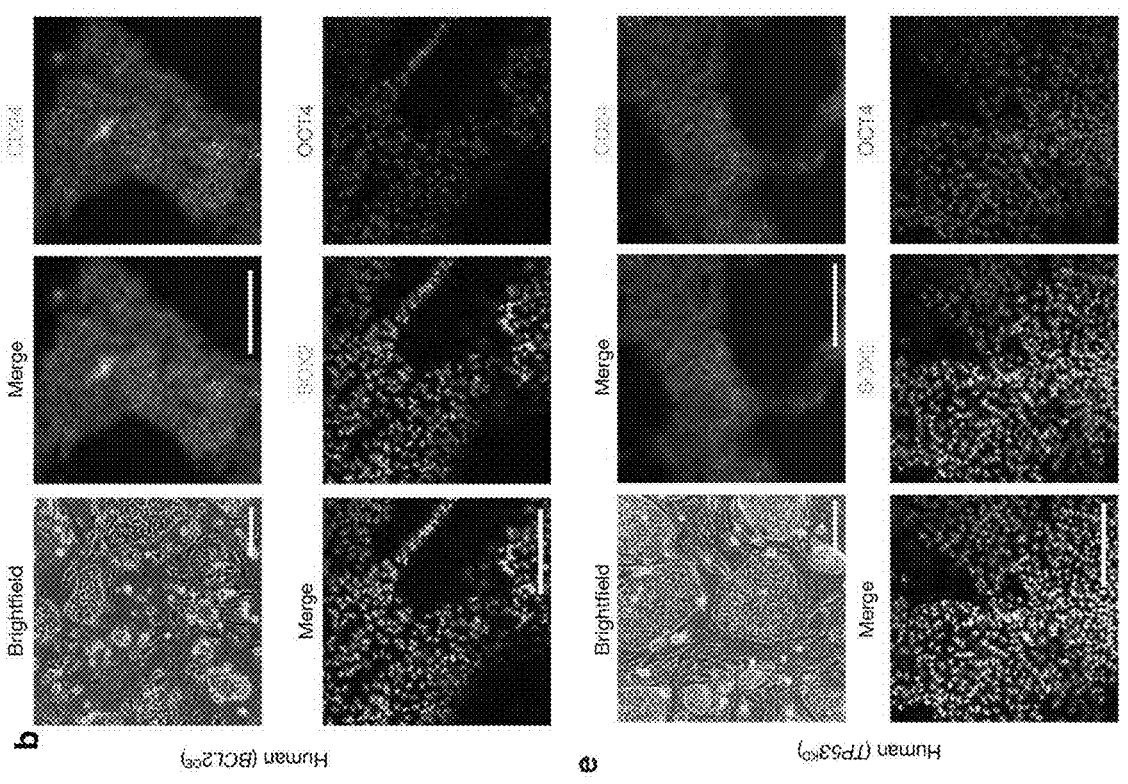
Figure 9:
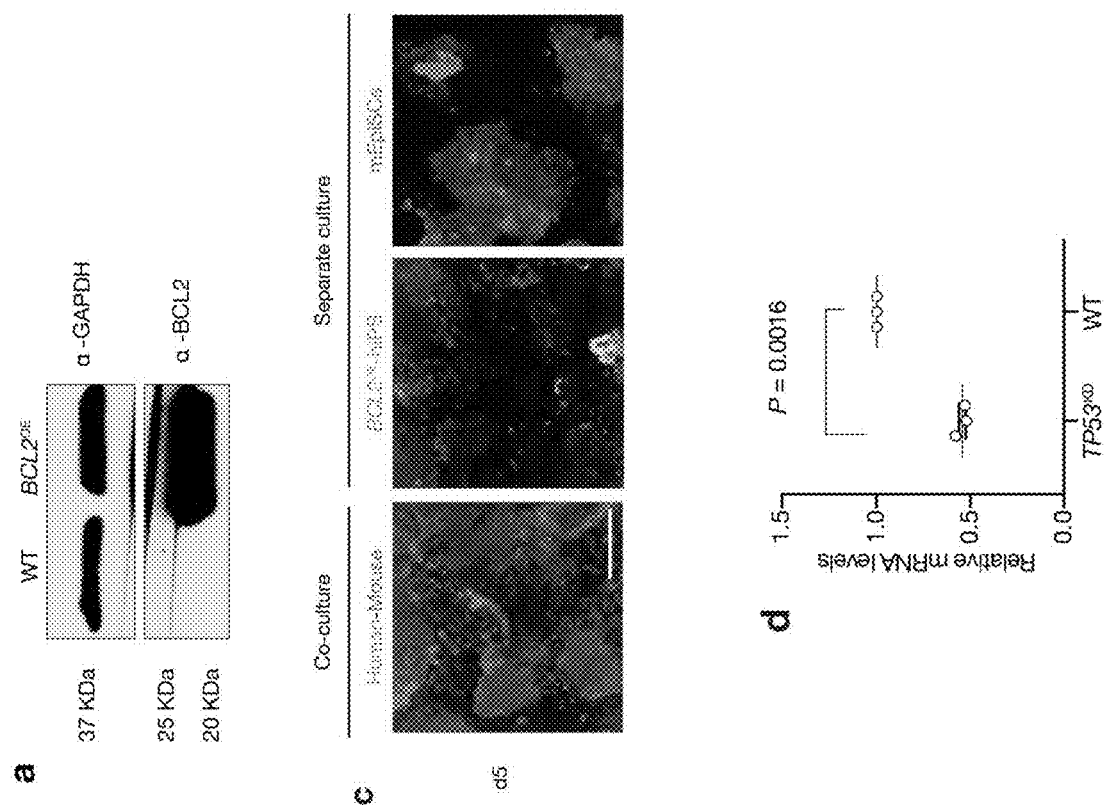
Figure 9:
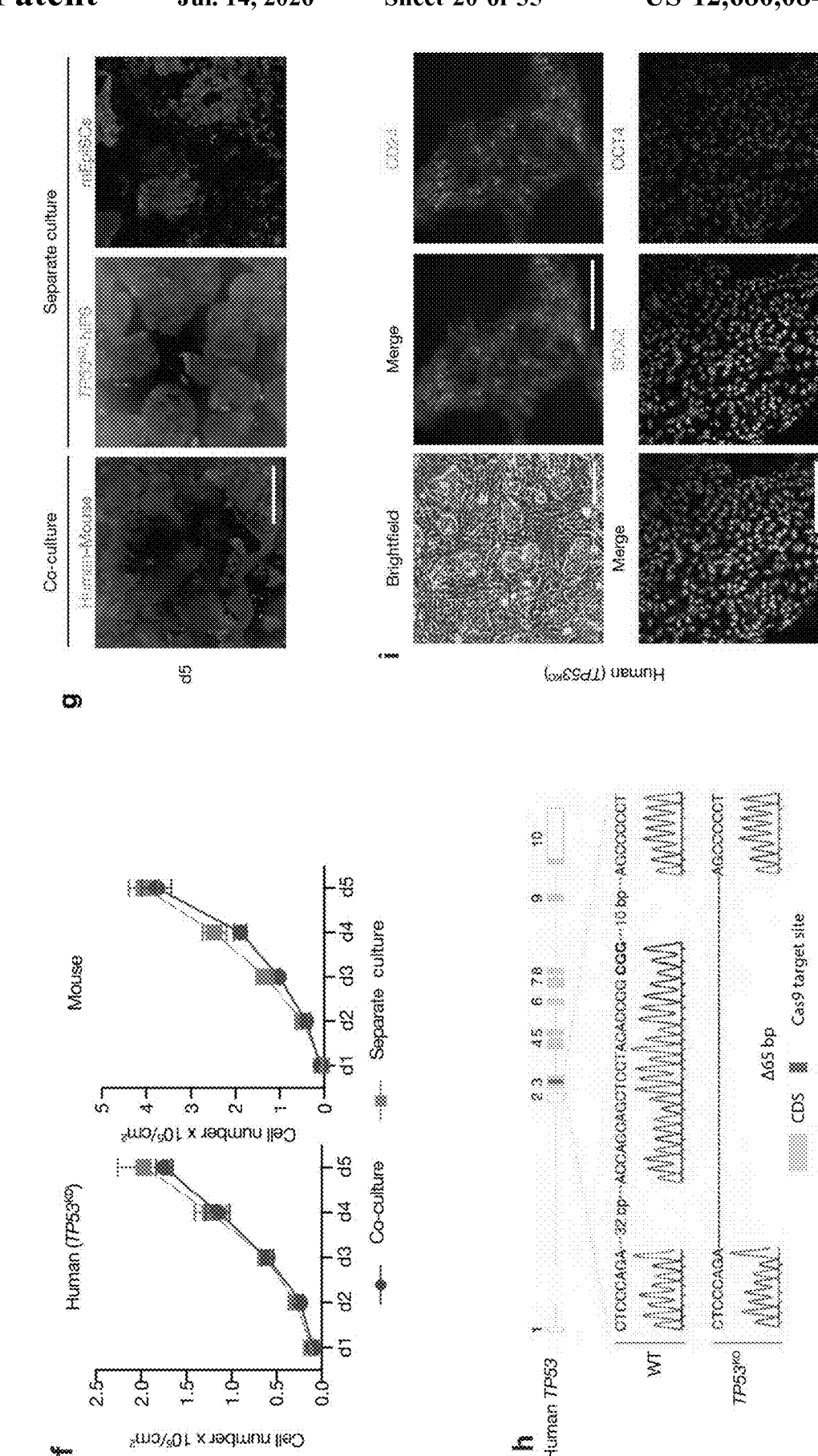
Figure 9:
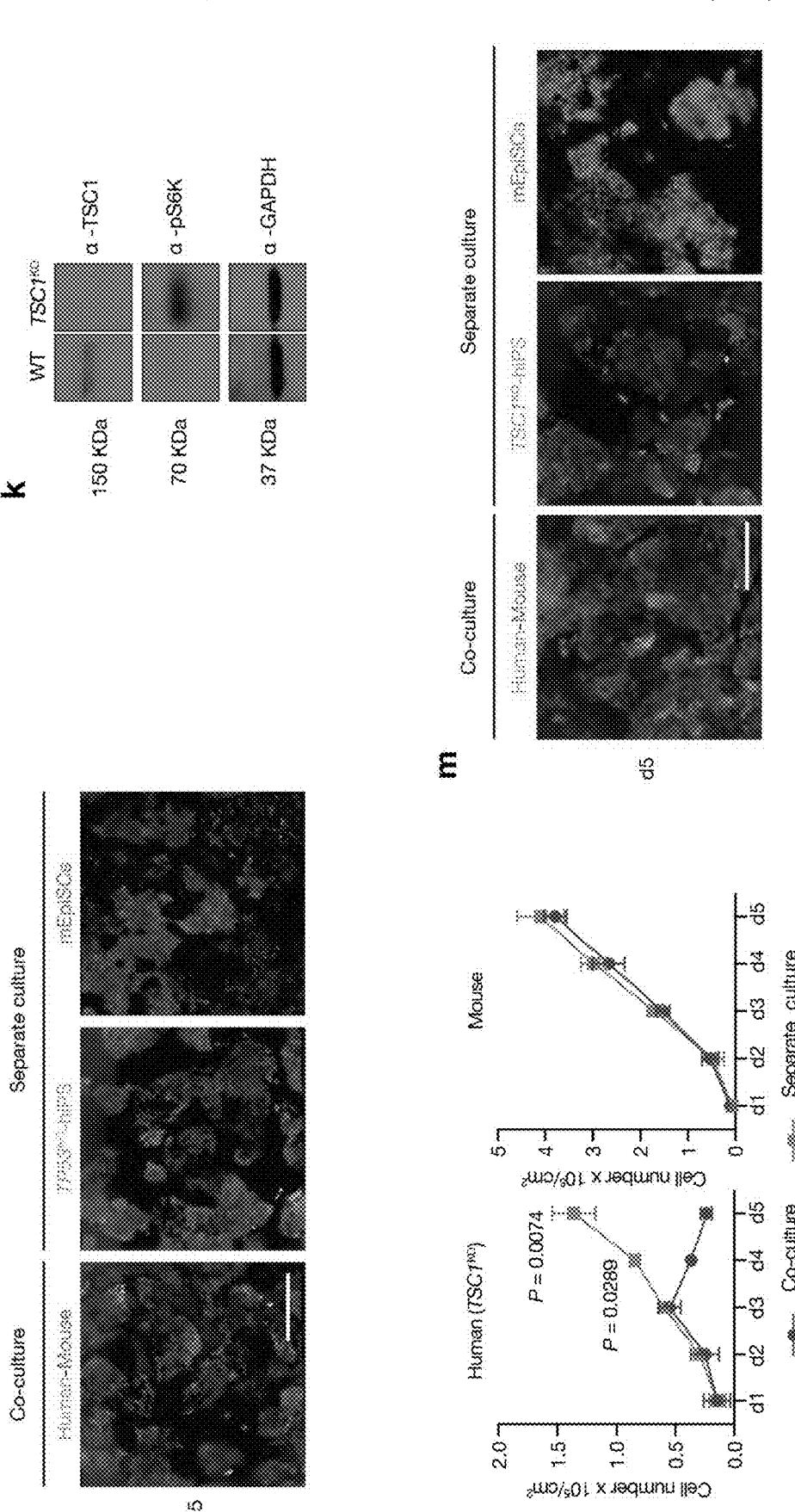

FIG. 9 panels a-m show overcoming human-mouse primed PSC competition by blocking human cell apoptosis. a, Western blot analysis confirmed the overexpression of BCL-2 in BCL-$2^{CE}$-hiPSCs. GAPDH was used as a loading control. b, Representative brightfield and immunofluorescence images showing long term cultured BCL-$2^{OE}$-hiPSCs (BCL-2 OE) expressed core (SOX2; OCT4) and primed (CD24) pluripotency markers. DAPI. Scale bars, 200 µm. c, Representative fluorescence images showing co-cultured and separately cultured BCL-$2^{OE}$-hiPSCs and mEpiSCs at day 5. Scale bar, 400 µm. d, Dot plot showing the qRT-PCR results confirming knockdown of TP53 transcript in TP53$^{KD}$-hiPSCs. n=3, biological replicates, mean±s.e.m. **P<0.01. e, Representative brightfield and immunofluorescence images showing long term cultured TP53$^{KD}$-hiPSCs (TP53 KD) expressed core (SOX2; OCT4) and primed (CD24) pluripotency markers. DAPI. Scale bars, 200 µm. f, Growth curves of TP53$^{KD}$-hiPSCs and mEpiSCs over 5 days in separate (squares) and co-culture (circles). n=3, biological replicates, mean±s.e.m. g, Representative fluorescence images showing co-cultured and separately cultured TP53$^{KD}$-hiPSCs and mEpiSCs at day 5. Scale bar, 400 µm. h, Sanger sequencing result showing out-of-frame homozygous "65 bp" deletion mutation in TP53$^{KO}$-hiPSCs. CTCCCAGA ACCAGCAGCTCCTACACCGGCGG is SEQ ID NO: 45; AGCCCCCT. i, Representative brightfield and immunofluorescence images showing long term cultured TP53$^{KO}$-hiPSCs (TP53 KO) expressed core (SOX2; OCT4) and primed (CD24) pluripotency markers. DAPI. Scale bars, 200 µm. j Representative fluorescence images showing co-cultured and separately cultured TP53$^{KO}$-hiPSCs and mEpiSCs at day 5. Scale bar, 400 µm. k, Western blot analysis confirmed the lack of TSC1 protein expression and activation of mTOR pathway (S6K phosphorylation, pS6K) in TSC1$^{KO}$-hiPSCs. GAPDH was used as a loading control. l, Growth curves of TSC1$^{KO}$-hiPSCs and mEpiSCs over 5 days in separate (squares) and co-culture (circles). n=3, biological replicates, mean±s.e.m. *P<0.05, **P<0.01.

m, Representative fluorescence images showing co-cultured and separately cultured TSC1$^{KO}$-hiPSCs and mEpiSCs at day 5. Scale bar, 400 μm.

Figure 10:
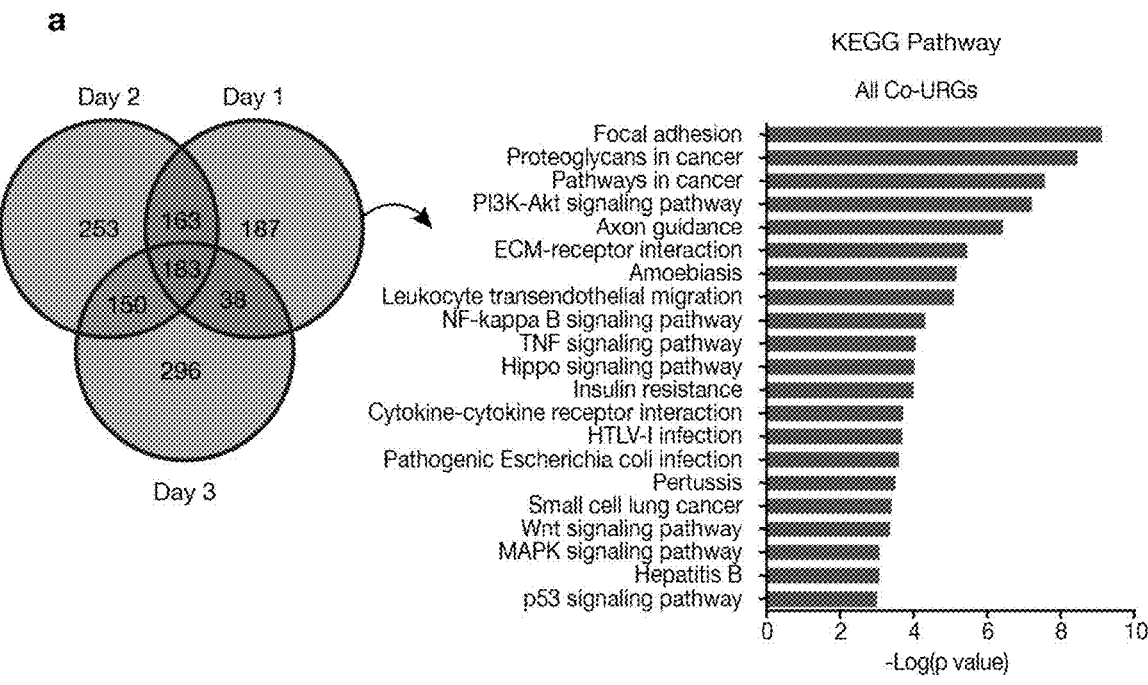
Figure 10:
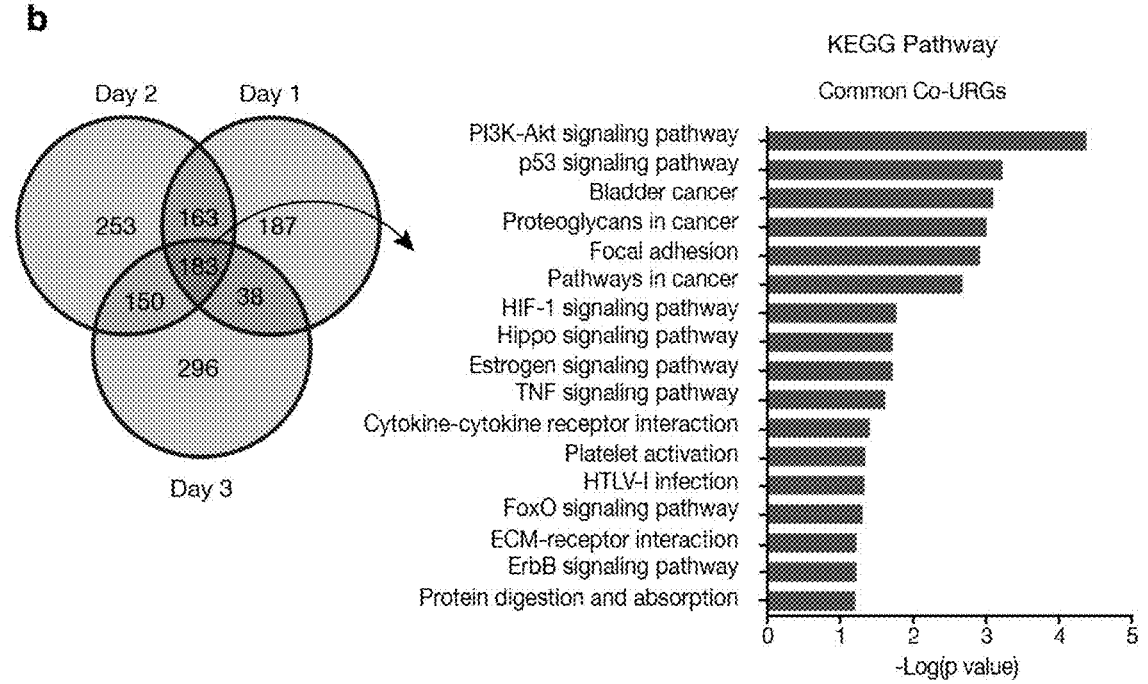
Figure 10:
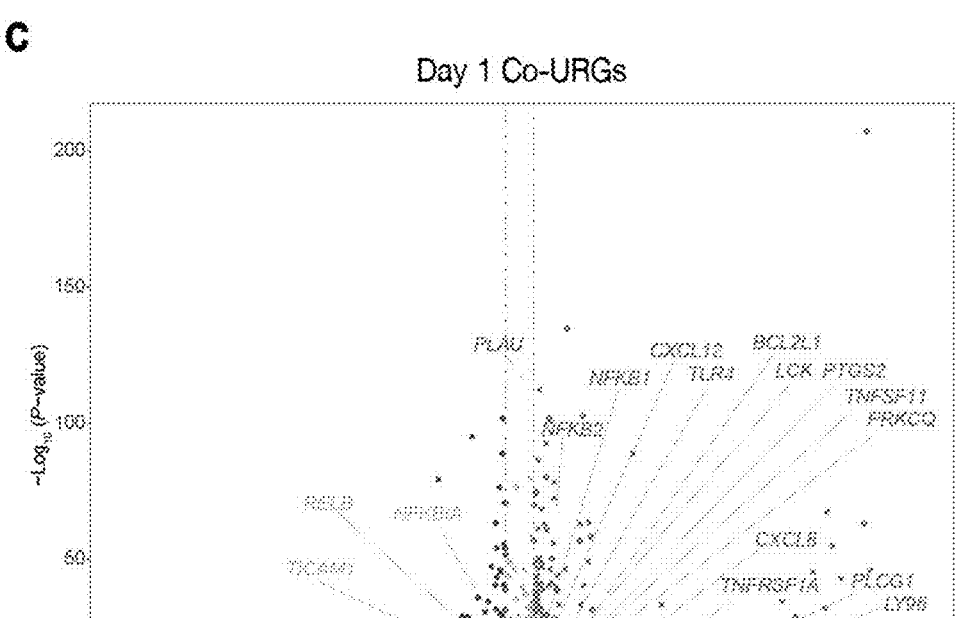
Figure 10:
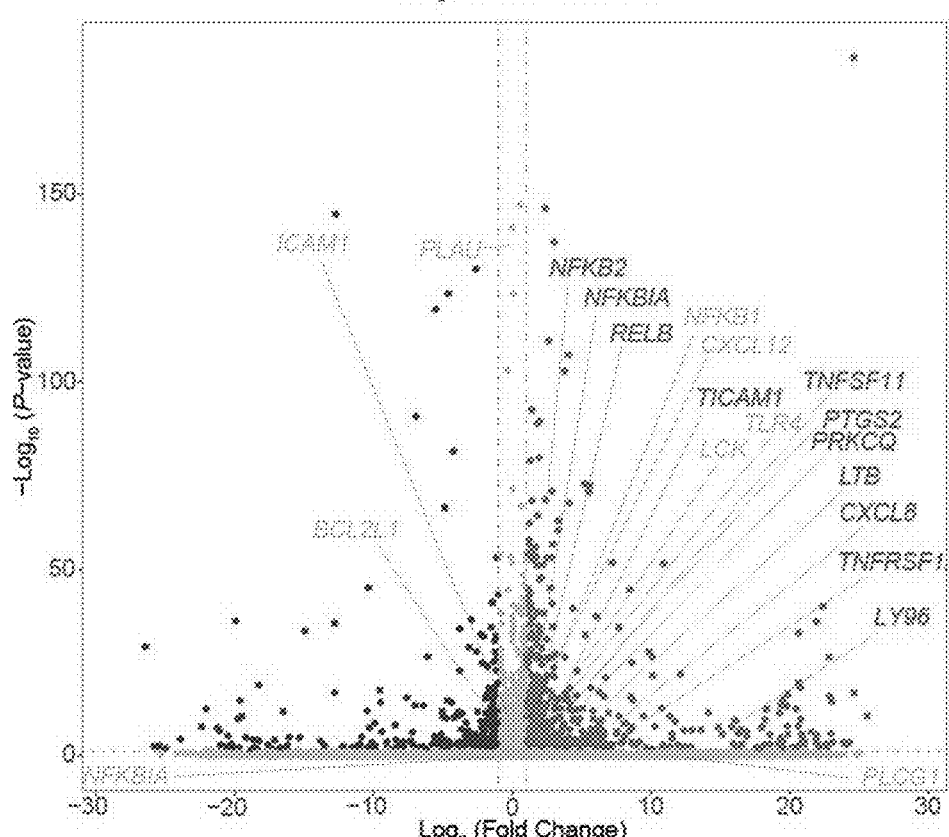
Figure 10:
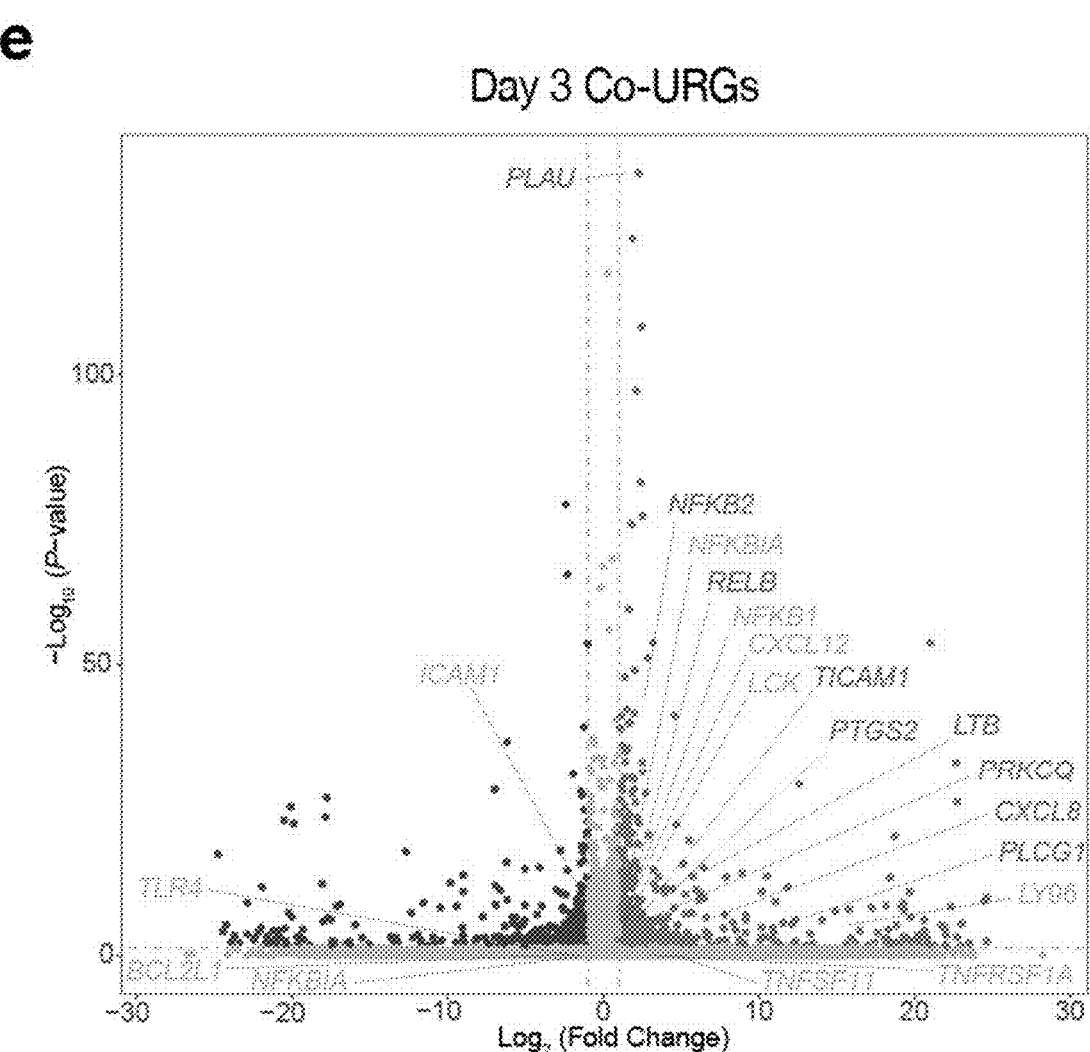

FIG. 10 panels a-e show comparative RNA-seq analysis between co-cultured and separately cultured H9 hESCs. a, KEGG pathways enriched in all (days 1, 2 and 3 combined) Co-URGs in H9 hESCs. b, KEGG pathways enriched in common (commonly shared among days 1, 2, 3) Co-URGs in H9 hESCs. c-e, A volcano plot showing significantly up-(left side) and down-regulated (right side) genes in co-cultured versus separately cultured H9 hESCs on day 1 (c), day 2 (d), and day 3 (e). TLR/NF-κB pathway related genes are highlighted in the volcano plots.

Figure 11:
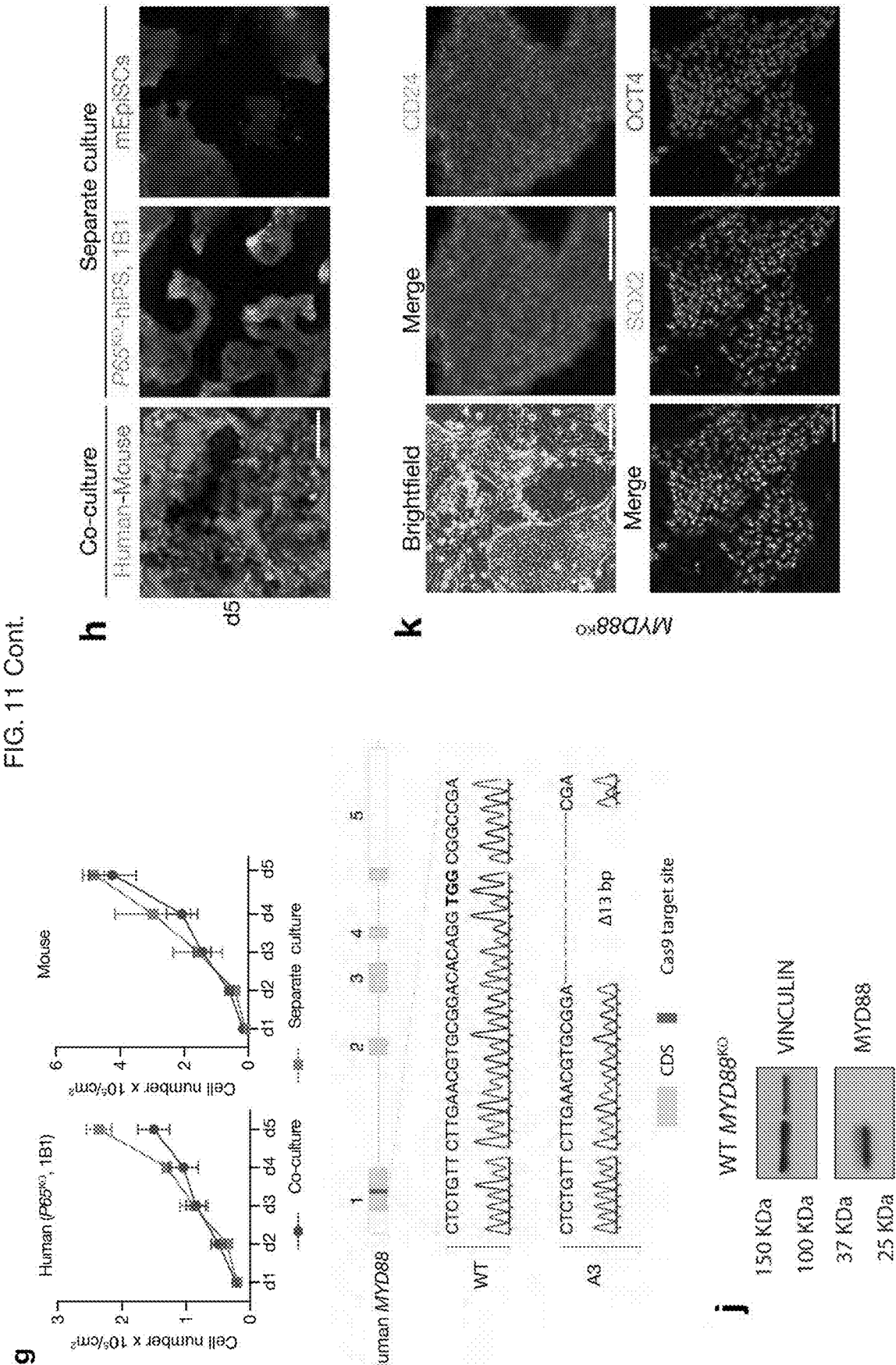
Figure 11:
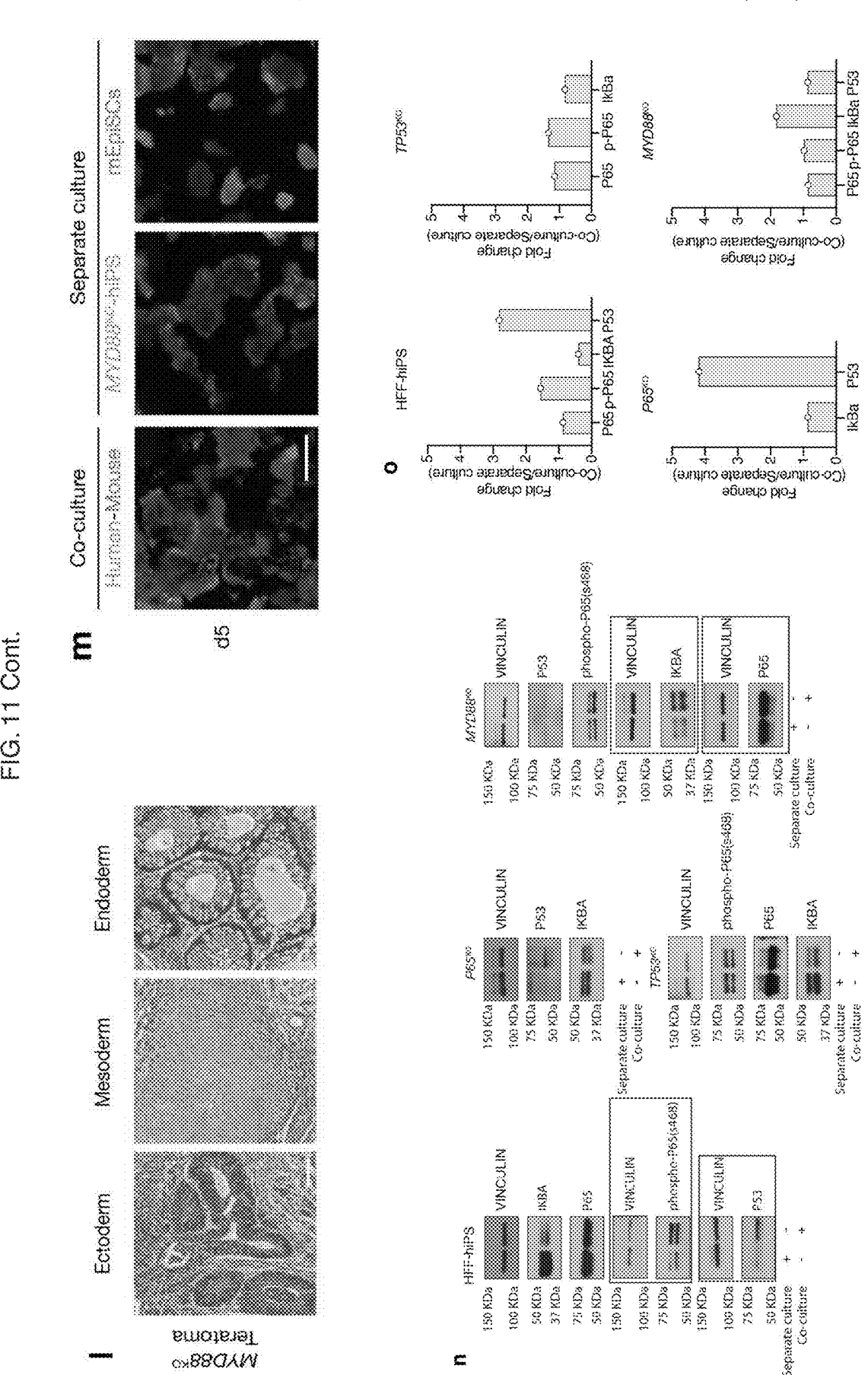

FIG. 11 panels a-o show that genetic inactivation of P65 and MYD88 in human PSCs overcomes human-mouse primed PSC competition. a, Sanger sequencing results showing out-of-frame homozygous "1 bp" insertion mutations in two independent P65$^{KO}$-hiPSC clones: 1A3 and 1B1. ATTGAGCAGCCCAAGCAGCGGGG is SEQ ID NO:46; ATTGAGCAGCCCAAGCAAGCGGGG is SEQ ID NO:47; b, Western blot analysis confirmed the lack of P65 protein expression in several independent P65$^{KO}$-hiPSC clones. GAPDH was used as a loading control. c, P65$^{KO}$-hiPSCs (clone #1A3) maintained normal karyotype after long term passaging (passage 10). d, Rep presentative brightfield and immunofluorescence images showing long-term FR-cultured P65KO-hiPSCs maintained stable colony morphology and expressed core (SOX2; OCT4) and primed (CD24) pluripotency markers. DAPI. Scale bars, 200 μm. e, Representative hematoxylin and eosin staining images of teratomas generated by P65$^{KO}$-hiPSCs (clone #1A3) showing lineage differentiation towards three germ layers. Scale bar, 200 μm. f. Representative fluorescence images showing co-cultured and separately cultured P65$^{KO}$-hiPSCs (clone #1A3) and mEpiSCs at day 5. Scale bar, 400 μm. g, Growth curves of P65$^{KO}$-hiPSCs (clone #1B1) and mEpiSCs over 5 days in separate (squares) and co-culture (circles). n=3, biological replicates, mean±s.e.m. h, Representative fluorescence images showing co-cultured and separately cultured P65KO-hiPSCs (clone #1B1) and mEpiSCs at day 5. Scale bar, 400 μm. i, Sanger sequencing result showing out-of-frame homozygous "13 bp" deletion mutation in MYD88$^{KO}$-hiPSCs. CTCTGTTCTT-GAACGTGCGGACACAGGTGGCGGCCGA is SEQ ID NO:48 CTCTGTTCTTGAACGTGCGGACGA is SEQ ID NO:49. j, Western blot analysis confirmed the lack of MYD88 protein expression in MYD88$^{KO}$-hiPSCs. k, Representative brightfield and immunofluorescence images showing long-term FR-cultured MYD88$^{KO}$-hiPSCs maintained stable colony morphology and expressed core (SOX2; OCT4) and primed (CD24) pluripotency markers. DAPI. Scale bars, 200 μm. l, Representative hematoxylin and eosin staining images of a teratoma generated by MYD88$^{KO}$-hiPSCs showing lineage differentiation towards three germ layers. Scale bar, 200 μm. m, Representative fluorescence images showing co-cultured and separately cultured MYD88$^{KO}$-hiPSCs and mEpiSCs at day 5. Scale bar, 400 μm. n, Western blot analyses of IκBα, P65, Phospho-P65 (s468), P53 protein expression levels in co-cultured and separately cultured WT and mutant (P65$^{KO}$-, TP53$^{KO}$- and MYD88$^{KO}$) HF-hiPSCs. Vinculin was used as loading controls. Boxed areas were from separate blots. o, Bar graphs showing the fold changes of protein expression levels (shown in n) in co-cultured versus separately cultured WT and mutant HFF-hiPSCs. n=1, biological replicate.

Figure 12:
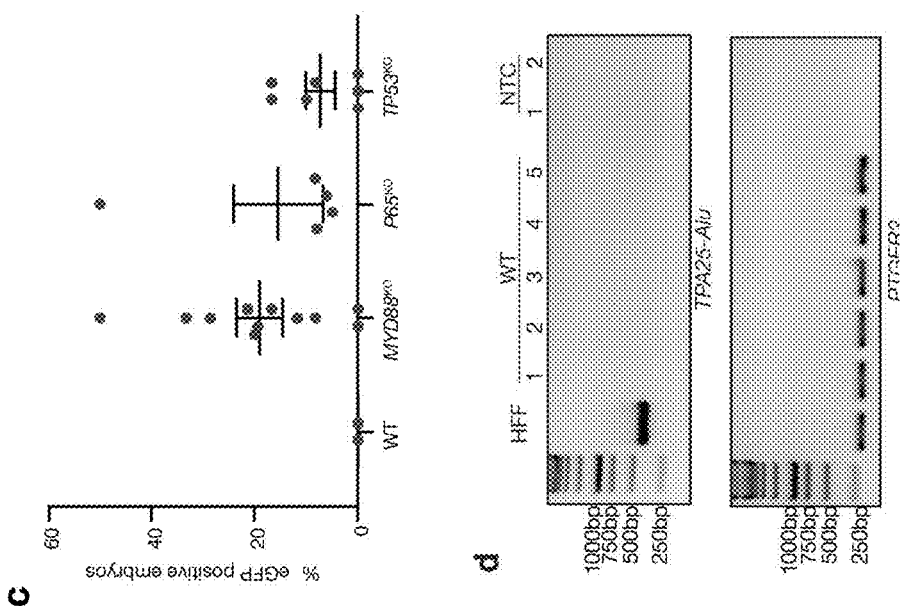
Figure 12:
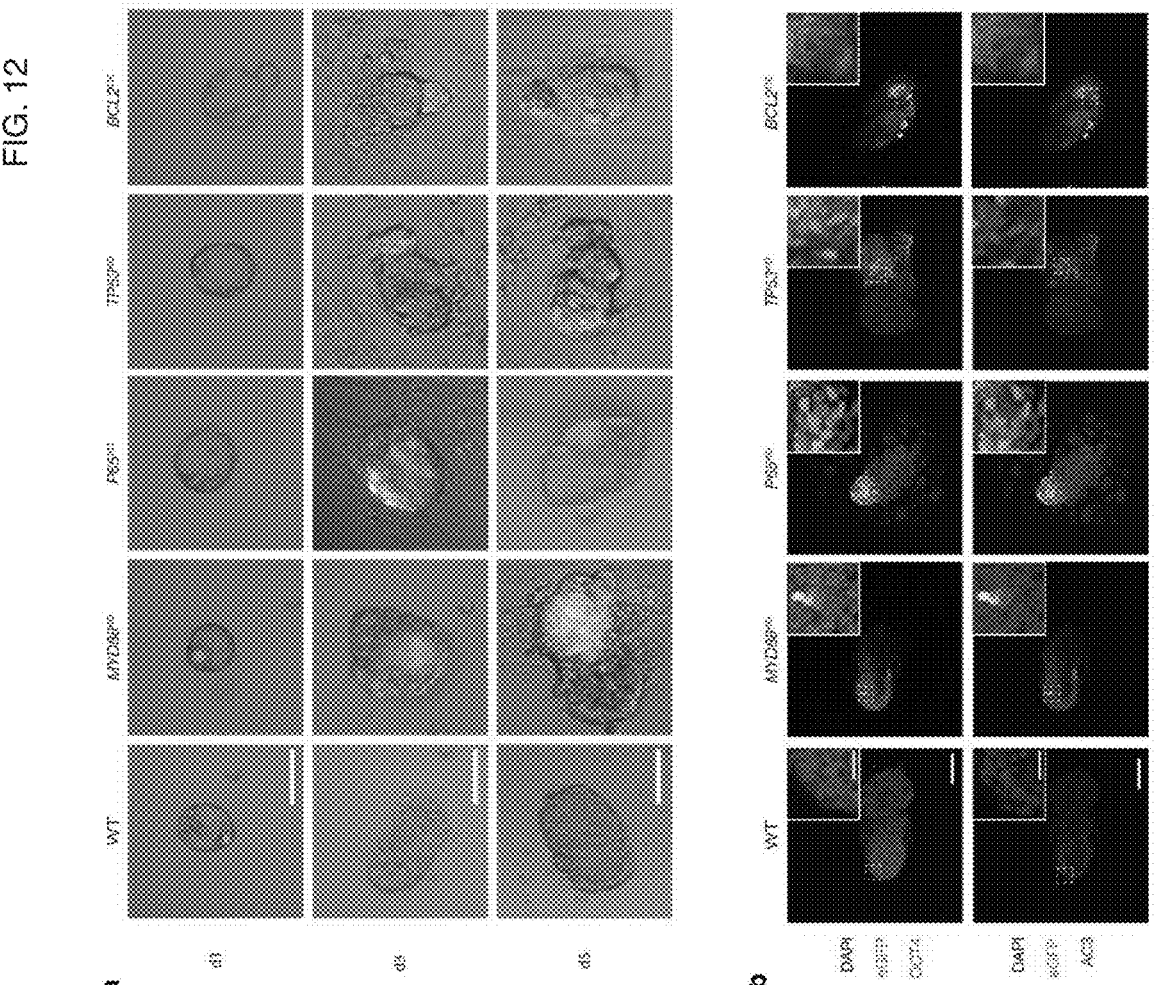
Figure 12:
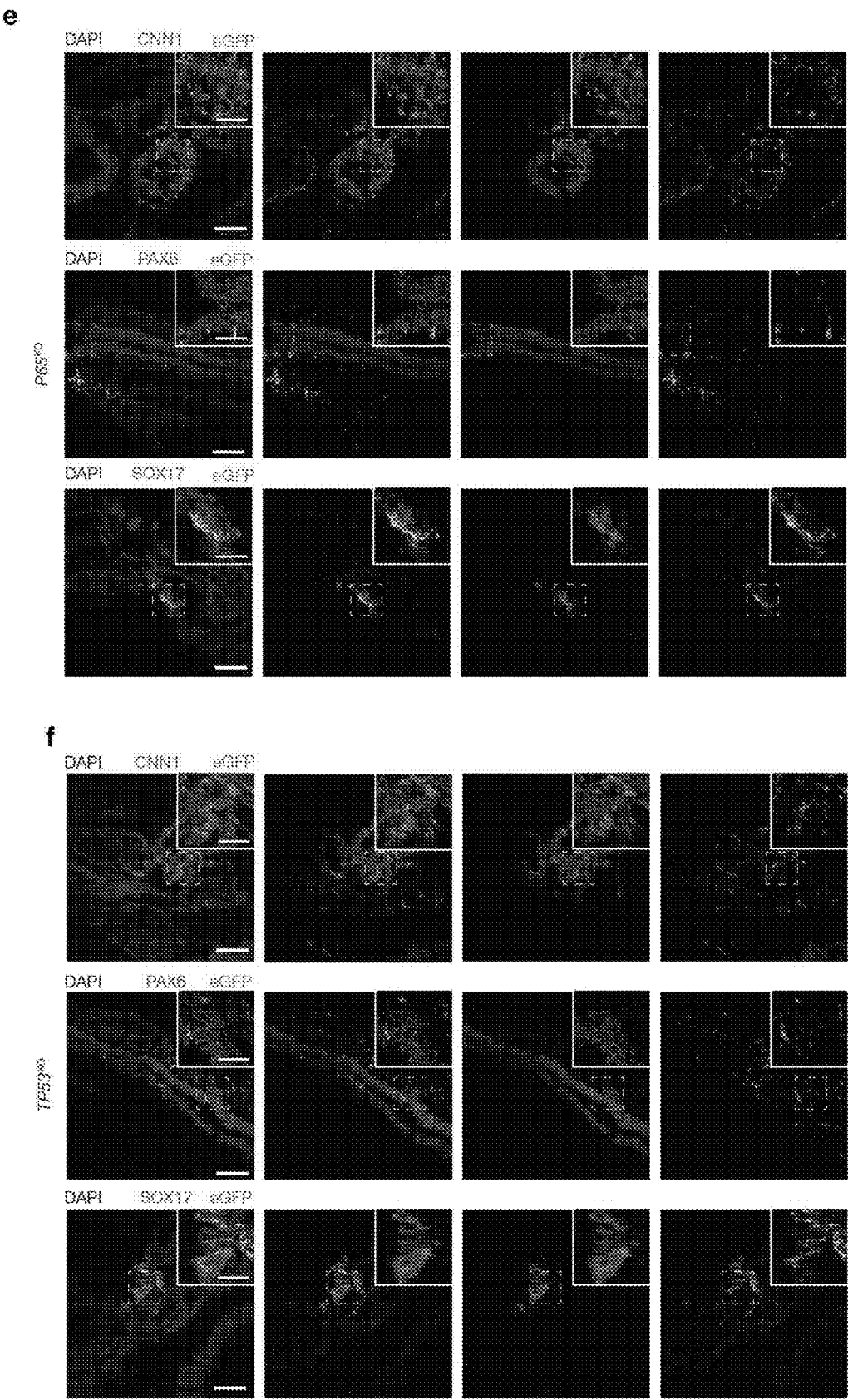

FIG. 12 panels a-f show that overcoming interspecies PSC competition enhances primed human PSCs survival and chimerism in early mouse embryos. a, Representative brightfield and fluorescence merged images of mouse embryos cultured for 1 day (d1), 3 days (d3) and 5 days (d5) following blastocyst injection of WT-, MYD88$^{KO}$-, P65$^{KO}$-, TP53$^{KO}$- and BCL-2$^{OE}$-hiPSCs. Scale bars, 100 μm. b, Representative immunofluorescence images of day 5 cultured mouse embryos co-stained with OCT4, EGFP and AC3 after blastocyst injection of WT, MYD88$^{KO}$-, P65$^{KO}$-, TP53$^{KO}$- and BCL-2$^{OE}$-hiPSCs. Top, EGFP/OCT4 merged images with DAPI; bottom, EGFP/AC3 merged images with DAPI. Scale bars, 100 μm and 50 μm (insets). c, Dot plot showing the percentages of EGFP positive E8-9 mouse embryos derived from WT-, MYD88$^{KO}$-, P65$^{KO}$- and TP53$^{KO}$-hiPSCs. Each dot represents one embryo transfer experiment. mean±s.e.m. (also see Table 4). d, Genomic PCR analysis of selected E8-9 mouse embryos derived from blastocyst injection of WT-hiPSCs using a human specific Alu primer (TPA25-Alu). PTGER2 primer was used for loading control. HFF (HFF-iPSCs) was used as a positive control. NTC, non-template control. e, f, Representative immuno-fluorescence images showing contribution and differentiation of P65$^{KO}$-hiPSCs (e) and TP53$^{KO}$-hiPSCs (f) in E8-9 mouse embryos. Embryo sections were stained with antibodies against EGFP and lineage markers including CALPONIN 1 (mesoderm, top), PAX6 (ectoderm, middle) and SOX17 (endoderm, bottom).

Figure 13:
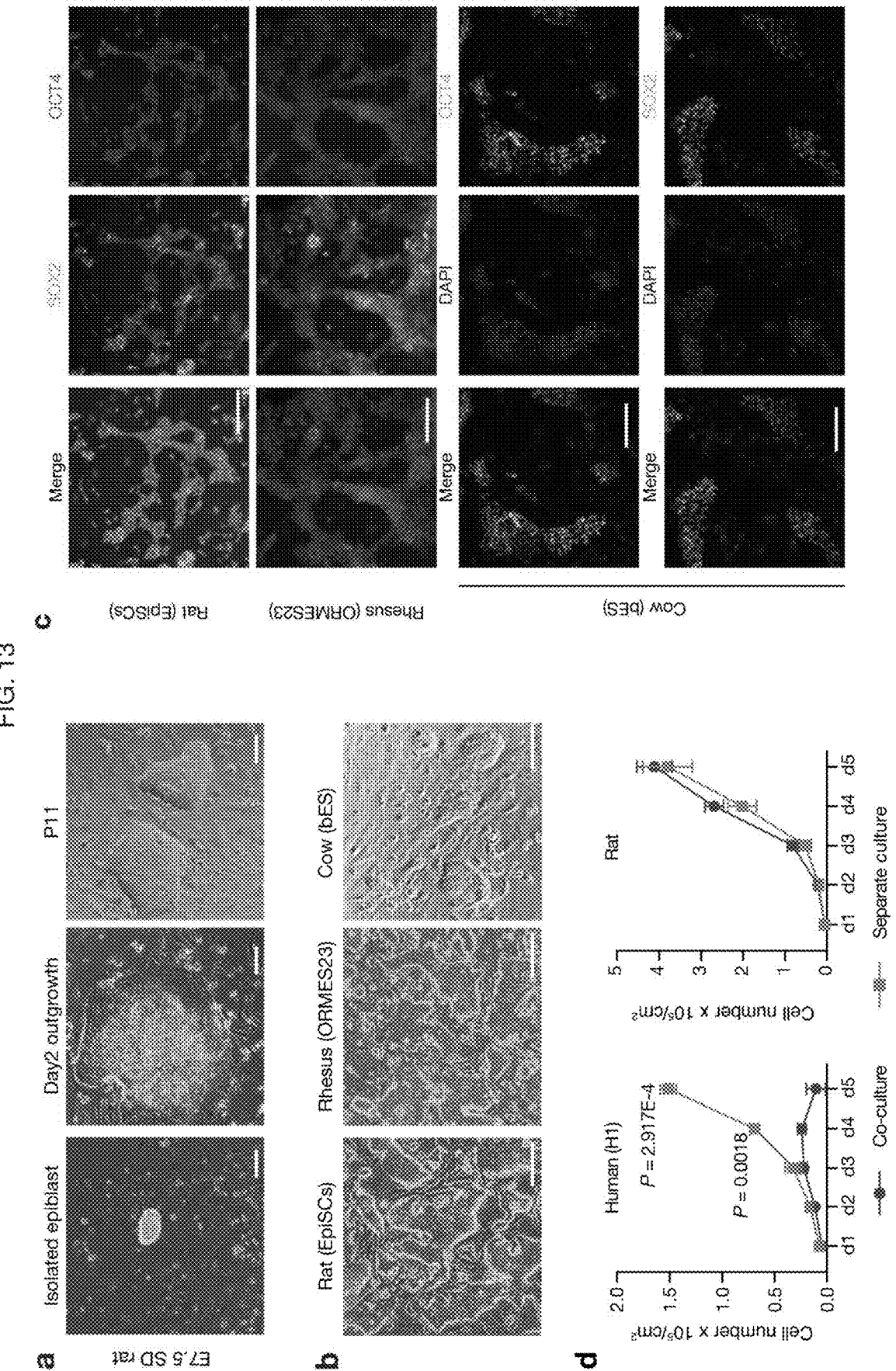
Figure 13:
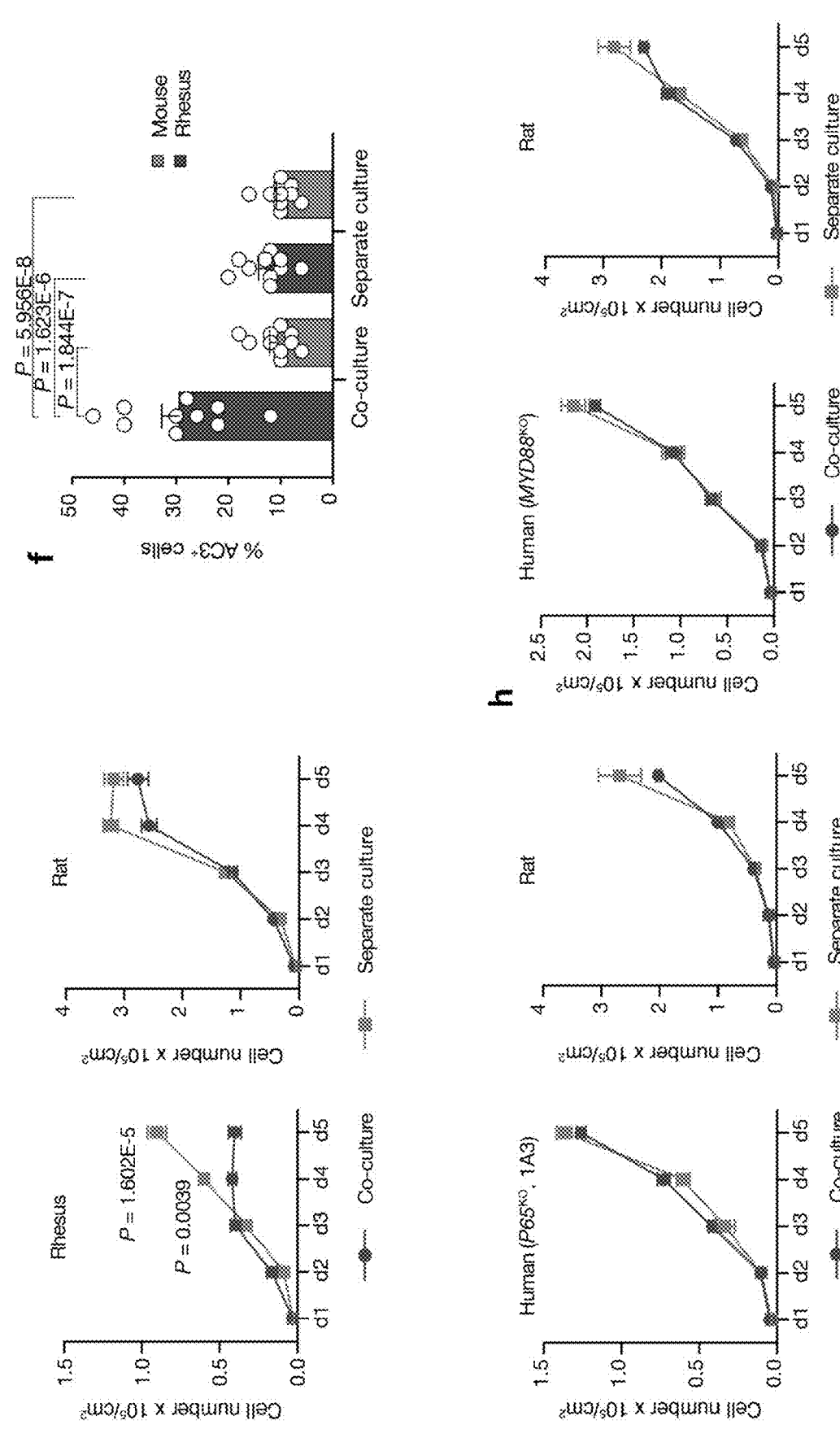
Figure 13:
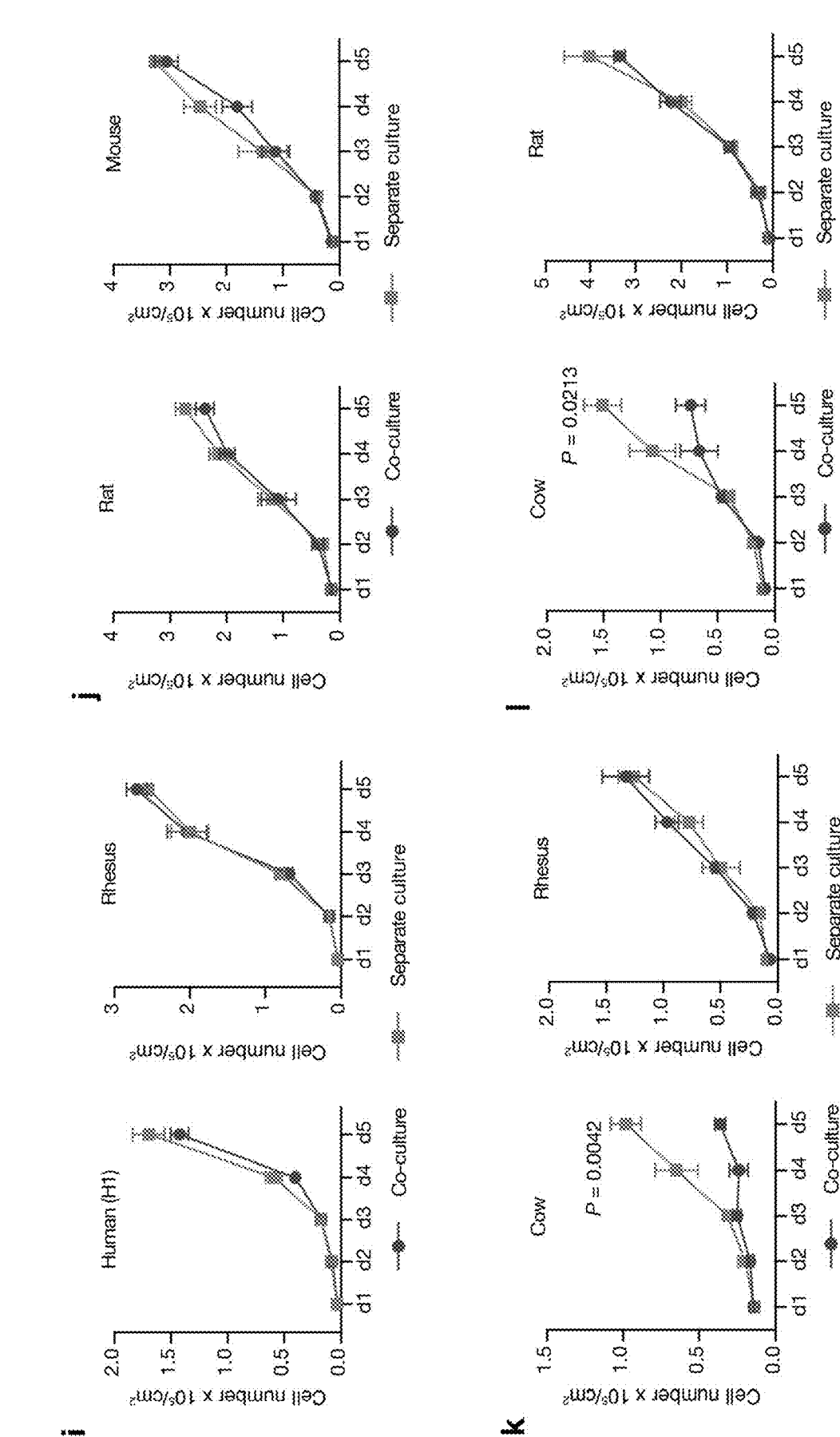

FIG. 13 panels a-l show primed PSC competition among different species. a, Representative brightfield images showing the derivation of rEpiSCs under the FR condition. Left, an isolated E7.5 Sprague Dawley rat epiblast; middle, day 2 rat epiblast outgrowth; right, rEpiSCs at passage 11. Scale bars, left, 200 μm; middle and right, 100 μm. b, Representative brightfield images showing typical colony morphologies of rEpiSCs, rhESCs (ORMES23) and bESCs grown in the FR condition, Scale bar, 200 μm; c, Representative immunofluorescence images showing long term FR-cultured rEpiSCs, ORMES23 rhESCs and bESCs expressed pluripotency transcription factors SOX2 and OCT4. DAPI. Scale bars, 200 μm. d, Growth curves of H1 hESCs and rEpiSCs over 5 days in separate (squares) and co-culture (circles). Plating ratio=4:1 (human:rat). n=3, biological replicates, mean±s.e.m. *P<0.05, P<0.01. e, Growth curves of ORMES23 rhESCs and rEpiSCs over 5 days in separate (squares) and co-culture (circles). Plating ratio=4:1 (rhesus: rat). n=3, biological replicates, mean±s.e.m. P<0.01, *P<0.001.f. Quantification of apoptotic cells by counting AC3$^{+}$ cells of day 3 co-cultured and separately cultured ORMES23 rhESCs (first and third bars) and mEpiSCs (second and fourth bars), n=10, 10 randomly selected fields (318.2×318.2 μm$^2$ each) from three independent immunostaining experiments per sample, mean±s.e.m. *P<0.001. g, Growth curves of P65$^{KO}$-hiPSCs (clone #1B1) and rEpiSCs over 5 days in separate (squares) and co-culture (circles). n=3, biological replicates, mean±s.e.m. h, Growth curves of MYD88$^{KO}$-hiPSCs and rEpiSCs over 5 days in separate (squares) and co-culture (circles). n=3, biological replicates, mean±s.e.m. i, Growth curves of H1 hESCs and ORMES23 rhESCs over 5 days in separate (squares) and co-culture (circles). Plating ratio=1:1 (rhesus:human). n=3, biological replicates, mean±s.e.m. j, Growth curves of mEpiSCs and rEpiSCs over 5 days in separate (squares) and co-culture (circles). Plating ratio=1:1 (mouse: rat). n=3, biological replicates, mean±s.e.m. k, Growth curves of bESCs and ORMES23 rhESCs over 5 days in separate (squares) and co-culture (circles). Plating ratio=1:1 (cow: rhesus). n=3, biological replicates, mean±s.e.m. **P<0.01. l, Growth curves of bESCs and rEpiSCs over 5 days in separate (squares) and co-culture (circles). Plating ratio=4:1 (cow:rat). n=3, biological replicates, mean±s.e.m. *P<0.05.

Figure 14:
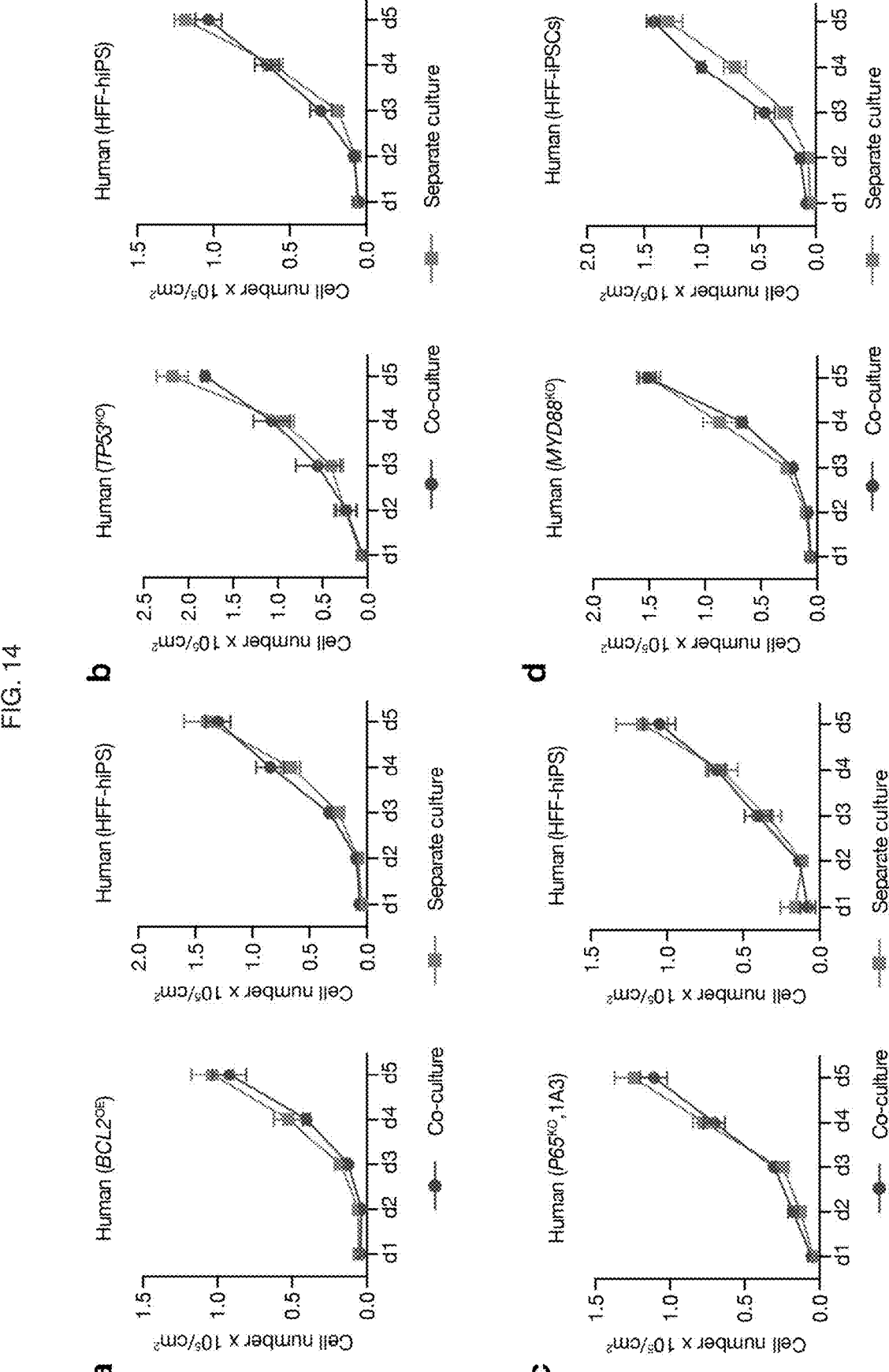
Figure 14:
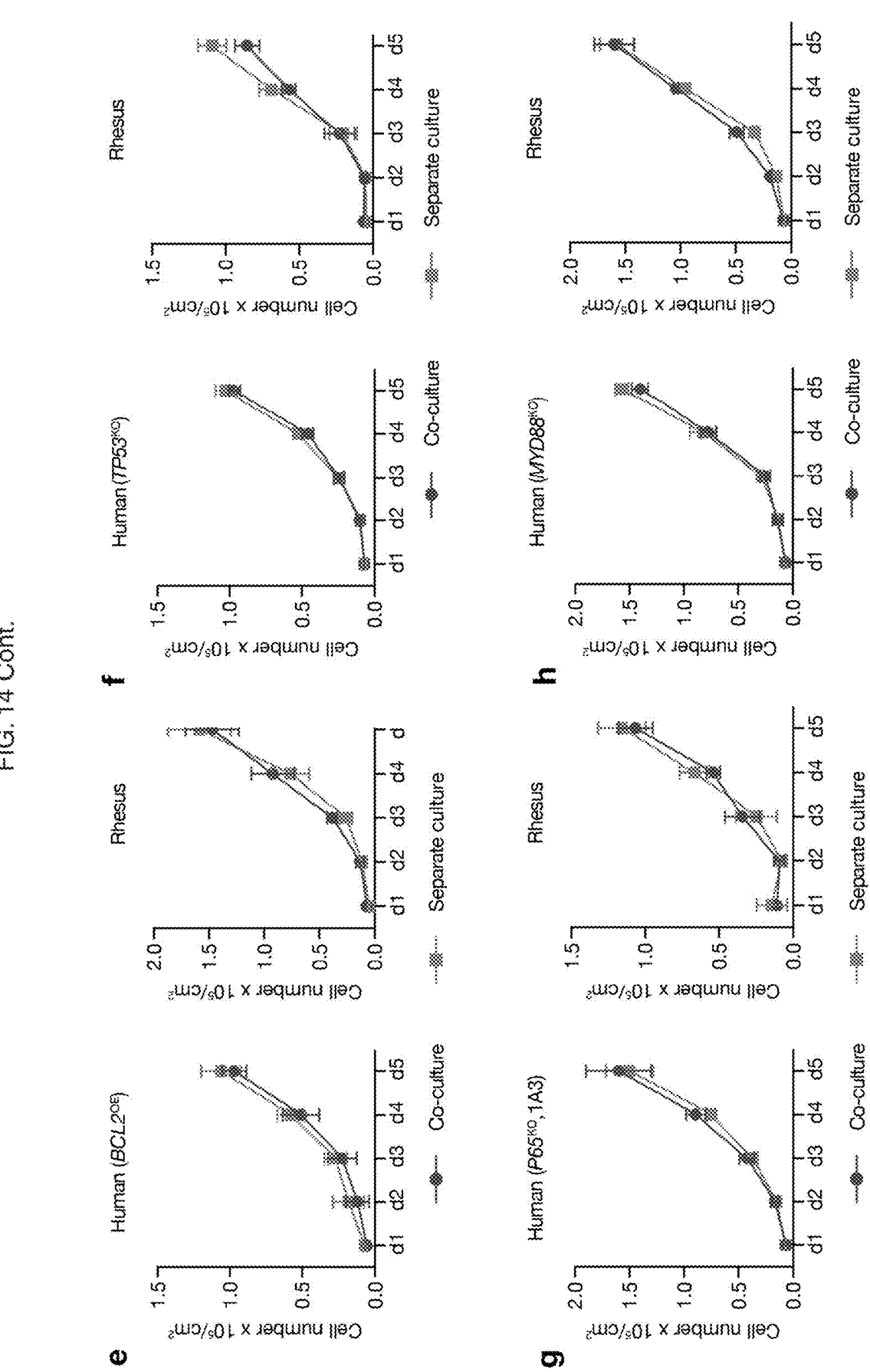
Figure 14:
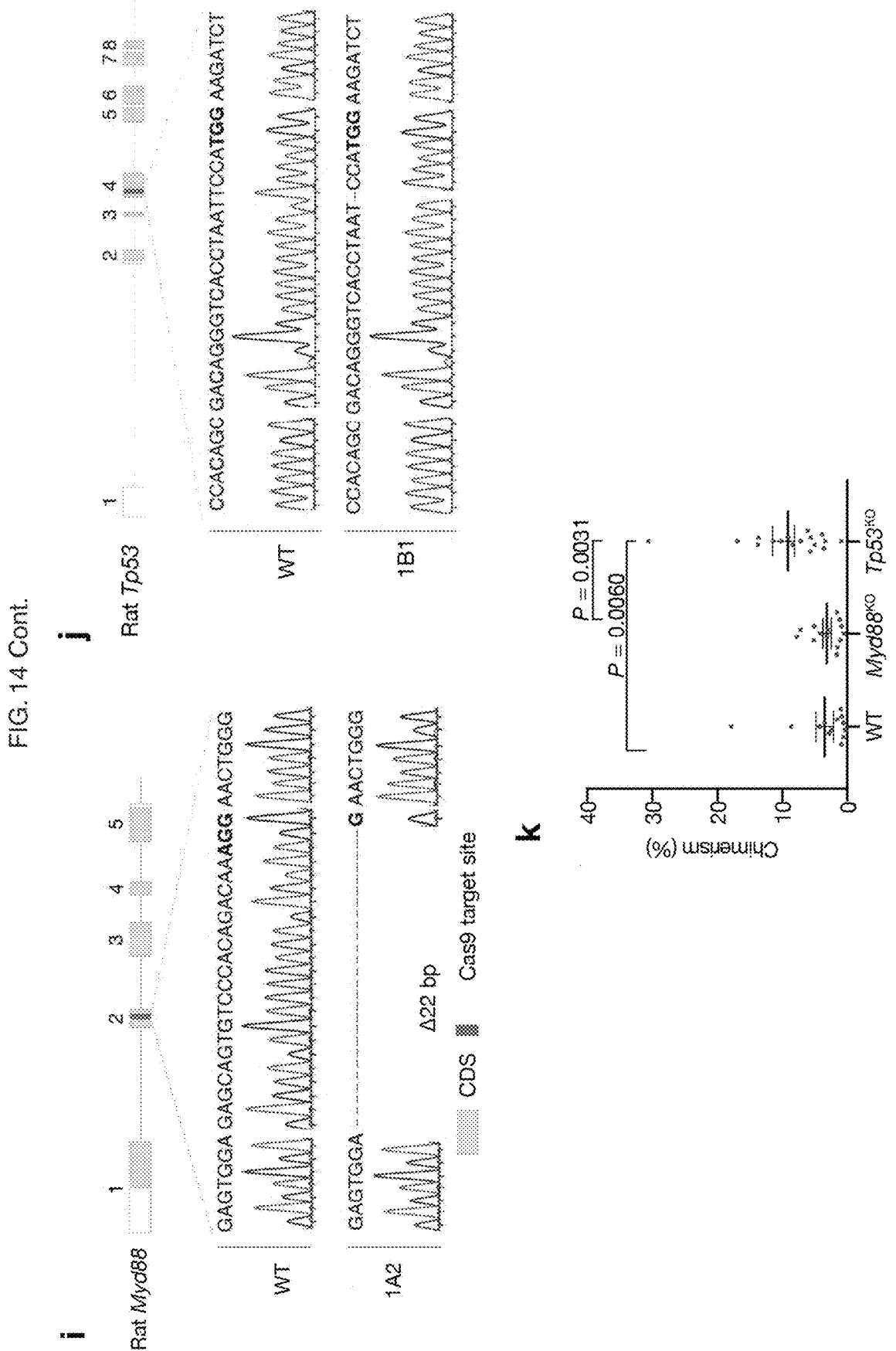

FIG. 14 panels a-k show that genetic perturbation of MYD88, TP53 or P65, and BCL2 overexpression didn't confer HFF-hiPSCs with the super competitor status. a, Growth curves of WT- and BCL-2$^{OE}$-iPSCs over 5 days in separate (squares) and co-culture (circles). n=3, biological replicates, mean±s.e.m. b, Growth curves of and WT- and TP53$^{KO}$-iPSCs over 5 days in separate (squares) and co-culture (circles). n=3, biological replicates, mean±s.e.m. c, Growth curves of WT- and P65$^{KO}$-iPSCs over 5 days in separate (squares) and co-culture (circles). n=3, biological replicates, mean±s.e.m. d, Growth curves of WT- and MYD88$^{KO}$-iPSCs over 5 days in separate (squares) and co-culture (circles). n=3, biological replicates, mean±s.e.m. e, Growth curves of BCL-2$^{OE}$-hiPSCs and ORMES23 rhESCs over 5 days in separate (squares) and co-culture (circles). n=3, biological replicates, mean±s.e.m. f, Growth curves of TP53$^{KO}$-hiPSCs and ORMES23 rhESCs over 5 days in separate (squares) and co-culture (circles). n=3, biological replicates, mean±s.e.m. j, Growth curves of P65$^{KO}$-hiPSCs and ORMES23 rhESCs over 5 days in separate (squares) and co-culture (circles). n=3, biological replicates, mean±s.e.m. h, Growth curves of MYD88$^{KO}$-hiPSCs and ORMES23 rhESCs over 5 days in separate (squares) and co-culture (circles). n=3, biological replicates, mean±s.e.m. i, Sanger sequencing result showing out-of-frame homozygous "22 bp" deletion mutation in MYD88$^{KO}$ rat ESCs. GAGTGGAGAGCAGTGTCCCACA-GACAAAGGAACTGGG is SEQ ID NO:50; GAGTG-GAGAACTGGG is SEQ ID NO:51. j, Sanger sequencing result showing out-of-frame homozygous "1 bp" deletion mutation in Tp53$^{KO}$ rat ESCs. CCACAGCGACAGGGT-CACCTAATTCCATGGAAGATCT is SEQ ID NO:52; CCACAGCGACAGGGTCACCTAATCCATGGAA-GATCT is SEQ ID NO:53. k, Dot plot showing the chimeric contribution levels of WT, MYD88$^{KO}$ and Tp53$^{KO}$ rat ESCs in E10.5 mouse embryos. Each dot indicates one E10.5 embryo. n=13 (WT), 14 (Myd88 KO), and 17 (Tp53 KO), biological replicates, mean±s.e.m. *P<0.05.

DETAILED DESCRIPTION OF THE INVENTION

Chimeric Blastocysts

Interspecies blastocyst complementation holds potential to overcome interspecies chimerism barriers. For interspecies blastocyst complementation, PSCs from one species are injected into a blastocyst, e.g. an organogenesis disabled blastocyst, of another species. The blastocyst can provide an emptied "developmental niche" for the donor PSCs to enrich in a specific organ during development. In an embodiment modulation of the TLR/NF-kB and/or p53 signaling pathways in donor pluripotent cells provides for the development of interspecies chimerism.

A chimeric blastocyst can comprise, for example, (i) a host blastocyst from a first mammalian species; and (ii) donor pluripotent stem cells from a second mammalian species, wherein the donor pluripotent stem cells have reduced expression or reduced biological activity of one or more proteins in the TLR/NF-kB signaling pathway or the p53 pathway.

A blastocyst or blastula is a structure formed in early mammalian development that includes an inner cell mass that eventually gives rise to the embryo. Surrounding the inner cell mass and the fluid-filled cavity known as the blastocoel is the trophoblast that gives rise to the placenta.

A chimeric blastocyst is a blastocyst that comprises cells from at least two different mammalian species. As used herein, the percentage of chimerism refers to the ratio of cells between the second mammalian species and the first mammalian species. In some embodiments, the percentage of chimerism is less than 40%, less than 30%, less than 20%, less than 10%, less than 5%, less than 1%, less than 0.5%, less than 0.1%, and any number or range in between. In some embodiments, the percentage of chimerism is more than 0.1%, more than 0.5%, more than 1%, more than 5%, more than 10%, more than 20%, more than 30%, more than 40%, and any number or range in between.

Compositions described herein can comprise a host blastocyst from a first mammalian species. A host blastocyst can provide a developmental niche for donor pluripotent stem cells. A host blastocyst can be an organogenesis disabled blastocyst or a wild-type blastocyst. An organogenesis disabled blastocyst is a blastocyst that is incapable of giving rise to one or more organs. Thus, an organogenesis disabled host blastocyst can provide an emptied developmental niche for donor pluripotent stem cells. The organogenesis disabled blastocyst is a mutant blastocyst.

An organogenesis disabled blastocyst can comprise a genetic deficiency. The genetic deficiency of the host blastocyst can occur in host pluripotent stem cells. The host blastocyst can have any genetic deficiency that results in a deficiency to give rise to one or more organs. The genetic deficiency can be, for example, in one or more genes selected from Foxa1, Foxa2, Gata4, Gata6, Hnf1a, Hnf1b, Hnf4a, Hhex, Prox1, Tbx3, Hnf6, Anln, Sek1, FAH, Nkx2.5, Tbx5, Mef2c, Isl1, Tbx1, Osr1, Lhx1, Pax2, Pax8, Wt1, Foxd1, Hox11a, Hox11b, Hox11c, Eya1, Six1, Six2, Wnt4, Fgf8, Bmp7, Notch2, Pod1, Pdgfr, Sal11, Etv2, Trox1, Ronx-1, Scl/Tal-1, Lmo-2, Tel, Tek, Sox9, Scleraxis, Pax6, Rx, Pdx1, Nkx2.1, Foxf1, and combinations thereof. An organogenesis disabled blastocyst can be deficient in the ability to give rise to any organ or tissue, including any organ or tissue for transplantation. Accordingly, the organogenesis disabled blastocyst can be deficient in giving rise to stem cells of any organ or tissue. An organogenesis disabled blastocyst is unable to give rise to, for example, heart, kidney, liver, lung, pancreas, intestine, uterus, thymus, spleen, hematopoietic tissue, bone marrow, blood, musculoskeletal tissues, bone, tendons, ligaments, cornea, eye, skin, heart valves, nerves, neuronal tissue, spinal cord, blood vessels, veins, arteries, bladder and lymphatic vessels, for example, and/or any stem cells of the foregoing organs and tissues.

In some embodiments, the host blastocyst can give rise to any organ or tissue, i.e., the host blastocyst is not organogenesis disabled. Thus, the host blastocyst can be a wild-type blastocyst. A wild-type blastocyst can give rise to any organ or tissue, including heart, kidney, liver, lung, pancreas, intestine, uterus, thymus, spleen, hematopoietic tissue, bone marrow, blood, musculoskeletal tissues, bone, tendons, ligaments, cornea, eye, skin, heart valves, nerves, neuronal tissue, spinal cord, blood vessels, veins, arteries, bladder and lymphatic vessels, for example, and/or any stem cells of the foregoing organs and tissues.

Generally, host cells from a first mammalian species comprise a greater percentage of the chimeric blastocyst than donor pluripotent stem cells (donor PSCs) from a second mammalian species. Host cells from a first mammalian species can comprise, for example, more than 50%, more than 60%, more than 70%, more than 80%, more than 90%, more than 95%, more than 96%, more than 97%, more than 98%, more than 99%, more than 99.5%, and any number or range in between, of the chimeric blastocyte. The percentage of donor PSCs from a second mammalian species can comprise, for example, less than 50%, less than 40%, less than 30%, less than 20%, less than 10%, less than 5%, less than 4%, less than 3%, less than 2%, less than 1%, less than 0.5%, and any number or range in between, of the chimeric blastocyst. A person skilled in the art will appreciate that the percentage of cells contributed by the host blastocyst from a first mammalian species and the percentage of donor PSCs can change during the course of development in accordance with developmental stage and organ or tissue development.

Donor pluripotent stem cells (donor PSCs) can be obtained from a second mammalian species. Donor PSCs can enrich in a specific organ during development. Donor PSCs can give rise to any organ or tissue, including organs and tissues for transplantation. Exemplary organs and tissues include heart, kidney, liver, lung, pancreas, intestine, uterus, thymus, spleen, hematopoietic tissue, bone marrow, blood, musculoskeletal tissues, bone, tendons, ligaments, cornea, eye, skin, heart valves, nerves, neuronal tissue, spinal cord, blood vessels, veins, arteries, bladder and lymphatic vessels, and/or any stem cells thereof.

Any type of donor PSC can contribute to chimeric blastocyst formation. For example, donor PSCs can comprise embryonic stem cells derived from embryos. Such cells are generally referred to as "ES cells." Donor PSCs can comprise parthenogenesis embryonic stem cells (pES cells), i.e., embryonic stem cells derived from unfertilized eggs. Donor PSCs comprise embryonic stem cells prepared by somatic cell nuclear transfer (ntES cells). Donor PSCs can comprise induced pluripotent stem cells (iPSCs) prepared from somatic cells by cellular reprogramming. Any cell type can be used to generate iPSCs, including, for example, fibroblasts, keratinocytes, blood cells, epithelial cells, including renal epithelial cells, for example, and others. Any combination of reprogramming factors can be used, including transcription factors such as Oct3/4, Nanog, Glis1, the mRNA binding protein Lin28, and members of the Sox, Klf, and Myc families of transcription factors. For example, for reprogramming of human fibroblasts, Oct4, Sox2, cMyc, and Klf4 or Oct4, Sox2, Nanog, and Lin 28 can be used. Additional methods of making iPSCs are described in U.S. Patent Publication 20170283777, which is incorporated herein by reference in its entirety.

A chimeric blastocyst can comprise a host blastocyst from a first mammalian species and donor PSCs from a second mammalian species. Any mammalian species can be selected as a source of host blastocysts or a source of donor PSCs. Exemplary mammalian species that can be used as a source of host blastocysts or a source of donor PSCs include, for example, any species selected from the order Artiodactyla (even-toed hoofed animals) of infra-order Ungulata, the order Carnivora (meat-eaters), the order Cetacea (whales and porpoises), the order Chiroptera (bats), the order Dermoptera (colugos or flying lemurs), the order Edentata (toothless mammals), the order Hyracoidae (hyraxes, dassies), the order Insectivora (insect-eaters), the order Lagomorpha (pikas, hares, and rabbits), the order Marsupialia (pouched animals), the order Monotremata (egg-laying mammals), the order Perissodactyla (odd-toed hoofed animals) of infra-order Ungulata, the order Pholidata, the order Pinnipedia (seals and walruses), the order Primates (primates), the order Proboscidea (elephants), the order Rodentia (gnawing mammals), the order Sirenia (dugongs and manatees), or the order Tubulidentata (aardvarks).

The first mammalian species and the second mammalian species can be different species. The first mammalian species can be a non-primate species. The first mammalian species can be a species of the order Artiodactyla, the order Carnivora, the order Lagomorpha, the order Perissodactyla, or the order Rodentia. The first mammalian species can be a rodent or an ungulate. The ungulate can be a species of the family Suidae. The first mammalian species can be a mouse, a rat, a pig, a cow, a sheep, a horse, a camel, a deer, a rhinoceros, an elephant, a giraffe, or a hippopotamus.

The second mammalian species can be, for example, a primate, a human, a monkey, a baboon, a bonobo, a gorilla, or a chimpanzee.

Genetic Modification of Donor Pluripotent Stem Cells (Donor PSCs)

Donor pluripotent stem cells (donor PSCs) of a chimeric blastocyst can have reduced expression, reduced biological activity, or reduced enzymatic activity of one or more proteins in the TLR/NF-kB signaling pathway or the p53 pathway. All TLR signa activation of the transcription factor-kappaB (NF-kB), which controls the expression of an array of inflammatory cytokine genes. The p53 tumor suppressor protein serves as a genome guardian and functions mainly as a transcription factor by binding to specific DNA sequences and by transactivating or repressing a large group of target genes. These downstream targets of p53 regulate the pathways of cell cycle arrest, apoptosis, and DNA repair to maintain a dynamic equilibrium between cell growth and arrest in response to factors including DNA damage, hypoxia (oxygen deprivation), and a deficiency of growth factors or nutrients.

Any protein in the TLR/NF-kB signaling pathway or the p53 pathway can have reduced expression and/or reduced biological activity in donor PSCs. The one or more proteins in the TLR/NF-kB signaling pathway or the p53 pathway can be, for example, IL-1R1, TLR1, TLR2, TLR3, TLR4, TLR5, TLR6, TLR7, TLR8, TLR9, TLR10, TIRAP, TRAM, MAL, SARM, MYD88, IRAK1, IRAK4, TRAF6, TAK1, TAB1, TAB2, TAB3, IKK1, IKK2, NEMO, IkBa, TRIF, RIP1, TRAF3, TBK1, IKKi, IRF3, P65, P50, TP53, or combinations thereof. Exemplary proteins in the TLR/NF-kB signaling pathway include IL-1R1, TLR1, TLR2, TLR3, TLR4, TLR5, TLR6, TLR7, TLR8, TLR9, TLR10, TIRAP, TRAM, MAL, SARM, MYD88, IRAK1, IRAK4, TRAF6, TAK1, TAB1, TAB2, TAB3, IKK1, IKK2, NEMO, IkBa, TRIF, RIP1, TRAF3, TBK1, IKKi, IRF3, P65, P50, and others. Exemplary proteins in the p53 pathway include TP53 and proteins that function in growth arrest, cell cycle arrest, apoptosis, senescence, DNA damage, DNA repair, metabolic regulation, responses to reactive oxygen species (ROS), autophagy, and miRNA regulation, among others. For proteins that are expressed as precursors, the term for the mature protein and the precursor are used interchangeably herein, unless context clearly indicates otherwise. For example, p50 can be produced from a p105 precursor by proteolytic processing. Thus, when referring to p50, reference is to the p105 precursor as well, and vice versa, unless context clearly indicates otherwise.

Reduced expression of a protein refers to diminished expression such that expression of the protein is reduced by 50%, 60%, 70%, 80%, 90%, 95%, 99% or more. In an embodiment, there is no expression of the protein. Reduced biological activity of a protein refers to diminished biological activity such that activity of the protein is reduced by 50%, 60%, 70%, 80%, 90%, 95%, 99% or more. In an embodiment, there is no biological activity of the protein. Reduced enzymatic activity of a protein refers to diminished enzymatic activity such that enzymatic activity of the protein is reduced by 50%, 60%, 70%, 80%, 90%, 95%, 99% or more. In an embodiment, there is no enzymatic activity of the protein.

Any method can be used to reduce expression of a protein, including knockdown by techniques such as shRNA, siRNA, miRNA, CRISPRi, dCas9-KRAB, CRISPR-Cas13, and antisense oligonucleotides, for example. Additional methods include promoter disruption, enhancer disruption, promoter and enhancer disruption or modification, gene knockout, and gene editing or gene modification, for example. In some embodiments, a gene modifying agent is used to reduce protein expression, such as Cre DNA recombinase, a TALEN, a zinc finger nuclease, a homing endonuclease, a targeted SPO11 nuclease, or a CRISPR-associated (Cas) reagent, for example. Alternatively, nucleic acids can be inserted into a gene to disrupt expression of a gene product. A gene can be disrupted such that any gene product lacks biological or enzymatic activity.

Promoter disruption and enhancer disruption refer to modification of a promoter or an enhancer so as to reduce the level of promoter or enhancer activity. Promoter and/or enhancer activity can be reduced by 50%, 60%, 70%, 80%, 90%, 95%, 99% or more. In some embodiments, there is no promoter activity, no enhancer activity, or both no promoter activity and no enhancer activity.

Donor PSCs can have reduced biological activity of one or more proteins in the TLR/NF-kB signaling pathway or the p53 pathway. Any of the methods described herein that can result in reduced protein expression can result in reduced biological activity or reduced enzymatic activity. In some embodiments, partial gene disruption results in an altered protein with reduced biological activity. In some embodiments, reduced biological activity of one or more proteins in the TLR/NF-kB signaling pathway or the p53 pathway results from reduced expression of one or more proteins in the TLR/NF-kB signaling pathway or the p53 pathway. In some embodiments, the presence of a dominant negative protein can reduce protein activity. Any method can be used to introduce a dominant negative protein, including transient and stable transfection, for example.

Any vector can be used to introduce agents that reduce protein expression or biological activity of a protein. A vector is a macromolecule or association of macromolecules that comprises or associates with a nucleic acid molecule or a polynucleotide and that can be used to mediate delivery of the nucleic acid molecule or polynucleotide to a cell. Examples of vectors include plasmids, viral vectors, phages, cosmids, liposomes, and other gene delivery vehicles. Examples of viral vectors include retroviral vectors, lentiviral vectors, adenoviral vectors, adeno-associated virus (AAV) vectors, flaviviral vectors, and others. AAV vectors used in the compositions and methods described herein can be of any serotype (e.g., AAV1, AAV2, AAV3, AAV4, AAV5, AAV6, AAV7, AAV8, AAV9, and AAVDJ), including hybrid or chimeric AAV serotypes. A vector generally comprises genetic elements, e.g., regulatory elements, operatively linked to a transgene or heterologous gene to facilitate expression of the transgene or heterologous gene in a target. A vector can comprise one or more elements for vector replication. A vector can be engineered to lack one or more elements for vector replication.

Donor PSCs can be genetically deficient in one or more cellular factors that limit proliferation and/or survival of the donor PSCs in the presence of host pluripotent stem cells (host PSCs) relative to proliferation and/or survival of the host PSCs. A cellular factor is any component of a cell, including a protein, a RNA, a lipid, or a carbohydrate, for example. In some embodiments, donor PSCs are genetically deficient in one or more proteins in the TLR/NF-kB signaling pathway or the p53 pathway. Genetic deficiency in a cellular factor or in one or more proteins in the TLR/NF-kB signaling pathway or the p53 pathway can result in reduced cellular factor or protein expression and/or reduced biological activity of the factor or protein. Without being limited by theory, one or more proteins in the TLR/NF-kB signaling pathway or the p53 pathway can limit proliferation and/or survival of the donor PSCs in the presence of host PSCs relative to proliferation and/or survival of the host pluripotent stem cells. Thus, reduced expression and/or reduced activity of one or more proteins in the TLR/NF-kB signaling pathway or the p53 pathway can allow for proliferation and/or survival of donor PSCs in the presence of host PSCs without host PSCs outcompeting donor PSCs. In some embodiments, reduced expression and/or reduced activity of one or more proteins in the TLR/NF-kB signaling pathway or the p53 pathway decreases apoptosis of donor PSCs in the presence of host PSCs.

In an embodiment, genetically engineered or recombinant donor cells have attenuated expression of a polynucleotide encoding IL-1R1, TLR1, TLR2, TLR3, TLR4, TLR5, TLR6, TLR7, TLR8, TLR9, TLR10, TIRAP, TRAM, MAL, SARM, MYD88, IRAK1, IRAK4, TRAF6, TAK1, TAB1, TAB2, TAB3, IKK1, IKK2, NEMO, IkBa, TRIF, RIP1, TRAF3, TBK1, IKKi, IRF3, P65, P50, TP53, or combinations thereof. Attenuated means reduced in amount, degree, intensity, or strength. Attenuated gene or polynucleotide expression can refer to a reduced amount and/or rate of transcription of the gene or polynucleotide in question. As nonlimiting examples, an attenuated gene or polynucleotide can be a mutated or disrupted gene or polynucleotide (e.g., a gene or polynucleotide disrupted by partial or total deletion, truncation, frameshifting, or insertional mutation) or that has decreased expression due to alteration or disruption of gene regulatory elements. An attenuated gene can also be a gene targeted by a construct that reduces expression of the gene or polynucleotide, such as, for example, an antisense RNA, microRNA, RNAi molecule, or ribozyme.

Attenuate also means to weaken, reduce, or diminish the biological activity of a gene product or the amount of a gene product expressed (e.g., p65, MYD88, TRIF, TP53, p50, IKK1, IKK2, NEMO proteins) via, for example a decrease in translation, folding, or assembly of the protein. In an embodiment attenuation of a gene product (e.g., a p65, MYD88, TRIF, TP53, p50, IKK1, IKK2, NEMO protein) means that the gene product is expressed at a rate or amount about 5, 10, 20, 30, 40, 50, 60, 70, 80, 90, 95, or 99% less (or any range between about 5 and 99% less; about 5 and 95% less; about 20 and 50% less, about 10 and 40% less, or about 10 and 90% less) than occurs in a wild-type or control organism. In an embodiment, attenuation of a gene product (e.g., p65, MYD88, TRIF, TP53, p50, IKK1, IKK2, NEMO) means that the biological activity of the gene product is about 5, 10, 20, 30, 40, 50, 60, 70, 80, 90, 95, or 99% less (or any range between about 5 and 99% less; about 5 and 95% less, about 10 and 90% less) than occurs in a wild-type or control organism.

p65 is a subunit of the NF-kB heterodimer, which is a transcription factor complex.

MYD88 functions as an adapter in cell signaling in innate immunity.

TRIF functions as an adapter in responding to activation of Toll-like receptors (TLRs).

TP53 binds to DNA and prevents mutation of the genome, thus functioning as a tumor suppressor.

p50 is a subunit of the NF-kB heterodimer, which is a transcription factor complex.

IKK1 phosphorylates IκBα as a subunit of the IkB kinase complex.

IKK2 phosphorylates IκBα as a subunit of the IkB kinase complex.

NEMO is a subunit of the IkB kinase complex.

IL-1R1 is an interleukin 1 receptor, type I. It is a receptor for interleukin 1 alpha (IL1A), interleukin 1 beta (IL1B), and interleukin 1 receptor antagonist (IL1RA). It is an important mediator involved in many cytokine induced immune and inflammatory responses.

TLR1 is a member of the toll-like receptor (TLR) family and plays a role in pathogen recognition and activation of innate immunity. TLR1 can form a heterodimer with TLR2 as part of the innate immune system.

TLR2 is a member of the toll-like receptor (TLR) family and plays a role in pathogen recognition and activation of innate immunity. TLR2 is a membrane receptor, which is expressed on the surface of certain cells and recognizes foreign substances and passes on appropriate signals to the cells of the immune system.

TLR3 is a member of the toll-like receptor (TLR) family and plays a role in pathogen recognition and activation of innate immunity.

TLR4 is a transmembrane protein. Its activation leads to an intracellular signaling pathway TLR/NF-κB and inflammatory cytokine production which is responsible for activating the innate immune system.

TLR5 is a member of the toll-like receptor (TLR) family. TLR5 is known to recognize bacterial flagellin from invading mobile bacteria.

TLR6 is a transmembrane protein, member of toll-like receptor family, which belongs to the pattern recognition receptor (PRR) family. TLR6 acts in a heterodimer form with toll-like receptor 2 (TLR2). Its ligands include multiple diacyl lipopeptides derived from gram-positive bacteria and mycoplasma and several fungal cell wall saccharides. After dimerizing with TLR2, the TLR/NF-κB intracellular signaling pathway is activated, leading to a pro-inflammatory cytokine production and activation of innate immune response.

TLR7 is a member of the toll-like receptor (TLR) family. TLR7 recognizes single-stranded RNA in endosomes, which is a common feature of viral genomes which are internalized by macrophages and dendritic cells.

TLR8 is a member of the toll-like receptor (TLR) family and plays a role in pathogen recognition and activation of innate immunity.

TLR9 is a member of the toll-like receptor (TLR) family and plays a role in pathogen recognition and activation of innate immunity. TLR9 is an important receptor expressed in immune system cells including dendritic cells, macrophages, natural killer cells, and other antigen presenting cells. TLR9 preferentially binds DNA present in bacteria and viruses, and triggers signaling cascades that lead to a pro-inflammatory cytokine response TLR10 is a member of the toll-like receptor (TLR) family and plays a role in pathogen recognition and activation of innate immunity.

TIRAP is an adapter molecule associated with toll-like receptors. The innate immune system recognizes microbial pathogens through Toll-like receptors (TLRs), which identify pathogen-associated molecular patterns.

TRAM is a multi-pass membrane protein involved in protein insertion into the ER membrane.

MAL is a highly hydrophobic integral membrane protein.

SARM is a toll-like receptor adaptor.

IRAK1 is a serine/threonine-protein kinase that plays a critical role in initiating innate immune response against foreign pathogens. IRAK1 is involved in Toll-like receptor (TLR) and IL-1R signaling pathways. It is rapidly recruited by MYD88 to the receptor-signaling complex upon TLR activation. Association with MYD88 leads to IRAK1 phosphorylation by IRAK4 and subsequent autophosphorylation and kinase activation IRAK4 is in the IRAK family, is a protein kinase involved in signaling innate immune responses from Toll-like receptors.

TRAF6 is a member of the TNF receptor associated factor (TRAF) protein family. TRAF proteins are associated with, and mediate signal transduction from members of the TNF receptor superfamily. This protein mediates the signaling not only from the members of the TNF receptor superfamily, but also from the members of the Toll/IL-1 family.

TAK1 is a member of the serine/threonine protein kinase family. This kinase mediates signal transduction induced by TGF beta and morphogenetic protein (BMP) and controls a variety of cell functions including transcription regulation and apoptosis. TAK1 is a central regulator of cell death and is activated through a diverse set of intra- and extracellular stimuli.

TAB1 may be an important signaling intermediate between TGFB receptors and MAP3K7/TAK1.

TAB2 is an activator of MAP3K7/TAK1, which is required for the IL-1 induced activation of nuclear factor kappaB and MAPK8/JNK. This protein forms a kinase complex with TRAF6, MAP3K7 and TAB1, and it thus serves as an adaptor that links MAP3K7 and TRAF6.

TAB3 functions in the TLR/NF-kB signal transduction pathway.

IkBa is one member of a family of cellular proteins that function to inhibit the NF-κB transcription factor. IκBα inhibits NF-κB by masking the nuclear localization signals (NLS) of NF-κB proteins and keeping them sequestered in an inactive state in the cytoplasm.

RIP1 functions in a variety of cellular pathways related to both cell survival and death. In terms of cell death, RIPK1 plays a role in apoptosis and necroptosis. Some of the cell survival pathways RIPK1 participates in include TLR/NF-κB, Akt, and JNK.

TRAF3 is a member of the TNF receptor associated factor (TRAF) protein family. TRAF proteins associate with, and mediate the signal transduction from, members of the TNF receptor (TNFR) superfamily.

TBK1 is an enzyme with kinase activity. Specifically, it is a serine/threonine protein kinase. TBK1 plats a role in innate immunity antiviral response.

IKKi is a serine/threonine kinase that plays an essential role in regulating inflammatory responses to viral infection, through the activation of the type I IFN, TLR/NF-kB and STAT signaling. Also involved in TNFA and inflammatory cytokines, like Interleukin-1, signaling.

IRF3 F3 is a member of the interferon regulatory transcription factor (IRF) family.

Genetically engineered or recombinant donor cells can express a polynucleotide encoding a p65 polypeptide, a MYD88 polypeptide, a TRIF polypeptide, a TP53 polypeptide, a p50 polypeptide, an IKK1 polypeptide, an IKK2 polypeptide, a NEMO polypeptide, an IL-1R1 polypeptide, a TLR1 polypeptide, a TLR2 polypeptide, a TLR3 polypeptide, a TLR4 polypeptide, a TLR5 polypeptide, a TLR6 polypeptide, a TLR7 polypeptide, a TLR8 polypeptide, a TLR9 polypeptide, a TLR10 polypeptide, a TIRAP polypeptide, a TRAM polypeptide, a MAL polypeptide, a SARM polypeptide, an IRAK1 polypeptide, an IRAK4 polypeptide, a TRAF6 polypeptide, a TAK1 polypeptide, a TAB1 polypeptide, a TAB2 polypeptide, a TAB3 polypeptide, an IkBa polypeptide, a RIP1 polypeptide, a TRAF3 polypeptide, a TBK1 polypeptide, an IKKi polypeptide, an IRF3 polypeptide, or combinations thereof at an attenuated rate or amount (e.g., amount and/or rate of transcription of the gene or polynucleotide). An attenuated rate or amount is about 5, 10, 20, 30, 40, 50, 60, 70, 80, 90, 95, 99% less than the rate of a wild-type or control donor cells. The result of attenuated expression of a polynucleotide encoding a p65 polypeptide, a MYD88 polypeptide, a TRIF polypeptide, a TP53 polypeptide, a p50 polypeptide, an IKK1 polypeptide, an IKK2 polypeptide, a NEMO polypeptide, an IL-1R1 polypeptide, a TLR1 polypeptide, a TLR2 polypeptide, a TLR3 polypeptide, a TLR4 polypeptide, a TLR5 polypeptide, a TLR6 polypeptide, a TLR7 polypeptide, a TLR8 polypeptide, a TLR9 polypeptide, a TLR10 polypeptide, a TIRAP polypeptide, a TRAM polypeptide, a MAL polypeptide, a SARM polypeptide, an IRAK1 polypeptide, an IRAK4 polypeptide, a TRAF6 polypeptide, a TAK1 polypeptide, a TAB1 polypeptide, a TAB2 polypeptide, a TAB3 polypeptide, an IkBa polypeptide, a RIP1 polypeptide, a TRAF3 polypeptide, a TBK1 polypeptide, an IKKi polypeptide, an IRF3 polypeptide, or combinations thereof is attenuated expression of a p65 polypeptide, a MYD88 polypeptide, a TRIF polypeptide, a TP53 polypeptide, a p50 polypeptide, an IKK1 polypeptide, an IKK2 polypeptide, a NEMO polypeptide, an IL-1R1 polypeptide, a TLR1 polypeptide, a TLR2 polypeptide, a TLR3 polypeptide, a TLR4 polypeptide, a TLR5 polypeptide, a TLR6 polypeptide, a TLR7 polypeptide, a TLR8 polypeptide, a TLR9 polypeptide, a TLR10 polypeptide, a TIRAP polypeptide, a TRAM polypeptide, a MAL polypeptide, a SARM polypeptide, an IRAK1 polypeptide, an IRAK4 polypeptide, a TRAF6 polypeptide, a TAK1 polypeptide, a TAB1 polypeptide, a TAB2 polypeptide, a TAB3 polypeptide, an IkBa polypeptide, a RIP1 polypeptide, a TRAF3 polypeptide, a TBK1 polypeptide, an IKKi polypeptide, or an IRF3 polypeptide.

Attenuated expression requires at least some expression of a biologically active wild-type or mutated p65 polypeptide, wild-type or mutated MYD88 polypeptide, wild-type or mutated TRIF polypeptide, wild-type or mutated TP53 polypeptide, wild-type or mutated p50 polypeptide, wild-type or mutated IKK1 polypeptide, wild-type or mutated IKK2 polypeptide, wild-type or mutated NEMO polypeptide, wild-type or mutated IL-1R1 polypeptide, wild-type or mutated TLR1 polypeptide, wild-type or mutated TLR2 polypeptide, wild-type or mutated TLR3 polypeptide, wild-type or mutated TLR4 polypeptide, wild-type or mutated TLR5 polypeptide, wild-type or mutated TLR6 polypeptide, wild-type or mutated TLR7 polypeptide, wild-type or mutated TLR8 polypeptide, wild-type or mutated TLR9 polypeptide, wild-type or mutated TLR10 polypeptide, wild-type or mutated TIRAP polypeptide, wild-type or mutated TRAM polypeptide, wild-type or mutated MAL polypeptide, wild-type or mutated SARM polypeptide, wild-type or mutated IRAK1 polypeptide, wild-type or mutated IRAK4 polypeptide, wild-type or mutated TRAF6 polypeptide, wild-type or mutated TAK1 polypeptide, wild-type or mutated TAB1 polypeptide, wild-type or mutated TAB2 polypeptide, wild-type or mutated TAB3 polypeptide, wild-type or mutated IkBa polypeptide, wild-type or mutated RIP1 polypeptide, wild-type or mutated TRAF3 polypeptide, wild-type or mutated TBK1 polypeptide, wild-type or mutated IKKi polypeptide, wild-type or mutated IRF3 polypeptide, or combinations thereof.

Deleted or null gene or polynucleotide expression can be gene or polynucleotide expression that is eliminated, for example, reduced to an amount that is insignificant or undetectable. Deleted or null gene or polynucleotide expression can also be gene or polynucleotide expression that results in an RNA or protein that is nonfunctional, for example, deleted gene or polynucleotide expression can be gene or polynucleotide expression that results in a truncated RNA and/or polypeptide that has substantially no biological activity.

Genetically engineered or recombinant donor cells can have no expression of a polynucleotide encoding a p65 polypeptide, a MYD88 polypeptide, a TRIF polypeptide, a TP53 polypeptide, a p50 polypeptide, an IKK1 polypeptide, an IKK2 polypeptide, or a NEMO polypeptide, or a combination thereof. The result is that substantially no p65 polypeptides, MYD88 polypeptides, TRIF polypeptides, TP53 polypeptides, p50 polypeptides, IKK1 polypeptides, IKK2 polypeptides, NEMO polypeptides, an IL-1R1 polypeptide, a TLR1 polypeptide, a TLR2 polypeptide, a TLR3 polypeptide, a TLR4 polypeptide, a TLR5 polypeptide, a TLR6 polypeptide, a TLR7 polypeptide, a TLR8 polypeptide, a TLR9 polypeptide, a TLR10 polypeptide, a TIRAP polypeptide, a TRAM polypeptide, a MAL polypeptide, a SARM polypeptide, an IRAK1 polypeptide, an IRAK4 polypeptide, a TRAF6 polypeptide, a TAK1 polypeptide, a TAB1 polypeptide, a TAB2 polypeptide, a TAB3 polypeptide, an IkBa polypeptide, a RIP1 polypeptide, a TRAF3 polypeptide, a TBK1 polypeptide, an IKKi polypeptide, an IRF3 polypeptide, or combinations are present in the donor cell.

The lack of expression can be caused by at least one gene disruption or mutation of a p65 gene, a MYD88 gene, a TRIF gene, a TP53 gene, a p50 gene, an IKK1 gene, an IKK2 gene, a NEMO gene, an IL-1R1 gene, a TLR1 gene, a TLR2 gene, a TLR3 gene, a TLR4 gene, a TLR5 gene, a TLR6 gene, a TLR7 gene, a TLR8 gene, a TLR9 gene, a TLR10 gene, a TIRAP gene, a TRAM gene, a MAL gene, a SARM gene, an IRAK1 gene, an IRAK4 gene, a TRAF6 gene, a TAK1 gene, a TAB1 gene, a TAB2 gene, a TAB3 gene, an IkBa gene, a RIP1 gene, a TRAF3 gene, a TBK1 gene, an IKKi gene, an IRF3 gene, or combinations thereof which results in no expression of the p65 gene, the MYD88 gene, the TRIF gene, the TP53 gene, the p50 gene, the IKK1 gene, the IKK2 gene, the NEMO gene, the IL-1R1 gene, the TLR1 gene, the TLR2 gene, the TLR3 gene, the TLR4 gene, the TLR5 gene, the TLR6 gene, the TLR7 gene, the TLR8 gene, the TLR9 gene, the TLR10 gene, the TIRAP gene, the TRAM gene, the MAL gene, the SARM gene, the IRAK1 gene, the IRAK4 gene, the TRAF6 gene, the TAK1 gene, the TAB1 gene, the TAB2 gene, the TAB3 gene, the IkBa gene, the RIP1 gene, the TRAF3 gene, the TBK1 gene, the IKKi gene, the IRF3 gene, or combinations thereof. For example, the lack of expression can be caused by a gene disruption in a p65 gene, a MYD88 gene, a TRIF gene, a TP53 gene, a p50 gene, an IKK1 gene, an IKK2 gene, a NEMO gene, an IL-1R1 gene, a TLR1 gene, a TLR2 gene, a TLR3 gene, a TLR4 gene, a TLR5 gene, a TLR6 gene, a TLR7 gene, a TLR8 gene, a TLR9 gene, a TLR10 gene, a TIRAP gene, a TRAM gene, a MAL gene, a SARM gene, an IRAK1 gene, an IRAK4 gene, a TRAF6 gene, a TAK1 gene, a TAB1 gene, a TAB2 gene, a TAB3 gene, an IkBa gene, a RIP1 gene, a TRAF3 gene, a TBK1 gene, an IKKi gene, or an IRF3 gene which results in attenuated expression of the p65 gene, the MYD88 gene, the TRIF gene, the TP53 gene, the p50 gene, the IKK1 gene, the IKK2 gene, the NEMO gene, the IL-1R1 gene, the TLR1 gene, the TLR2 gene, the TLR3 gene, the TLR4 gene, the TLR5 gene, the TLR6 gene, the TLR7 gene, the TLR8 gene, the TLR9 gene, the TLR10 gene, the TIRAP gene, the TRAM gene, the MAL gene, the SARM gene, the IRAK1 gene, the IRAK4 gene, the TRAF6 gene, the TAK1 gene, the TAB1 gene, the TAB2 gene, the TAB3 gene, the IkBa gene, the RIP1 gene, the TRAF3 gene, the TBK1 gene, the IKKi gene, or the IRF3 gene. Alternatively, a p65 gene, a MYD88 gene, a TRIF gene, a TP53 gene, a p50 gene, an IKK1 gene, an IKK2 gene, a NEMO gene, an IL-1R1 gene, a TLR1 gene, a TLR2 gene, a TLR3 gene, a TLR4 gene, a TLR5 gene, a TLR6 gene, a TLR7 gene, a TLR8 gene, a TLR9 gene, a TLR10 gene, a TIRAP gene, a TRAM gene, a MAL gene, a SARM gene, an IRAK1 gene, an IRAK4 gene, a TRAF6 gene, a TAK1 gene, a TAB1 gene, a TAB2 gene, a TAB3 gene, an IkBa gene, a RIP1 gene, a TRAF3 gene, a TBK1 gene, an IKKi gene, an IRF3 gene, or combinations thereof can be transcribed but not translated, or the genes can be transcribed and translated, but the resulting p65 polypeptide, MYD88 polypeptide, TRIF polypeptide, TP53 polypeptide, p50 polypeptide, IKK1 polypeptide, IKK2 polypeptide, NEMO polypeptide, IL-1R1 polypeptide, TLR1 polypeptide, TLR2 polypeptide, TLR3 polypeptide, TLR4 polypeptide, TLR5 polypeptide, TLR6 polypeptide, TLR7 polypeptide, TLR8 polypeptide, TLR9 polypeptide, TLR10 polypeptide, TIRAP polypeptide, TRAM polypeptide, MAL polypeptide, SARM polypeptide, IRAK1 polypeptide, IRAK4 polypeptide, TRAF6 polypeptide, TAK1 polypeptide, TAB1 polypeptide, TAB2 polypeptide, TAB3 polypeptide, IkBa polypeptide, RIP1 polypeptide, TRAF3 polypeptide, TBK1 polypeptide, IKKi polypeptide, IRF3 polypeptide, or combinations thereof have substantially no biological activity.

Donor cells can be mutated or otherwise genetically altered such that there is substantially no expression of p65, MYD88, TRIF, TP53, p50, IKK1, IKK2, NEMO, IL-1R1, TLR1, TLR2, TLR3, TLR4, TLR5, TLR6, TLR7, TLR8, TLR9, TLR10, TIRAP, TRAM, MAL, SARM, IRAK1, IRAK4, TRAF6, TAK1, TAB1, TAB2, TAB3, IkBa, RIP1, TRAF3, TBK1, IKKi, and/or IRF3 polypeptides in the cell. Donor cells can be mutated or otherwise genetically altered such that there is substantially no expression of p65 polypeptides, MYD88 polypeptides, TRIF polypeptides, TP53 polypeptides, p50 polypeptides, IKK1 polypeptides, IKK2 polypeptides, NEMO polypeptides, IL-1R1 polypeptides, TLR1 polypeptides, TLR2 polypeptides, TLR3 polypeptides, TLR4 polypeptides, TLR5 polypeptides, TLR6 polypeptides, TLR7 polypeptides, TLR8 polypeptides, TLR9 polypeptides, TLR10 polypeptides, TIRAP polypeptides, TRAM polypeptides, MAL polypeptides, SARM polypeptides, IRAK1 polypeptides, IRAK4 polypeptides, TRAF6 polypeptides, TAK1 polypeptides, TAB1 polypeptides, TAB2 polypeptides, TAB3 polypeptides, IkBa polypeptides, RIP1 polypeptides, TRAF3 polypeptides, TBK1 polypeptides, IKKi polypeptides, IRF3 polypeptides, or combinations thereof in the cells.

Expression and/or biological activity of any protein isoform or variant can be reduced. Exemplary human p65 protein sequences include, for example, GeneBank Accession numbers NP_068810, NP_001138610.1, NP_001230913.1, NP_001230914.1, XP_011543508.1, XP_011543509.1, and others. Exemplary human MYD88 protein sequences include, for example, GenBank Accession numbers NP_001166038.2, NP_002459.3, NP_001166039.2, NP_001166040.2, NP_001166037.2, NP_001352805.1, NP_001352806.1, NP_001361716.1, NP_001361717.1, and others. Exemplary human TRIF protein sequences include, for example, GenBank Accession number NP_891549.1, and others. Exemplary human TP53 protein sequences include, for example, GenBank Accession number BAC16799.1, and others. Exemplary human p105/p50 protein sequences include, for example, GenBank Accession numbers NP_003989.2, NP_001158884.1, NP_001306155.1, and others. Exemplary human IKK1 protein sequences include, for example, GenBank Accession number 015111.2, and others. Exemplary human IKK2 protein sequences include, for example, GenBank Accession number O14920.1, and others. Exemplary human NEMO protein sequences include, for example, GenBank Accession numbers Q9Y6K9.2, AAD38081.1, NP_001308326.1, NP_001308325.1, and others.

The polynucleotides encoding a p65 polypeptide, a MYD88 polypeptide, a TRIF polypeptide, a TP53 polypeptide, a p50 polypeptide, an IKK1 polypeptide, an IKK2 polypeptide, a NEMO polypeptide, an IL-1R1 polypeptide, a TLR1 polypeptide, a TLR2 polypeptide, a TLR3 polypeptide, a TLR4 polypeptide, a TLR5 polypeptide, a TLR6 polypeptide, a TLR7 polypeptide, a TLR8 polypeptide, a TLR9 polypeptide, a TLR10 polypeptide, a TIRAP polypeptide, a TRAM polypeptide, a MAL polypeptide, a SARM polypeptide, an IRAK1 polypeptide, an IRAK4 polypeptide, a TRAF6 polypeptide, a TAK1 polypeptide, a TAB1 polypeptide, a TAB2 polypeptide, a TAB3 polypeptide, an IkBa polypeptide, a RIP1 polypeptide, a TRAF3 polypeptide, a TBK1 polypeptide, an IKKi polypeptide, an IRF3 polypeptide can be deleted or mutated using a genetic manipulation technique selected from, for example, TALEN, Zinc Finger Nucleases, and CRISPR-Cas9.

One or more regulatory elements controlling expression of the polynucleotides encoding a p65 polypeptide, a MYD88 polypeptide, a TRIF polypeptide, a TP53 polypeptide, a p50 polypeptide, an IKK1 polypeptide, an IKK2 polypeptide, a NEMO polypeptide, an IL-1R1 polypeptide, a TLR1 polypeptide, a TLR2 polypeptide, a TLR3 polypeptide, a TLR4 polypeptide, a TLR5 polypeptide, a TLR6 polypeptide, a TLR7 polypeptide, a TLR8 polypeptide, a TLR9 polypeptide, a TLR10 polypeptide, a TIRAP polypeptide, a TRAM polypeptide, a MAL polypeptide, a SARM polypeptide, an IRAK1 polypeptide, an IRAK4 polypeptide, a TRAF6 polypeptide, a TAK1 polypeptide, a TAB1 polypeptide, a TAB2 polypeptide, a TAB3 polypeptide, an IkBa polypeptide, a RIP1 polypeptide, a TRAF3 polypeptide, a TBK1 polypeptide, an IKKi polypeptide, an IRF3 polypeptide, or combinations thereof can be mutated or replaced to prevent or attenuate expression of a p65 polypeptide, a MYD88 polypeptide, a TRIF polypeptide, a TP53 polypeptide, a p50 polypeptide, an IKK1 polypeptide, an IKK2 polypeptide, a NEMO polypeptide, an IL-1R1 polypeptide, a TLR1 polypeptide, a TLR2 polypeptide, a TLR3 polypeptide, a TLR4 polypeptide, a TLR5 polypeptide, a TLR6 polypeptide, a TLR7 polypeptide, a TLR8 polypeptide, a TLR9 polypeptide, a TLR10 polypeptide, a TIRAP polypeptide, a TRAM polypeptide, a MAL polypeptide, a SARM polypeptide, an IRAK1 polypeptide, an IRAK4 polypeptide, a TRAF6 polypeptide, a TAK1 polypeptide, a TAB1 polypeptide, a TAB2 polypeptide, a TAB3 polypeptide, an IkBa polypeptide, a RIP1 polypeptide, a TRAF3 polypeptide, a TBK1 polypeptide, an IKKi polypeptide, an IRF3 polypeptide, or combinations thereof as compared to a control or wild-type donor cells. For example, a promoter can be mutated or replaced such that the gene expression or polypeptide expression is attenuated or such that the polynucleotides are not transcribed. In one embodiment, one or more promoters for p65, MYD88, TRIF, TP53, p50, IKK1, IKK2, NEMO, IL-1R1, TLR1, TLR2, TLR3, TLR4, TLR5, TLR6, TLR7, TLR8, TLR9, TLR10, TIRAP, TRAM, MAL, SARM, IRAK1, IRAK4, TRAF6, TAK1, TAB1, TAB2, TAB3, IkBa, RIP1, TRAF3, TBK1, IKKi, IRF3 or combinations thereof are replaced with a promoter that has weaker activity than the wild-type promoter. A promoter with weaker activity transcribes the polynucleotide at a rate about 5, 10, 20, 30, 40, 50, 60, 70, 80, or 90% less than the wild-type promoter for that polynucleotide. In another embodiment, one or more promoters for p65, MYD88, TRIF, TP53, p50, IKK1, IKK2, NEMO, IL-1R1, TLR1, TLR2, TLR3, TLR4, TLR5, TLR6, TLR7, TLR8, TLR9, TLR10, TIRAP, TRAM, MAL, SARM, IRAK1, IRAK4, TRAF6, TAK1, TAB1, TAB2, TAB3, IkBa, RIP1, TRAF3, TBK1, IKKi, IRF3 or combinations thereof are replaced with a inducible promoter that can be controlled to attenuate expression of p65, MYD88, TRIF, TP53, p50, IKK1, IKK2, NEMO, IL-1R1, TLR1, TLR2, TLR3, TLR4, TLR5, TLR6, TLR7, TLR8, TLR9, TLR10, TIRAP, TRAM, MAL, SARM, IRAK1, IRAK4, TRAF6, TAK1, TAB1, TAB2, TAB3, IkBa, RIP1, TRAF3, TBK1, IKKi, IRF3 or combinations thereof.

The present disclosure provides donor cells lacking expression or having attenuated or reduced expression of p65, MYD88, TRIF, TP53, p50, IKK1, IKK2, NEMO, IL-1R1, TLR1, TLR2, TLR3, TLR4, TLR5, TLR6, TLR7, TLR8, TLR9, TLR10, TIRAP, TRAM, MAL, SARM, IRAK1, IRAK4, TRAF6, TAK1, TAB1, TAB2, TAB3, IkBa, RIP1, TRAF3, TBK1, IKKi, IRF3 polypeptides or combinations thereof, or expression of mutant p65, MYD88, TRIF, TP53, p50, IKK1, IKK2, NEMO, IL-1R1, TLR1, TLR2, TLR3, TLR4, TLR5, TLR6, TLR7, TLR8, TLR9, TLR10, TIRAP, TRAM, MAL, SARM, IRAK1, IRAK4, TRAF6, TAK1, TAB1, TAB2, TAB3, IkBa, RIP1, TRAF3, TBK1, IKKi, IRF3 polypeptides or combinations thereof that have reduced activity.

The reduced expression, non-expression, or expression of mutated, inactive, or reduced activity polypeptides can be affected by deletion of the polynucleotide or gene encoding p65, MYD88, TRIF, TP53, p50, IKK1, IKK2, NEMO, IL-1R1, TLR1, TLR2, TLR3, TLR4, TLR5, TLR6, TLR7, TLR8, TLR9, TLR10, TIRAP, TRAM, MAL, SARM, IRAK1, IRAK4, TRAF6, TAK1, TAB1, TAB2, TAB3, IkBa, RIP1, TRAF3, TBK1, IKKi, IRF3 replacement of the wild-type polynucleotide or gene with mutated forms, deletion of a portion of a p65, MYD88, TRIF, TP53, p50, IKK1, IKK2, NEMO, IL-1R1, TLR1, TLR2, TLR3, TLR4, TLR5, TLR6, TLR7, TLR8, TLR9, TLR10, TIRAP, TRAM, MAL, SARM, IRAK1, IRAK4, TRAF6, TAK1, TAB1, TAB2, TAB3, IkBa, RIP1, TRAF3, TBK1, IKKi, IRF3 polynucleotide or gene or combinations thereof to cause expression of an inactive form of the polypeptides, or manipulation of the regulatory elements (e.g. promoter) to prevent or reduce expression of wild-type p65, MYD88, TRIF, TP53, p50, IKK1, IKK2, NEMO, IL-1R1, TLR1, TLR2, TLR3, TLR4, TLR5, TLR6, TLR7, TLR8, TLR9, TLR10, TIRAP, TRAM, MAL, SARM, IRAK1, IRAK4, TRAF6, TAK1, TAB1, TAB2, TAB3, IkBa, RIP1, TRAF3, TBK1, IKKi, IRF3 polypeptides. The promoter could also be replaced with a weaker promoter or an inducible promoter that leads to reduced expression of the polypeptides. Any method of genetic manipulation that leads to a lack of, or reduced expression and/or activity of p65, MYD88, TRIF, TP53, p50, IKK1, IKK2, NEMO, IL-1R1, TLR1, TLR2, TLR3, TLR4, TLR5, TLR6, TLR7, TLR8, TLR9, TLR10, TIRAP, TRAM, MAL, SARM, IRAK1, IRAK4, TRAF6, TAK1, TAB1, TAB2, TAB3, IkBa, RIP1, TRAF3, TBK1, IKKi, IRF3 polypeptides and can be used in the present methods, including expression of inhibitor RNAs (e.g. shRNA, siRNA, and the like).

Wild-type refers to cells that are naturally occurring or that have not been recombinantly modified. Control donor cells can lack genetic modifications of test donor cells and can be used to test altered enzymatic or biological activity of genetically modified donor cells.

Gene Disruptions and Mutations

A genetic mutation comprises a change or changes in a polynucleotide sequence of a gene or related regulatory region or polynucleotide that alters the nucleotide sequence as compared to its native or wild-type sequence. Mutations include, for example, substitutions, additions, and deletions, in whole or in part, within the wild-type sequence. Such substitutions, additions, or deletions can be single nucleotide changes (e.g., one or more point mutations), or can be 2, 3, 4, 5, 6, 7, 8, 9, 10, or more nucleotide changes. Mutations can occur within the coding region of the gene or polynucleotide as well as within the non-coding and regulatory elements of a gene. A genetic mutation can also include silent and conservative mutations within a coding region as well as changes which alter the amino acid sequence of the polypeptide encoded by the gene or polynucleotide. A genetic mutation can, for example, increase, decrease, or otherwise alter the activity (e.g., biological activity) of the polypeptide product. A genetic mutation in a regulatory element can increase, decrease, or otherwise alter the expression of sequences operably linked to the altered regulatory element.

A gene disruption is a genetic alteration in a polynucleotide or gene that renders an encoded gene product (e.g., p65, MYD88, TRIF, TP53, p50, IKK1, IKK2, NEMO, IL-1R1, TLR1, TLR2, TLR3, TLR4, TLR5, TLR6, TLR7, TLR8, TLR9, TLR10, TIRAP, TRAM, MAL, SARM, IRAK1, IRAK4, TRAF6, TAK1, TAB1, TAB2, TAB3, IkBa, RIP1, TRAF3, TBK1, IKKi, IRF3) inactive or attenuated (e.g., produced at a lower amount or having lower enzymatic or biological activity). A gene disruption can include a disruption in a polynucleotide or gene that results in no expression of an encoded gene product, reduced expression of an encoded gene product, or expression of a gene product with reduced or attenuated enzymatic or biological activity. The genetic alteration can be, for example, deletion of the entire gene or polynucleotide, deletion of a regulatory element required for transcription or translation of the polynucleotide or gene, deletion of a regulatory element required for transcription or translation or the polynucleotide or gene, addition of a different regulatory element required for transcription or translation or the gene or polynucleotide, deletion of a portion (e.g. 1, 2, 3, 6, 9, 21, 30, 60, 90, 120 or more nucleic acids) of the gene or polynucleotide, which results in an inactive or partially active gene product, replacement of a gene's promoter with a weaker promoter, replacement or insertion of one or more amino acids of the encoded protein to reduce its activity, stability, or concentration, or inactivation of a gene's transactivating factor such as a regulatory protein. A gene disruption can include a null mutation, which is a mutation within a gene or a region containing a gene that results in the gene not being transcribed into RNA and/or translated into a functional gene product. An inactive gene product has no biological activity.

Zinc-finger nucleases (ZFNs), Talens, and CRISPR-Cas9 allow double strand DNA cleavage at specific sites in chromosomes such that targeted gene insertion or deletion can be performed. This approach can be used to modify the promoter of endogenous genes or the endogenous genes themselves to modify expression of p65, MYD88, TRIF, TP53, p50, IKK1, IKK2, NEMO, IL-1R1, TLR1, TLR2, TLR3, TLR4, TLR5, TLR6, TLR7, TLR8, TLR9, TLR10, TIRAP, TRAM, MAL, SARM, IRAK1, IRAK4, TRAF6, TAK1, TAB1, TAB2, TAB3, IkBa, RIP1, TRAF3, TBK1, IKKi, IRF3 which can be present in the genome of donor cells. ZFNs, Talens or CRISPR/Cas9 can be used to change the sequences regulating the expression of the polypeptides to increase or decrease the expression or alter the timing of expression beyond that found in a non-engineered or wild-type donor cells, or to delete the wild-type polynucleotide, or replace it with a deleted or mutated form to alter the expression and/or activity of p65, MYD88, TRIF, TP53, p50, IKK1, IKK2, NEMO, IL-1R1, TLR1, TLR2, TLR3, TLR4, TLR5, TLR6, TLR7, TLR8, TLR9, TLR10, TIRAP, TRAM, MAL, SARM, IRAK1, IRAK4, TRAF6, TAK1, TAB1, TAB2, TAB3, IkBa, RIP1, TRAF3, TBK1, IKKi, or IRF3.

Methods of Preparing Chimeric Blastocysts

Methods of preparing a chimeric blastocyst are provided herein. The methods can comprise injecting a host blastocyst from a first mammalian species with donor pluripotent stem cells from a second mammalian species, wherein the donor pluripotent stem cells have reduced expression or reduced biological activity of one or more proteins in the TLR/NF-kB signaling pathway or the p53 pathway.

Chimeric blastocysts can be prepared by injecting a host blastocyst from a first mammalian species with donor pluripotent stem cells (donor PSCs) from a second mammalian species using any suitable method, such as microinjection, for example. Host blastocysts can be injected at any stage after formation of the host blastocyst and before gastrulation. A person of skill in the art will appreciate that timing, such as days post-fertilization, for example, varies depending on host blastocyst species. Any number of donor PSCs can be injected into host blastocysts. About 1 donor PSCs, 5 donor PSCs, about 10 donor PSCs, about 20 donor PSCs, about 30 donor PSCs, about 40 donor PSCs, about 50 donor PSCs, and any number or range in between, can be injected into a host blastocyst. The host blastocyst can be an organogenesis disabled blastocyst or a wild-type blastocyst.

Methods of Making a Mammalian Organs and Tissues

Methods of obtaining a mammalian organ or tissue are provided herein. The methods can comprise: (i) injecting a host blastocyst, e.g., a organogenesis disabled blastocyst, from a first mammalian species with donor pluripotent stem cells from a second mammalian species to form a chimeric blastocyst, wherein the donor pluripotent stem cells have reduced expression or reduced biological activity of one or more proteins in the TLR/NF-kB signaling pathway or the p53 pathway; ii) implanting the chimeric blastocyst into a pseudo-pregnant mammal; and (iii) obtaining a chimeric embryo, fetus, or mammal comprising the mammalian organ or tissue.

The methods described herein can comprise, for example, implanting a chimeric blastocyst into a pseudo-pregnant mammal. A pseudo-pregnant mammal is primed so as to mirror the characteristics of a pregnant mammal. A host blastocyst will implant into the uterine wall of the pseudo-pregnant mammal and will continue to develop within the mammal. Methods of creating pseudo-pregnancy in animals and implanting blastocytes or embryos are well known in the art and are described, for example, in Hogan et al. (Manipulating the Mouse Embryo: A Laboratory Manual. 2.sup.nd ed. Cold Spring Harbor Laboratory Press, NY (1994)). The pseudo-pregnant mammal can be the same species as the first mammalian species from which the host blastocyst was derived. A pseudo-pregnant mammal can be any species selected from the order Artiodactyla (even-toed hoofed animals) of infra-order Ungulata, the order Carnivora (meat-eaters), the order Cetacea (whales and porpoises), the order Chiroptera (bats), the order Dermoptera (colugos or flying lemurs), the order Edentata (toothless mammals), the order Hyracoidae (hyraxes, dassies), the order Insectivora (insect-eaters), the order Lagomorpha (pikas, hares, and rabbits), the order Marsupialia (pouched animals), the order Mono-tremata (egg-laying mammals), the order Perissodactyla (odd-toed hoofed animals) of infra-order Ungulata, the order Pholidata, the order Pinnipedia (seals and walruses), the order Primates (primates), the order Proboscidea (el-ephants), the order Rodentia (gnawing mammals), the order Sirenia (dugongs and manatees), or the order Tubulidentata (aardvarks). In an embodiment, the pseudo-pregnant mam-mal is not a human.

The pseudo-pregnant mammal can be a non-primate species. For example, the pseudo-pregnant mammal can be a species of the order Artiodactyla, the order Carnivora, the order Lagomorpha, the order Perissodactyla, or the order Rodentia. The pseudo-pregnant mammal can be a rodent or an ungulate. The ungulate can be a species of the family Suidae. The pseudo-pregnant mammal can be a mouse, a rat, a pig, a cow, a sheep, a horse, a camel, a deer, a rhinoceros, an elephant, a giraffe, or a hippopotamus.

The methods can result in obtaining a chimeric embryo, fetus, or mammal. A chimeric embryo, fetus, or mammal can be obtained at any stage after implanting the chimeric blastocyst into a pseudo-pregnant mammal. A chimeric embryo, fetus, or mammal can comprise an organ or tissue derived in whole or in part from donor PSCs. About 1% of cells, 5% of cells, 10% of cells, 15% of cells, 20% of cells, 25% of cells, 30% of cells, 35% of cells, 45% of cells, 50% of cells, 55% of cells, 60% of cells, 65% of cells, 70% of cells, 75% of cells, 80% of cells, 85% of cells, 90% of cells, 95% of cells, 100% of cells, and any number or range in between, of the organ or tissue can be derived from donor PSCs. Any organ or tissue can be obtained including, for example, heart, kidney, liver, lung, pancreas, intestine, uterus, thymus, spleen, hematopoietic tissue, bone marrow, blood, musculoskeletal tissues, bone, tendons, ligaments, cornea, eye, skin, heart valves, nerves, neuronal tissue, spinal cord, blood vessels, veins, arteries, bladder, and lymphatic vessels, and/or any stem cells thereof.

Organs and tissues prepared by the methods provided herein can be used for the treatment of any disease by transplantation into a patient, for example. Organs and tissues prepared by the methods described herein can be derived from donor PSCs of the same patient or individual in need of treatment or transplantation. Donor PSCs can comprise iPSCs derived from the same patient in need of treatment or transplantation. In some embodiments, organs or tissues prepared by the methods described herein can be derived from an individual other than the patient in need of treatment or transplantation, for example, a relative of the patient or a non-relative of the patient. Organs or tissues prepared by the methods described herein can be derived from an HLA-matched or MHC-matched individual.

Any organ or tissue can be transplanted to treat a patient in need thereof, including, for example, heart, kidney, liver, lung, pancreas, intestine, uterus, thymus, spleen, hematopoietic tissue, bone marrow, blood, musculoskeletal tissues, bone, tendons, ligaments, cornea, eye, skin, heart valves, nerves, neuronal tissue, spinal cord, blood vessels, veins, arteries, bladder and lymphatic vessels, and/or any stem cells thereof. Exemplary diseases that can be treated by transplantation of an organ or tissue include cancer, heart failure, coronary artery disease, congenital heart disease, kidney failure, liver failure, cirrhosis of the liver, respiratory failure, lung disease, chronic obstructive pulmonary disease, emphysema, idiopathic pulmonary fibrosis, cystic fibrosis, idiopathic pulmonary hypertension, alpha 1-antitrypsin deficiency, bronchiectasis, sarcoidosis, keraconus, Fuchs' dystrophy, diabetes, severe combined immunodeficiency syndrome, aplastic anemia, congenital neutropenia, sickle cell anemia, thalassemia, intestine failure, ruptured spleen, burn, skin infection, skin cancer, venous ulcer, pressure ulcer, diabetic ulcer, wound, macular degeneration, glaucoma, retinoblastoma, complete paraplegia, complete tetraplegia, anterior cord syndrome, central cord syndrome, posterior cord syndrome, Brown-Sequard syndrome, Cauda *Equina* Lesion, congenital uterine disease, female infertility, intestinal failure, parenteral nutrition disorder, cornea thinning, cornea scarring, cornea clouding, cornea swelling, corneal ulcer, glaucoma, bone cancer, bone fracture, rheumatoid arthritis, osteoarthritis, ruptured tendon, amyotrophic lateral sclerosis, Parkinson's disease, Alzheimer's disease, Huntington's disease, aging, trauma, dementia, neurodegeneration, multiple sclerosis, congenital vascular disorder, and atherosclerosis.

The compositions and methods are more particularly described below and the Examples set forth herein are intended as illustrative only, as numerous modifications and variations therein will be apparent to those skilled in the art. As used in the description herein and throughout the claims that follow, the meaning of "a", "an", and "the" includes plural reference unless the context clearly dictates otherwise. The term "about" in association with a numerical value means that the value varies up or down by 5%. For example, for a value of about 100, means 95 to 105 (or any value between 95 and 105).

The terms used in the specification generally have their ordinary meanings in the art, within the context of the compositions and methods described herein, and in the specific context where each term is used. Some terms have been more specifically defined below to provide additional guidance to the practitioner regarding the description of the compositions and methods.

All patents, patent applications, and other scientific or technical writings referred to anywhere herein are incorporated by reference herein in their entirety. The embodiments illustratively described herein suitably can be practiced in the absence of any element or elements, limitation or limitations that are specifically or not specifically disclosed herein. Thus, for example, in each instance herein any of the terms "comprising", "consisting essentially of", and "consisting of" may be replaced with either of the other two terms, while retaining their ordinary meanings. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by embodiments, optional features, modification and variation of the concepts herein disclosed may be resorted to by those skilled in the art, and that such modifications and variations are considered to be within the scope of this invention as defined by the description and the appended claims.

Any single term, single element, single phrase, group of terms, group of phrases, or group of elements described herein can each be specifically excluded from the claims.

Whenever a range is given in the specification, for example, a temperature range, a time range, or a composition or concentration range, all intermediate ranges and subranges, as well as all individual values included in the ranges given are intended to be included in the disclosure. It will be understood that any subranges or individual values in a range or subrange that are included in the description herein can be excluded from the aspects herein. It will be understood that any elements or steps that are included in the description herein can be excluded from the claimed compositions or methods In addition, where features or aspects of the invention are described in terms of Markush groups or other grouping of alternatives, those skilled in the art will recognize that the invention is also thereby described in terms of any individual member or subgroup of members of the Markush group or other group.

The following are provided for exemplification purposes only and are not intended to limit the scope of the invention described in broad terms above.

EXAMPLES

Materials and Methods for Examples 1-8

Animals. CD-1 (ICR) mice were purchased from Charles River or Envigo (Harlen). Sprague Dawleuy (SD) rats were purchased from Envigo. Mice and rats were housed in 12-hr light/12-hr dark cycle. All procedures related to animals were performed in accordance with the ethical guidelines of the University of Texas Southwestern Medical Center. Animal protocols were reviewed and approved by the UT Southwestern Institutional Animal Care and Use Committee (IACUC) [Protocols #2018-102430 and #2018-102434].

Derivation of rat EpiSCs. Progression of estrous cycle and developmental stages of embryos were determined by performing vaginal cytological smears. Copulation time was determined by the presence of sperm in the vaginal smear under a microscope. If present, it is designated as E0.5. E7.5 stage embryos (corresponding to E5.75-6.0 in mouse) from Sprague Dawleuy rat were used for rat EpiSCs derivation. Briefly, surgically isolated epiblasts were placed on MEFs in chemically defined N2B27 medium supplemented with FGF2 (20 ng/ml, Peprotech) and IWR1 (2.5 μM, Sigma-Aldrich). After 4 days in culture, epiblast outgrowths were passaged as small clumps using Collegenase IV (Life Technologies) and replated onto newly prepared MEFs. Established rat EpiSCs were passaged every 3-4 days with TrypLE (Life Technologies) at a split ratio of 1:30.

Primed PSC culture. Primed human PSCs were either cultured on Matrigel (BD Biosciences) coated plates in mTeSR1 medium (StemCell Technologies) or on mitotically inactive mouse embryonic fibroblasts (MEFs) in NBFR medium, which contains DMEM/F12 (Invitrogen) and Neurobasal medium (Invitrogen) mixed at 1:1 ratio, 0.5×N2 supplement (Invitrogen), 0.5×B27 supplement (Invitrogen), 2 mM GlutaMax (Gibco); 1×NEAA (Gibco), 0.1 mM 2-Mercaptoethanol (Sigma-Aldrich), 20 ng/ml FGF2 (Peprotech), 2.5 UM IWR1 (Sigma-Aldrich), and 1 mg/ml BSA (Low fatty acid, MP Biomedicals New Zealand Ltd, Cat No #ABFF). Primed mouse, rat and rhesus PSCs were all cultured on MEFs in NBFR medium. Primed PSCs cultured in NBFR medium were passaged using TrypLE (Gibco) at 1:10 (human and rhesus) every 4-5 days, and at 1:30 (mouse and rat) every 3-4 days. Primed human PSCs cultured in mTeSR1 medium on Matrigel were passaged every five days by exposure to Versene (Gibco).

Naive PSC culture. For naive human PSCs, two different culture conditions were adopted: 1) NHSM medium, which contains KnockOut DMEM (Invitrogen), 1× Pen-strep (Gibco), 2 mM GlutaMax (Gibco); 1×NEAA (Gibco), 0.1 mM 2-Mercaptoethanol (Sigma-Aldrich), 10 mg/ml Albumax-I (Invitrogen), 1×N2 supplement (Invitrogen), L-ascorbic acid 2-phosphate (Sigma-Aldrich), 20 ng/ml human LIF (Peprotech), 20 ng/ml human LR3-IGF1 (Peprotech), 8 g/ml FGF2 (Peprotech), 2 ng/ml TGFb1 (Peprotech), 3 µM CHIR99021 (Selleckchem), 1 µM PD0325901 (Selleckchem), 5 µM SB203580 (Selleckchem), 5 UM SP600125 (Selleckchem), 5 µM Y27632 (Torcris) and 0.4 µM LDN193189 (Selleckchem). 2) NB-LCDM medium, which contains DMEM/F12 (Invitrogen) and Neurobasal medium (Invitrogen) mixed at 1:1 ratio, 0.5×N2 supplement (Invitrogen), 0.5×B27 supplement (Invitrogen), 2 mM GlutaMax (Gibco); 1×NEAA (Gibco), 0.1 mM 2-Mercaptoethanol (Sigma-Aldrich), 5 mg/ml BSA (Sigma-Aldrich, A1470, optional) or 5% knockout serum replacement (KSR, Thermo Fisher Scientific, optional), 10 ng/ml recombinant human LIF (Peprotech), 5 µM CHIR99021 (Selleckchem), 2 µM(S)-(+)-Dimethindene maleate (Tocris), 2 µM Minocycline hydrochloride (Santa Cruz Biotechnology). Naive mouse ESCs were cultured in NB-2iL medium on MEFs and adapted to NHSM or NB-LCDM media for more than 5 passages before co-culture with naive human PSCs. NB-2iL medium contains DMEM/F12 (Invitrogen) and Neurobasal medium (Invitrogen) mixed at 1:1 ratio, 0.5×N2 supplement (Invitrogen), 0.5×B27 supplement (Invitrogen), 2 mM GlutaMax (Gibco); 1×NEAA (Gibco), 0.1 mM 2-Mercaptoethanol (Sigma-Aldrich), 10 ng/ml recombinant human LIF (Peprotech), 3 µM CHIR 99021 (Selleckchem) and 1 µM PD0325901 (Selleckchem). Other culture conditions include 5iLAF medium and PXGL medium.

Generation of fluorescently labeled PSCs. pCAG-IP-humanized Kusabira Orange (hKO) and pCAG-IP-enhanced green fluorescent protein (EGFP) was used for labeling PSCs, Briefly, 1-2 µg of pCAG-IP-hKO were transfected into 1-2 million dissociated PSCs using an Amaxa 4D-nucleofector following the protocol recommended by the manufacturer. 0.5-1 µg/ml of puromycin (Invitrogen) was added to the culture 2-3 days post-transfection. Drug-resistant colonies were manually picked between 7-14 days and further expanded clonally.

Interspecies PSC co-culture. PSCs from different species were seeded onto MEF coated plates and either cultured separately or mixed at different ratios for co-cultures. For most cell competition assays between human-mouse, human-rat, rhesus-mouse and rhesus-rat, primate and rodent PSCs were seeded at a 4:1 ratio. For human-mouse co-culture experiments, ratios at 1:1 and 10:1 were also tested. For human-rhesus and mouse-rat PSC co-cultures, cells were seeded at 1:1 ratio. For primed co-culture experiments, all species' PSCs were cultured in N2B27-NBFR medium on MEF. For naive co-culture experiments, human and mouse PSCs were either cultured in NHSM or N2B27-LCDM media on MEFs. For differentiation co-culture, N2B27-NBFR cultured human and mouse PSCs were switched to differentiation medium containing DMEM/F12 supplemented 10% FBS. At each of the indicated time points, cell concentration (CC) was manually counted and calculated, and the percentages of each species's cells were determined using the LSR II Flow Cytometer (BD Bioscience). Total cell numbers (IN) for each species in co-cultures was determined by multiplying total cell volume (V) with CC and percentage (P). tN=N×CC×P. Scanning imaging was performed using Leica DMi8 microscopy. Live-cell imaging was performed Nikon A1R confocal microscope. Cells were imaged every 5 minutes with a 20× or 10× (0.4 NA) objective.

Transwell and conditioned medium assay. For transwell experiments, Millipore Transwell 0.4 µm PET hanging inserts (Millicell, #MCH12H48) were used by placing them into 12 well plates. Coverslips were placed into both the upper insert and the bottom well. For contactless co-culture experiments, mEpiSCs and hESCs were seeded on the top insert and bottom well, respectively. For normal contact co-culture experiments in transwell, both mEpiSCs and hESCs were seeded on the top insert without coverslips. Conditioned media was collected from day 1 to day 5 co-cultures and separate-cultures, filtered through a cell strainer (BD Falcon Cell Strainer, 40 µm, Franklin Lakes, NJ) and centrifuged at 200 g for 10 min at 4° C. to remove cell debris, then used to culture H9 hESCs. For the concentrated CM, a total of 100 mL conditioned medium were collected from day 1 to day 5 co-cultures or separate-cultures, and concentrated to a final volume of ~10 mL using Amicon ultra centrifugal filter with 3 kD molecular weight cutoff (Millipore, #UFC900308).

Time-lapse imaging and analysis. Time-lapse imaging was performed with a Nikon A1R confocal microscope at 37° C. and 5% $CO_2$ using a Nikon Biostation CT. Cells were imaged every 5 min for at least 12 h using a 10×, 20×, or 60× (0.4 NA) objective. For time-lapse imaging of contactless co-culture on chamber slides (µ-Slide 2 Well Co-Culture, ibidi), H9 hESCs were seeded in the inner well, and mEpiSCs in the outer wells. After cell attachment, unattached cells and medium were aspirated. Each major well was then overlayed with 600 µL cell free medium followed by time-lapse imaging. For time-lapse imaging of co-cultures using micropatterns, the photoresist template was fabricated by negative photolithography as described previously[45]. The chrome mask was manufactured by the University of Texas at Dallas, and the KMPR 1050 photoresist (Microchem, Westborough, MA) was used following the manufacturers' protocol. The silicon (PDMS) mold was fabricated from Sylgard 184 Silicon Elastomer (Dow Corning, Midland, MI). The layered agarose technique is a simple process for cell patterning on glass[46]. However, since the agarose layer quickly detaches from the coverslip in cell culture conditions (37° C., 5% (v/v) $CO_2$), we first coated the glass coverslip with an ultra-thin layer of polystyrene dissolved in chloroform (0.2 mg/mL), and then exposed the coverslips to UV light (tissue culture hood) for 1 hour to graft the polystyrene layer and sterilize the coverslips. Finally, the PDMS stamps were sealed to the treated coverslip with feature-side down. A solution of 1% agarose in distilled water (10 mg/mL) was heated to 100° C. until the solution was crystal clear. Subsequently, 600 µL of the 1% agarose solution was mixed with 400 µL of 100% ethanol, and a drop of the hot agarose/ethanol solution was perfused through the gaps formed between the stamp and the coverslip. After several hours, the PDMS mold was carefully removed from the coverslip with fine-tipped forceps. Before plating the cells in normal culture media, the agarose-coated coverslips were incubated with fibronectin in PBS (50 µg/mL) for 1 h at 37° C. and rinsed twice with PBS. After time-lapse imaging, ImageJ was used to project the z-stacks in 2D, using maximum intensity projection and the resulting 2D images were assembled into a time-lapse video.

CRISPR knockout. The online software (MIT CRISPR Design Tool: crispr.mit.edu) was used to design all sgRNAs used in this study. The sequences of sgRNAs were included in Table 1. sgRNAs were cloned into the pSpCas9 (BB)-2A-EGFP (Addgene, PX458) plasmid through ligating annealed oligos with BbsI digested vector. The plasmid carrying specific sgRNA was then transfected into HFF-iPSCs using electroporation (Nepa Gene Co., Ltd. NEPA21). EGFP+ cells were collected by flow cytometry at 48 h after transfection and plated. Single clones were picked and expanded. Homozygous knock-out clones were confirmed by Sanger sequencing and western blotting.

TABLE 1

| | | sqRNA Sequences and Primers | |
|---|---|---|---|
| | Name | SEQ ID NO | Sequence |
| gRNAs | hP65 | (SEQ ID NO: 1) | ATTGAGCAGCCCAAGCAGCGGGG |
| | hMYD88 | (SEQ ID NO: 2) | CTTGAACGTGCGGACACAGGTGG |
| | hTP53 | (SEQ ID NO: 3) | ACCAGCAGCTCCTACACCGGCGG |
| | hTSC1 | (SEQ ID NO: 4) | CGAGAGGATGGATAAACGAGTGG |
| | rP65 | (SEQ ID NO: 5) | ATTGAGCAGCCCAAGCAGCGGGG |
| | rMYD88 | (SEQ ID NO: 6) | GAGCAGTGTCCCACAGACAAAGG |
| | rTP53 | (SEQ ID NO: 7) | GACAGGGTCACCTAATTCCATGG |
| Sequencing Primers | hP65 | (SEQ ID NO: 8); | F: GTGTGCTGACCCTGATCTCC; |
| | | (SEQ ID NO: 9) | R: TACTTCATAGCCCGCCTCCT |
| | hMYD88 | (SEQ ID NO: 10); | F: GCTCCAGATTGTAGGGCAGG; |
| | | (SEQ ID NO: 11) | R: GAAAGTCAGCCTCCTCACCC |
| | hTP53 | (SEQ ID NO: 12); | F: GAGACCTGTGGGAAGCGAAA; |
| | | (SEQ ID NO: 13) | R: GCTGCCCTGGTAGGTTTTCT |
| | hTSC1 | (SEQ ID NO: 14); | F: CATGAGCTGCAAACTGGCTG; |
| | | (SEQ ID NO: 15) | R: TGAGGGAAGGCTAAACGATGAC |
| | rP65 | (SEQ ID NO: 16); | F: AGTAGGTAGGGGCTGTCCTG; |
| | | (SEQ ID NO: 17) | R: GGACAGAGCAAGGACTCTGG |
| | rMYD88 | (SEQ ID NO: 18); | F: AGGGAGAGGGTTAGTCCGTC; |
| | | (SEQ ID NO: 19) | R: CTTGCCCAAAGTCCCCAGAT |
| | rTP53 | (SEQ ID NO: 20); | F: GCTAGCCTGGGGTAAGTGAG; |
| | | (SEQ ID NO: 21) | R: AAAGCAACTCTTCAGGCCCA |
| qPCR Primers | hTp53 | (SEQ ID NO: 22); | F: GCGAGCACTGCCCAACAACA; |
| | | (SEQ ID NO: 23) | R: GGATCTGAAGGGTGAAATATTCT |
| | TFCP2L1 | (SEQ ID NO: 24); | F: GCTCTTCAACGCCATCAAA; |
| | | (SEQ ID NO: 25) | R: CAGGGGCACTCGATTCTG |
| | STELLA | (SEQ ID NO: 26); | F: GTTACTGGGCGGAGTTCGTA; |
| | | (SEQ ID NO: 27) | R: TGAAGTGGCTTGGTGTCTTG |
| | TBX3 | (SEQ ID NO: 28); | F: GCAGCTTTCAACTGCTTCG; |
| | | (SEQ ID NO: 29) | R: ACCCTCGCTGGGACATAAAT |
| | KLF4 | (SEQ ID NO: 30); | F: GGGAGAAGACACTGCGTCA; |
| | | (SEQ ID NO: 31) | R: GGAAGCACTGGGGGAAGT |
| | KLF17 | (SEQ ID NO: 32); | F: CTCCTGCTGCTGGTCCTTAG; |
| | | (SEQ ID NO: 33) | R: ACAGTTGCCACGTCCAGTG |
| | DPPA3 | (SEQ ID NO: 34); | F: AATGCTAGAATAGGGAATCAAGACA; |
| | | (SEQ ID NO: 35) | R: AGCATAGAGTAGCTTTCTCAACCTG |
| Genomic PCR | TPA-25 Alu | (SEQ ID NO: 36); | F: GTAAGAGTTCCGTAACAGGACAGCT; |
| | | (SEQ ID NO: 37) | R: CCCCACCCTAGGAGAACTTCTCTTT |
| | PTGER2 | (SEQ ID NO: 38); | F: TACCTGCAGCTGTACGCCAC; |
| | | (SEQ ID NO: 39) | R: GCCAGGAGAATGAGGTGGTC |
| | Rat specific mtDNA primer | (SEQ ID NO: 40); (SEQ ID NO: 41) | F: GACCTCCCCGCCCCATCTAACATCTCA TCATGATGAAA; R: GAATGGGATTTTGTCTGCGTCGGAGTT T |
| | Rat-mouse conserved mtDNA primer | (SEQ ID NO: 42); (SEQ ID NO: 43) | F: GCTAAGACCCAAACTGGGATT; R: GGTTTGCTGAAGATGGCGGTA |

*Underlined, PAM sequences; F: forward primer; R: reverse primer

Plasmids. The lentiviral construct for p53 short hairpin RNA (shp53 pLKO.1 puro) was obtained from Dr. Bob Weinberg (Addgene plasmid #19119). The plasmid carrying GFP-Bcl-2 (plasmid #17999) was purchased from Addgene. pGFP-Bcl2 vector was used as a template to generate pCAG-IP-Bcl2 with puromycin frame.

Mouse embryo collection. CD-1 female mice (8-10 weeks old) in natural estrous cycles were mated with CD-1 male mice. Blastocysts were harvested at E3.5 (the presence of a virginal plug was defined as E0.5) in KSOM-Hepes by flushing out the uterine horns. Blastocysts were cultured in the mKSOMaa in a humidified atmosphere containing 5% (v/v) CO2 and 20% (v/v) O2 at 37° C. until h-iPSC injections.

Human-mouse ex vivo chimera formation. Microinjection of human iPSCs into mouse blastocysts were performed as described previously with some modification. Briefly, cells pretreated with 10 UM Y-27632 were dissociated into single cells using Accutase and centrifuged at 200×g at room temperature for 3 min. After removal of the supernatant, cells were resuspended in culture medium containing 10 UM Y-27632 at a density of 2 to 6×10⁵ cells/mL and placed on ice for 20-30 min before injection. Single cell suspensions were added to a 40 µL droplet of KSOM-Hepes containing the blastocysts and placed on an inverted microscope (Leica) fitted with micromanipulators (Narishige). Individual cells were collected into a micropipette with 20 pm internal diameter and the Piezo Micro Manipulator (Prime Tech, Japan) was used to create a hole in the zona pellucida and trophectoderm layer of mouse blastocysts. 10-15 cells were introduced into the blastocoel. After microinjection, the blastocysts were cultured in vitro. To culture mouse blastocysts injected with human iPSCs beyond the implantation stages, a published protocol was followed. Briefly, injected mouse blastocysts were placed in ibiTreat µ-plate wells (eight-well Ibidi, cat. no. 80826) containing IVC1 medium. This is designated as day 0 of the in vitro culture. After all of the embryos were stably attached to the bottom of the well (between days 2 and 3), IVC1 medium was removed and replaced with equilibrated IVC2 medium. Approximately days 4 and 5 early egg cylinder emerged from the ICM clumps, and after further culture (~ day 6) the proamniotic cavity because visible.

Microinjection of Rat ESCs to Mouse Blastocysts. The embryos that have obvious blastocoel at E3.5 were defined as blastocysts. Single cell suspensions of rat ESCs were added to a 40 µL drop of KSOM-HEPES containing the blastocysts to be injected. Individual cells were collected into a 20 µm ID of micropipette. 10 cells were introduced into the blastocoel near the ICM. Groups of 10-12 blastocysts were manipulated simultaneously and each session was limited to 30 min. After microinjection, the blastocysts were cultured in mKSOMaa for at least 1 h until the embryo transfer.

Mouse Embryo Transfer. ICR female mice used as surrogates (~8 weeks old) were mated with vasectomized ICR male mice to induce pseudopregnancy. 10-15 injected blastocysts were transferred to each uterine horn of 2.5 days post coitum pseudo-pregnant females. Embryos were dissected at the indicated time points and used for downstream analysis. For testing chimera competency of J1 mESCs cultured in 5iLAF condition, C57BL/6J blastocysts were used for microinjection.

Genomic PCR. Genomic PCR was carried out for the detection of human-specific DNA in mouse embryo by DNA fingerprinting using primers for TPA-25 Alu. Genomic DNA of E8-9 or E10.5 mouse embryos and HFF-hiPSCs, Rat DAC8 (used as a positive control) were extracted using Wizard SV genomic DNA purification system (Promega), and diluted to 30 ng/uL as PCR templates. Genomic PCRs were performed using Hot Start Taq 2× Master Mix (NEB). The PCR products were examined by 2% agarose gel electrophoresis. Bands of expected size were cut and purified using Gel Extraction kit (Sigma-Aldrich) and then sent for Sanger sequencing. Primer sequences are provided in Table 1.

Quantitative Genomic PCR. Quantitative PCR (qPCR) for quantifying rat ESC contribution in rat-mouse chimeric embryos was performed using SYBR Green PCR Master Mix (Applied Biosystems) and total genomic DNAs isolated from E10.5 chimera, mouse ESCs and DAC8 rat ESCs. The data were analyzed using the $\Delta\Delta CT$ method, which were first normalized to the values of the mouse and rat common mitochondrial DNA (mtDNA) primers. A rat specific mtDNA primer was used for detecting rat cells. The levels of chimerism were determined based on the values of genomic DNA generated from serial dilutions of rat:mouse cells. The primers used for genomic qPCR are listed in Table 1.

Immunofluorescence. Cells were fixed in 4% Paraformaldehyde (PFA) for 10 min at room temperature, permeabilized with 0.4% Triton X-100 for 5 min and blocked with 10% BSA (Sigma-Aldrich), 0.1% Triton X-100 for 1 h. Staining with primary antibodies (Table 2) was performed overnight at 4° C. in 1% BSA, 0.1% Triton X-100. After three washes in PBS, secondary antibodies (Table 3) and DAPI were applied for 1 h. Coverslips were then mounted on glass slides using Vectashield (Vector Labs). The images of stained slides were taken by Revolve (ECHO) or Nikon A1R confocal microscope. All quantitative analysis of immunostained sections were carried out using Nikon NIS-Elements AR. To determine the percentage of cells that express AC3, we counted all AC3+ cells in two randomly selected fields (318.2 µm×318.2 µm each) in five immunostained slices per samples and calculated the percentage of marker-positive cells out of the total DAPI and GFP or mKO+ cells.

TABLE 2

| Antibodies for Immunostaining and Western Blot | | | | | |
|---|---|---|---|---|---|
| Antibody | Species | Manufacturer | Catalog Number | Application | Dilution |
| NF-κB p65 (D14E12) | Rabbit | Cell signaling | #8242 | Western Blot | 1:1000 |
| Bcl-2 Antibody | Mouse | Santa Cruz biotechnology | sc-7382 | Western Blot | 1:500 |
| Cleaved Caspase-3 | Rabbit | Cell signaling | 9661s | Immunostaining | 1:400 |
| GAPDH | Mouse | EMD Millipore | MAB374 | Western Blot | 1:20000 |
| OCT-3/4 | Mouse | Santa Cruz biotechnology | sc-5279 | Immunostaining | 1:500 |
| SOX2 | Goat | R&D Systems | AF2018 | Immunostaining | 1:500 |
| TRA-1-60-647 | Mouse | Santa Cruz biotechnology | sc-21705 | flow cytometry | 1 µg per 1 × 10⁶ cells |
| SSEA-1-488 | Mouse | Santa Cruz biotechnology | sc-21702 | flow cytometry | 1 µg per 1 × 10⁶ cells |
| phospho-S6K1 | Rabbit | Cell signaling | #9234 | Western Blot | 1:1000 |
| TSC1 | Rabbit | Cell signaling | #6935 | Western Blot | 1:1000 |
| PAX6 | Rabbit | Invitrogen | #42-6600 | Immunostaining | 1:150 |
| GFP | Chicken | AVES | GFP697986 | Immunostaining | 1:1000 |
| CD24-APC | Mouse | BioLegend | 311131 | flow cytometry | 1 µg per 1 × 10⁶ cells |

TABLE 2-continued

| Antibody | Species | Manufacturer | Catalog Number | Application | Dilution |
|---|---|---|---|---|---|
| | | Antibodies for Immunostaining and Western Blot | | | |
| SOX2 | Mouse | Santa Cruz biotechnology | Sc-365823 | Immunostaining | 1:500 |
| CD24-FITC | Mouse | BioLegend | 311104 | flow cytometry | 1 µg per $1 \times 10^6$ cells |
| SOX17 | Rabbit | R&D Systems | MAB1924 | Immunostaining | 1:500 |
| CALPONIN 1 | Rabbit | Abcam | ab46794 | Immunostaining | 1:500 |
| SUSD2-PE | Mouse | BioLegend | 327406 | Immunostaining | 1:400 |
| Vinculin | Rabbit | Cell signaling | #4650 | Western Blot | 1:1000 |
| p53 | Mouse | Cell signaling | #2524 | Western Blot | 1:1000 |
| IκBα | Mouse | Cell signaling | #4814 | Western Blot | 1:1000 |
| Myd88 | Rabbit | Cell signaling | #4283 | Western Blot | 1:1000 |
| Phospho-NF-κB p65 (Ser468) | Rabbit | Cell signaling | #3039 | Western Blot | 1:1000 |
| KLF17 | Rabbit | ATLAS | HPA024629 | Immunostaining | 1:500 |

TABLE 3

| Antibody | Species | Manufacturer | Catalog Number | Application | Dilution |
|---|---|---|---|---|---|
| | | Secondary Antibodies for Immunostaining and Western Blot | | | |
| Anti-Mouse FITC | Donkey | Jackson ImmunoResearch Laboratories, Inc | 715-095-151 | Immunostaining | 1:250 |
| Anti-Mouse Cy3 | Donkey | Jackson ImmunoResearch Laboratories, Inc | 715-165-151 | Immunostaining | 1:250 |
| Anti-Mouse Cy5 | Donkey | Jackson ImmunoResearch Laboratories, Inc | 715-175-151 | Immunostaining | 1:250 |
| Anti-Rabbit Cy3 | Donkey | Jackson ImmunoResearch Laboratories, Inc | 715-165-152 | Immunostaining | 1:250 |
| Anti-Rabbit Cy5 | Donkey | Jackson ImmunoResearch Laboratories, Inc | 715-175-152 | Immunostaining | 1:250 |
| Anti-Goat Cy3 | Donkey | Jackson ImmunoResearch Laboratories, Inc | 715-165-147 | Immunostaining | 1:250 |
| Anti-Goat FITC | Donkey | Jackson ImmunoResearch Laboratories, Inc | 715-095-147 | Immunostaining | 1:250 |
| Anti-Mouse | Sheep | GE Healthcare, Life Sciences | NA931V | Western blot | 1:2000 |
| Anti-Rabbit | Sheep | GE Healthcare, Life Sciences | NA934V | Western blot | 1:2000 |
| Anti-chicken FITC | Donkey | Jackson ImmunoResearch Laboratories, Inc | 703-095-155 | Immunostaining | 1:250 |
| Anti-Mouse IgG1, Alexa Fluor 647 | Goat | Invitrogen | A-21240 | Flow Cytometry | 1:300 |
| Anti-Mouse IgG2b, Alexa Fluor 594 | Goat | Invitrogen | A-21145 | Flow Cytometry | 1:300 |
| Anti-Mouse IgG1, Alexa Fluor 488 | Gaot | Invitrogen | A-21121 | Flow Cytometry | 1:300 |
| Anti-goat (H + L), Alexa Fluor 488 | Goat | Invitrogen | A-11005 | Flow Cytometry | 1:300 |
| Anti-goat (H + L), Alexa Fluor 594 | Goat | Invitrogen | A-11001 | Flow Cytometry | 1:300 |

Flow cytometry. Cells were dissociated using Accutase (Sigma-Aldrich) and fixed in 4% PFA in culture media for 10 min. Permeabilization was carried out using ice-cold methanol, and cells were blocked using 1% BSA. Cells were incubated with primary antibodies (Table 2) for 1 h at room temperature. After washing, secondary antibodies (Table 3) were applied. Cells were incubated with secondary antibodies for 45 min at 4° C. and washed in PBS prior to flow cytometry analysis. Flow cytometry was performed using a BD LSR II flow cytometer and analyzed using FlowJo software (BD Biosciences).

Immunohistochemistry analysis of mouse embryos. E8-9 embryos were dissected and fixed for 45 min in 4% PFA at 4° C., washed three times in PBS for 10 min each and submerged first in 30% Sucrose (Sigma-Aldrich) overnight at 4° C. until the embryos sank to the bottom of the tube. The day after, samples were subjected to increasing gradient of OCT concentration in Sucrose/PBS followed by embedding in OCT on liquid nitrogen and stored at −80° C. until further processing. Frozen embryo blocks were cut on a cryostat (LEICA CM1950) into 12-μm-thick sections, which were placed on superfrost plus microscope slides (Thermo Scientific) for immunostaining. The slides were washed once with PBS. After permeabilization with 0.1% Triton X-100 in PBS for 10 min, slides were again washed three times with PBS for 2 min each and blocked with 10% normal donkey/goat serum in PBS in humidified chamber for 1 h at RT. And then incubated with indicated primary antibodies (Table 2) overnight at 4° C., secondary antibodies (Table 3) for 2 h at 37° C., and finally DAPI. All images were captured on a Nikon NIS-Elements AR.

Western blotting. Cells were harvested by centrifugation and lysed in RIPA lysis buffer (150 mM NaCL, 1% Nonidet P-40, 0.5% Sodium deoxycholate (DOC), 0.1% SDS, 50 mM Tris-HCL) supplemented with 1 mM PMSF and 1× Halt complete protease inhibitor cocktail (Thermo Fisher Scientific). Cell lysates were sonicated for 5 min (Bioruptor UCD-200, Diagenode) and cleared by centrifugation at 14,000×g for 10 minutes at 4° C. (Hermle benchmark Z 216 MK). Cleared lysate was quantified using PIERCE BCA protein assay kit (Thermo Fisher Scientific) as per manufacturer instructions and absorbance was measured at 562 nm using a SpectraMax iD3 plate reader (Molecular Devices). Protein concentrations were normalized to the lowest sample. Samples were denatured with Laemmli buffer (0.05M Tris-HCl at pH 6.8, 1% SDS, 10% glycerol, 0.1% β-mercaptoethanol) by boiling for 10 minutes. 30 μg of total protein were resolved using Criterion TGX pre-cast gels (BioRad) followed by transfer to PVDF membranes. Transfer was visualized using Ponceau S staining solution (0.5% w/v Ponceau S, 1% acetic acid). Membrane was incubated with the corresponding primary antibodies (Table 2) after blocking for 1 h with 5% BSA/TBS Tween. Immunoreactive bands were visualized using HRP conjugated secondary antibodies (Table 3) incubated with chemiluminescence substrate (Pierce ECL western substrate, Thermo Fisher Scientific) and exposed to X-ray film.

RNA isolation and quantitative RT-PCR analysis. Total RNAs was extracted using RNeasy (Qiagen). cDNA was synthesized using Superscript III reverse transcriptase (Invitrogen), and SYBR Green Master Mix (Qiagen) was used for qPCR reaction. Quantitative real-time PCR (qRT-PCR) was carried out using CFX384 system (BIO-RAD). Reactions were run in triplicate and expression of each gene was normalized to the geometric mean of GAPDH as a housekeeping gene and analyzed by using the AACT method. The primer sequences of each gene are listed in Table 1.

RNA-sequencing. RNA extraction was performed using a RNeasy Mini Kit (QIAGEN) using DNase treatment (QIAGEN). RNA was analyzed using a 2100 Bioanalyzer (Aglient Technologies). (Transcripts per Kilobase Million). RNA-seq reads were mapped to the mouse genome and human genome using HISAT2 (version 2.1.0) with parameters "-k 1-p 4-q--no-unal--dta". The gene expression levels were then calculated using StringTie (v1.3.3b) with parameters "-t -e -B -A". A 2-fold variance in expression levels, a P value less than 0.05 and an adjusted P value less than 0.1 were used as cutoffs to define differentially expressed genes. The P value and adjusted P value were calculated using DESeq2. GO analysis preformed on DAVID (david-d.ncifcrf.gov/home.jsp).

Cell cycle analysis. For cell cycle analysis, cells were dissociated to single cells by treatment with Tryple for 10 min and separated by magnetic-activated cell sorting (MACS) following manufacturer's protocol. MEFs were removed first using feeder removal microbeads (Miltenyi Biotec, #130-095-531,). Anti-SSEA-1 (CD15) microbeads (Miltenyi Biotec, #130-094-530,) and Anti-TRA-1-60 MicroBeads (Miltenyi Biotec, #130-095-816) were used to enrich the rodent and primate PSCs respectively. Then cells were fixed in 70% ethanol overnight. After washing with PBS, the samples were incubated for 30 min with Tali™ cell cycle kit (Invitrogen, #A10798) in PBS and their DNA content was analyzed by flow cytometer (BD FACSAria) with 20,000 events per determination. Cell cycle profiles were generated using Flowjo software (Tree Star).

Teratoma formation. Cells were dissociated using Accuatse (Sigma-Aldrich) for 5 min at 37° C. and resuspended in 30% Matrigel (Corning) in DMEM/F12 (Hyclone), and then injected subcutaneously into NOD/SCID immunodeficient. Teratomas were detected after 8 weeks and fixed in 4% PFA. After paraffin embedding and sectioning, sections were stained with haematoxylin and eosin (H&E).

Teratoma formation. The teratoma formation experiments were approved by the Ethical Committee on Animal Experiments at Guangzhou Institutes of Biomedicine and Health, Chinese Academy of Sciences. Cells were digested by Accuatse (Sigma-Aldrich) for 5 min at 37° C. and resuspended in 30% Matrigel (Corning) in DMEM/F12 (Hyclone), and then injected subcutaneously into NOD/SCID immunodeficient mice, obtained from Beijing Vital River Laboratory Animal Technology Co., Ltd. Teratomas were detected after 8 weeks and fixed in 4% PFA. After paraffin embedding and sectioning, sections were stained with hematoxylin/eosin.

Statistics. Data were presented as mean±s.e.m. from at least three independent experiments. The Student's t-test (two-sided) was used to evaluate the significance of difference between two groups. Graphic analyses were done using GraphPad Prism version 8.0 (GraphPad Software, La Jolla, CA). Statistical analyses were done using the software SPSS 19.0 (SPSS, Chicago). p<0.05 was defined as statistically significant difference.

EXAMPLE 1. This example describes development of a co-culture system for pluripotent stem cells (PSCs) from different species.

PSCs can exhibit very limited efficiency in forming interspecies chimeras in an evolutionarily distant host. Uncovering the barriers and mechanisms underlying interspecies chimerism is of both conceptual and practical importance. Human PSCs (hPSCs) can undergo apoptosis, such that they disappear rapidly when injected into preimplantation embryos of multiple species including mouse, rabbit, pig, and sheep, which suggests that cell apoptosis is the first and general barrier in interspecies chimerism using human PSCs in these species.

Although molecular mechanisms underlying human cell apoptosis during interspecies chimera formation remain unknown, several studies tried to overcome cell apoptosis by directly blocking apoptosis, e.g., by overexpressing antiapoptotic genes such as BCL2 or BMI1 in human PSCs. However, no significant increase in human PSC interspecies chimerism levels in mice was achieved.

A co-culture system has been developed herein for PSCs from several different species, including mouse, rat, human, and monkey. By using this co-culture system, major cell competition was found between PSCs from evolutionary distant species, e.g., mouse/human, rat/human, mouse/monkey and rat/monkey. Mouse/rat PSCs are considered "winner," and human/monkey PSCs are "loser" with respect to the ability to survive and proliferate. Consequently, during co-culture, the numbers of human/monkey PSCs dramatically decreased, while mouse/rat PSCs proliferated at a comparable rate when compared with PSCs cultured separately. In contrast, only minor cell competition is observed between PSCs from evolutionary closer species, such as rat/mouse and human/monkey.

Through comparative RNA-seq analysis, TLR/NFkB signaling was found to be activated in both human and mouse PSCs upon co-culture. Human p65 (a key NFkB factor) relocated to the nucleus upon co-culture, confirming its activated status. Knocking out or knocking down p65 can overcome cell competition between, for example, mouse and human PSCs. Knock-out or knock-down of p65 also resulted in higher chimerism of human PSCs in mouse embryos. Knocking out or knocking down MYD88 can also overcome cell competition between, for example, mouse and human PSCs. Knock-out or knock-down of MYD88 also resulted in higher chimerism of human PSCs in mouse embryos. Furthermore, knocking out or knocking down TP53 can overcome cell competition between, for example, mouse and human PSCs. Knock-out or knock-down of TP53 also resulted in higher chimerism of human PSCs in mouse embryos.

During this co-culture process, the MYD88, TLR/NFkB, and P53 signaling pathways were involved in cell competition between cells from different species. Without being limited by theory, during interspecies chimera formation donor cells from a different species are likely out of sync with host embryonic cells, and thereby being treated as unfit cells targeted for elimination. Knock-out (KO) of, for example, p65, or MYD88, or TP53 in donor PSCs, such as hPSCs, can overcome the cell competition with host PSCs, such as mouse PSCs, and enable hPSCs to engraft both mouse pre-implantation and post-implantation embryos.

Together, these data demonstrate that donor PSCs with reduced expression or reduced biological activity of one or more proteins in the MYD88, NFkB, or P53 signaling pathways, such as p65 or MYD88, or TP53 KO or knock-down (KD) hPSCs, overcame cell competition and enabled the donor PSCs, (e.g., hPSCs) to integrate into pre and post-implantation embryos from evolutionarily distant species, such as mouse pre and post-implantation embryos.

EXAMPLE 2. This example describes modulation of the TLR/NF-kB signaling pathway and the p53 pathway.

After human PSCs were injected into a mouse blastocyst, after 3-5 days additional culture, most if not all human PSCs were eliminated from the mouse embryo, suggesting human cells have been competed out. To examine interspecies PSC competition in vitro, a culture condition was developed that supports the long-term maintenance of PSCs from human, monkey, mouse and rat. In this condition, when cultured separately, all PSCs proliferated well, maintained stable morphology, pluripotency marker expression and genome integrity over long term passages. When PSCs from evolutionary distant species were co-cultured together (mouse/rat co-cultured with human/monkey), cell competition occurred, while there was little to no cell competition between evolutionarily close species (mouse/rat, human/monkey). RNA-seq experiments were performed, comparing co-cultured human and mouse PSCs with separate culture controls. The TLR/NF-kB signaling pathway was activated in both co-cultured human and mouse PSCs. Knock-out or knock-down of p65 in human PSCs can overcome the cell competition with mouse PSCs and enabled more efficient and higher levels of human PSC chimerism in mouse embryos. Similar results were obtained with knock-out or knock-down of MYD88 and TP53. Partial rescue was obtained with knock-out or knock-down of TRIP. Without being limited by theory, donor PSCs with reduced expression or reduced biological activity of one or more proteins in the MYD88, NFkB, or P53 signaling pathways, such as p65, MYD88, TRIF, and TP53 knock-out or knock-down hPSCs, can increase the degree of interspecies chimerim in other animal hosts, e.g. pig, and thereby generate mammalian organs or tissues, such as human organs, in these species via interspecies chimeric complementation. Interspecies chimeras with mammalian or human PSC contributions could also serve as a novel platform for disease modeling and drug testing, providing in vivo readouts of disease onset and progression, drug efficacy and toxicity, with relevant clinical value.

EXAMPLE 3. This example describes establishment of in vitro systems based on the co-culture of naive and primed PSCs from different species.

Figure 1:
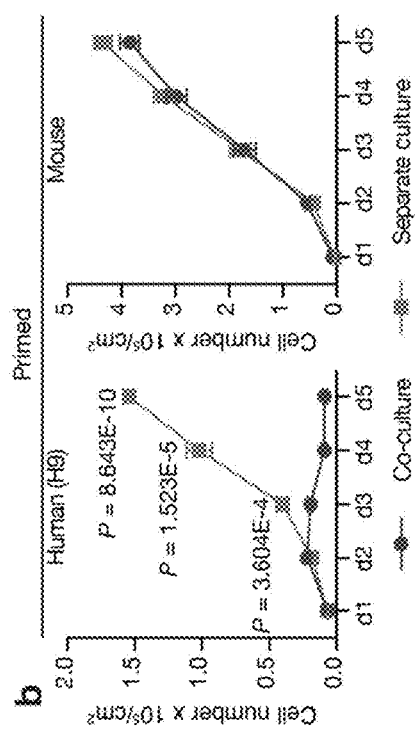
FIG. 1 panels a-h show interspecies cell competition between human and mouse primed PSCs. a, Schematic of experimental setup for interspecies PSC co-culture. b, Growth curves of H9 hES and mEpiSC under FR culture condition over 5 days in separate (squares) and co-culture (circles). Planting ratio=4:1 (human:mouse), n=8, biological replicates, mean±s.e.m. *P<0.001. c, Representative fluorescence images showing co-cultured and separately cultured H9 hESCs and mEpiSCs at day 5. Scale bar, 400 μm. d, Quantification of apoptotic cells by counting AC3+ cells of day 3 co-cultured and separately cultured H9 hESCs (first and third bar) and mEpiSCs (second and fourth bar), n=10, randomly selected fields (318.2×318.2 μm² each) from three independent immunostaining experiments per sample, mean±s.e.m. *P<0.001. e, Growth curves of human and mouse naïve PSC under 5iLAF condition over 5 days in separate (squares) and co-cultured (circles). Planting ratio=4:1 (human:mouse), n=3, biological replicates, mean±s.e.m. f, Growth curves of H9 hESCs and mEpiSCs under a differentiation condition over 5 days in separate (squares) and co-cultured (circles). Planting raio=4:1 (human:mouse), n=3 biological replicates, mean±s.e.m. g, Ratios (co-culture versus separate-culture) of day 5 live human cell numbers in naïve, primed and differentiation conditions. n=3, naïve and differentiation; n=8, primed, biological replicates, mean±s.e.m. h, Schematic summary of human-mouse primed PSC competition.
Figure 1:
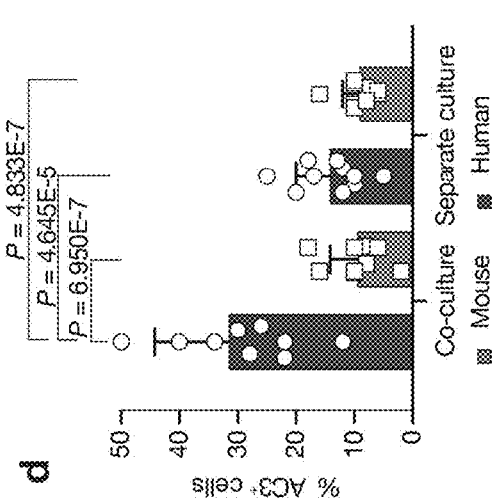
Figure 1:
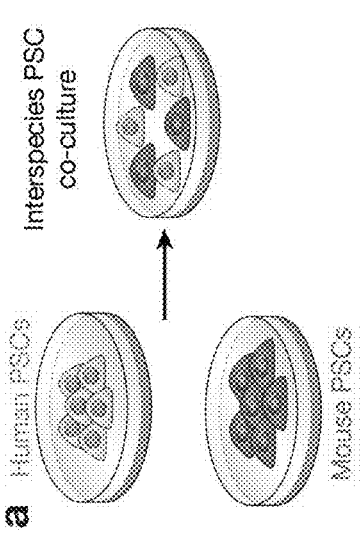
Figure 1:
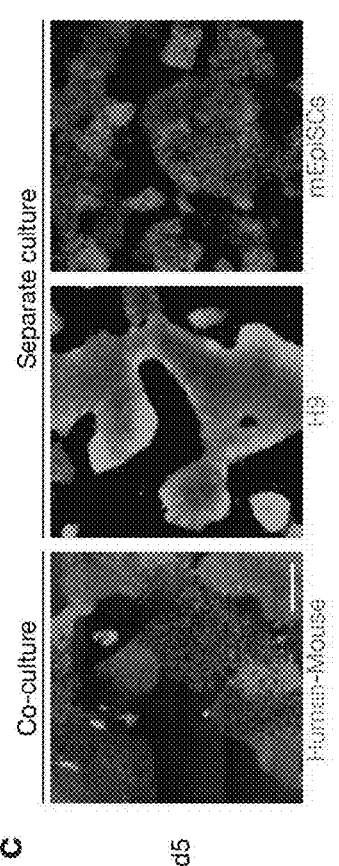
Figure 1:
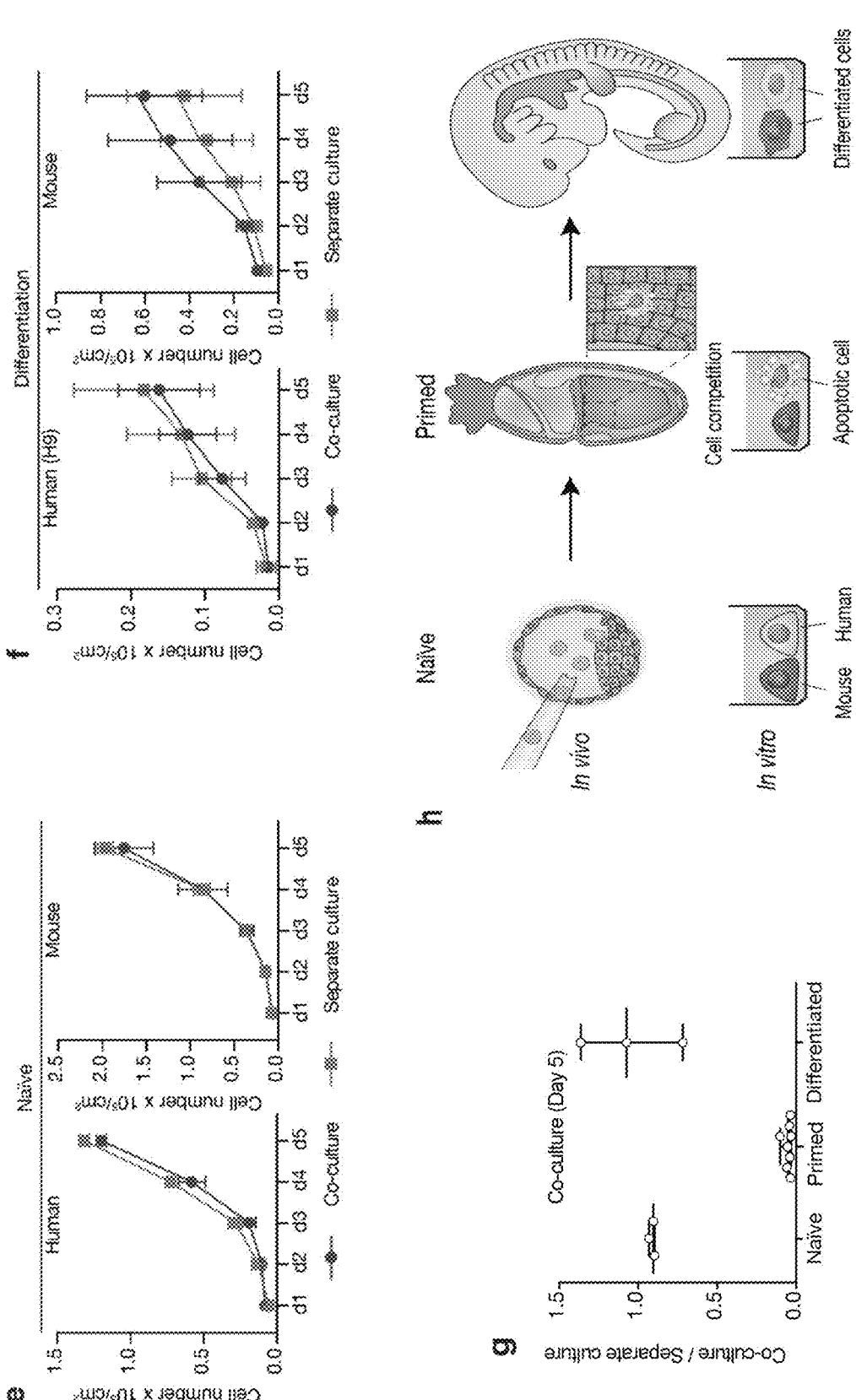
Figure 5:
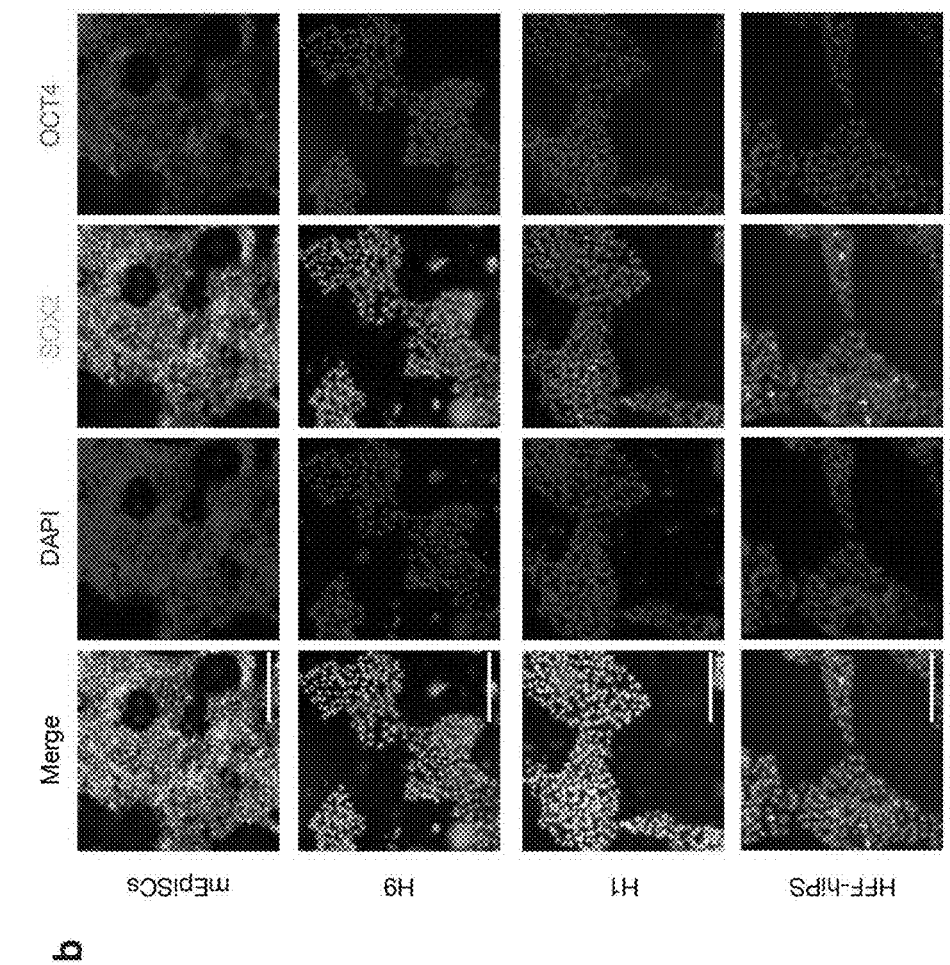
FIG. 5 panels a-f show an interspecies PSC co-culture. a, Representative brightfield images showing H9 hESCs (Passage #51) and mEpiSCs (Passage #30) cultured in primed FR condition. Scale bars, 200 μm. b, Representative immunofluorescence images showing mEpiSCs (Passage #32), H1
Figure 5:
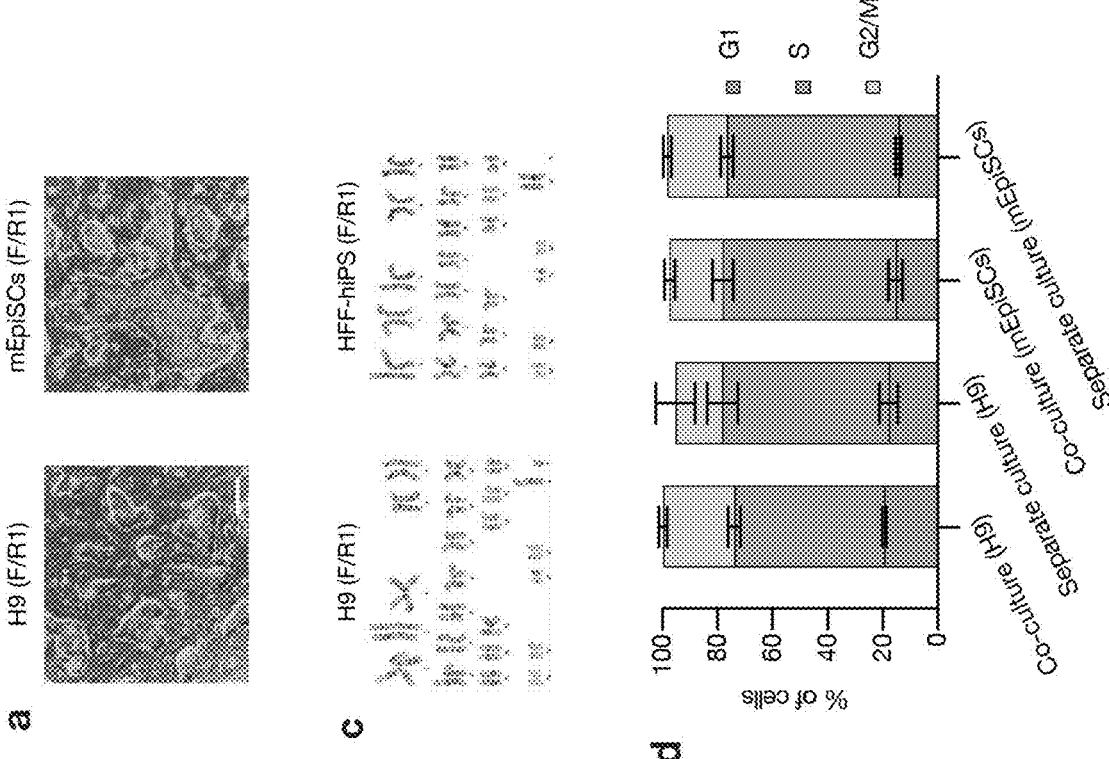
Figure 5:
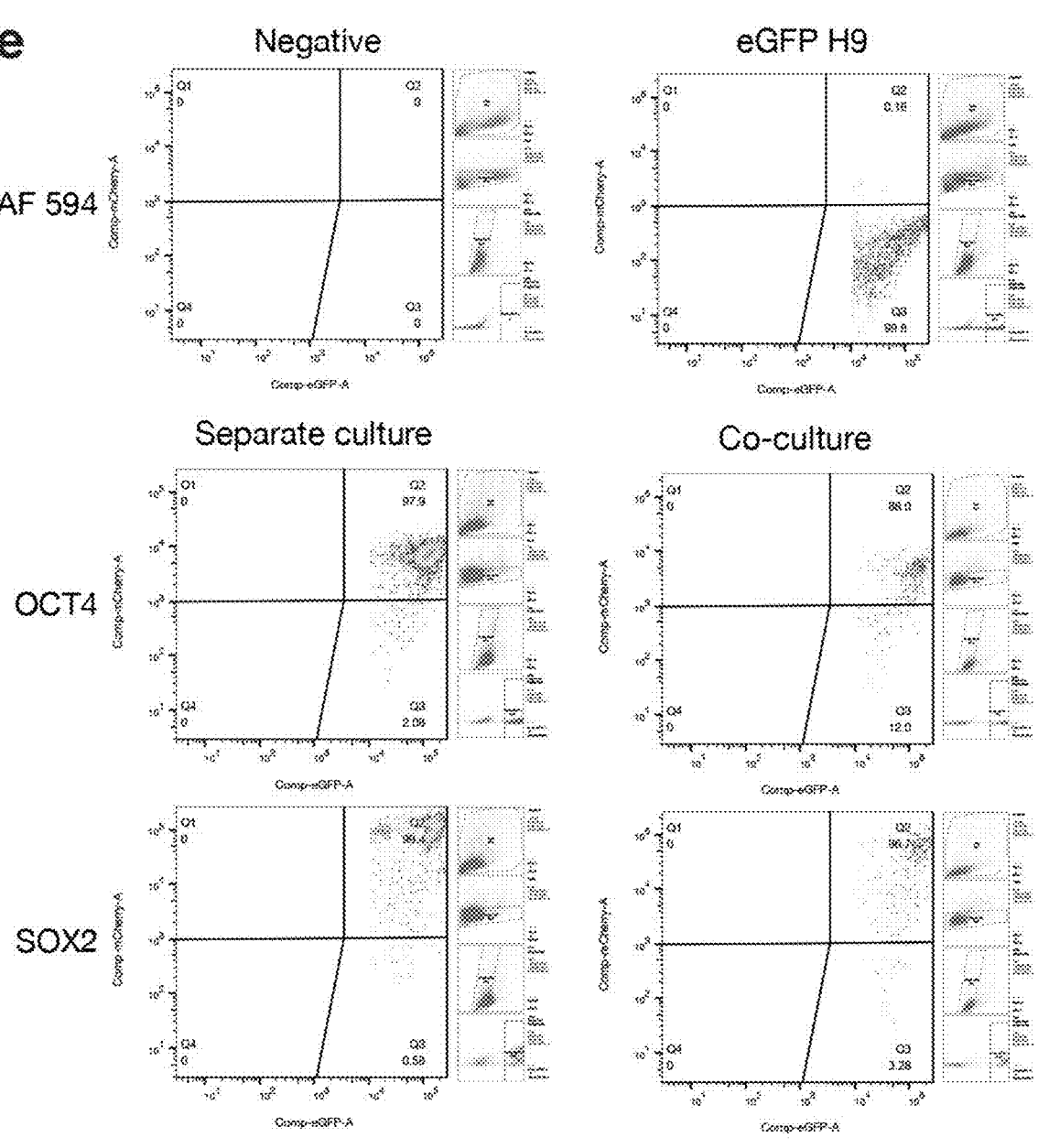
Figure 5:
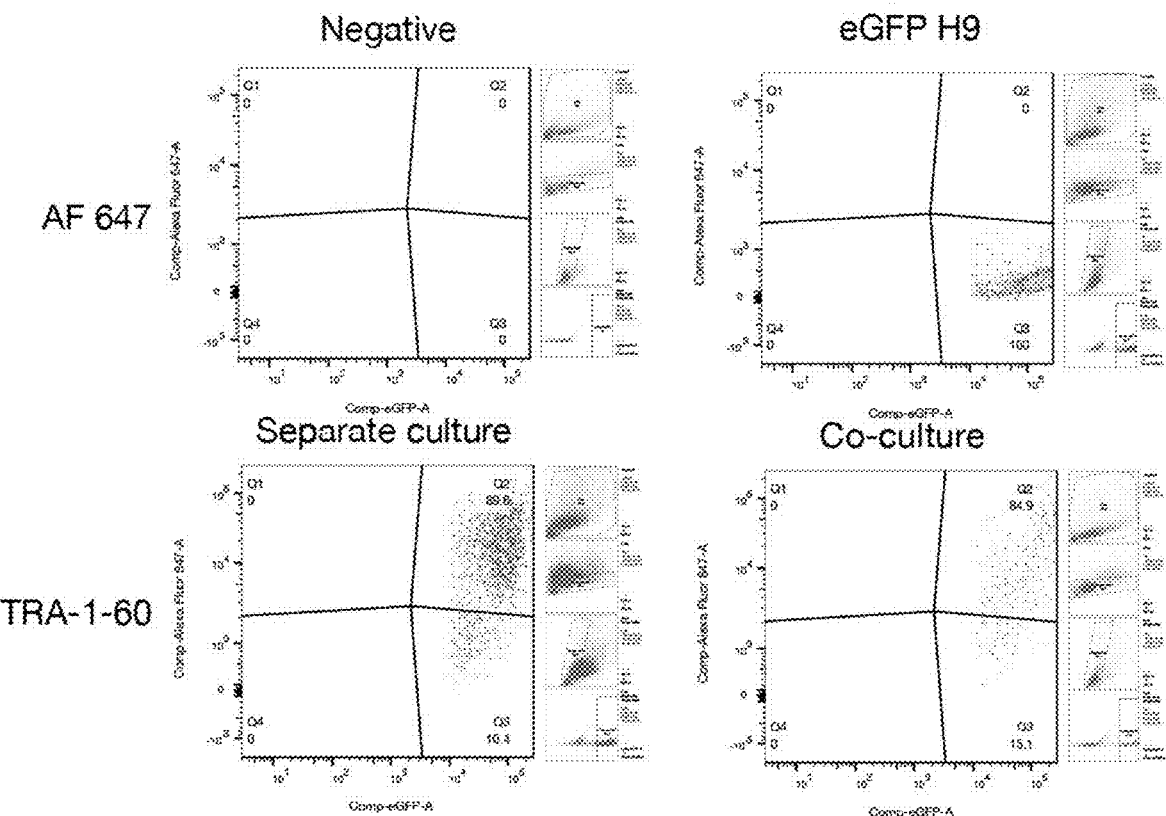
Figure 5:
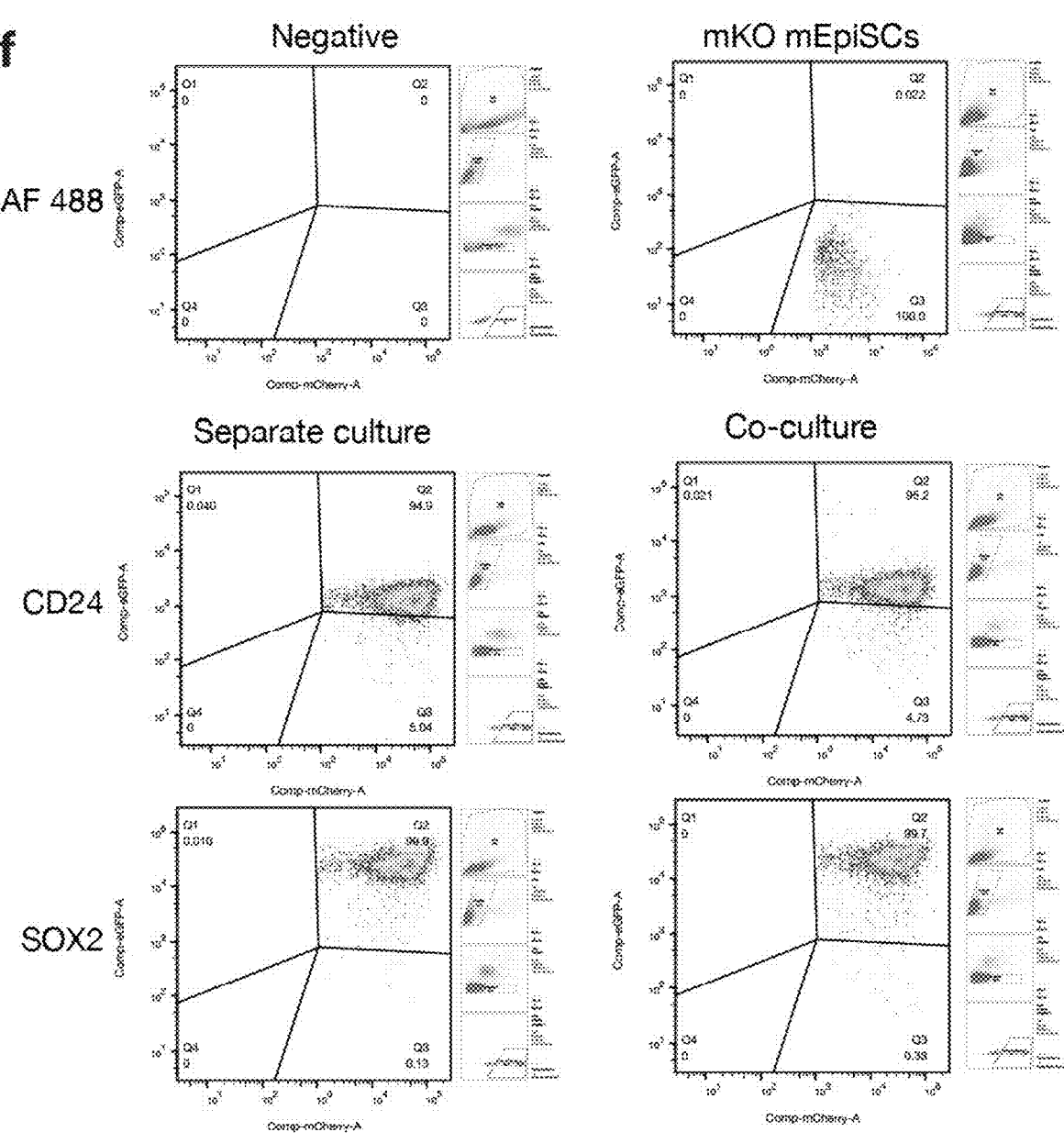
Figure 5:
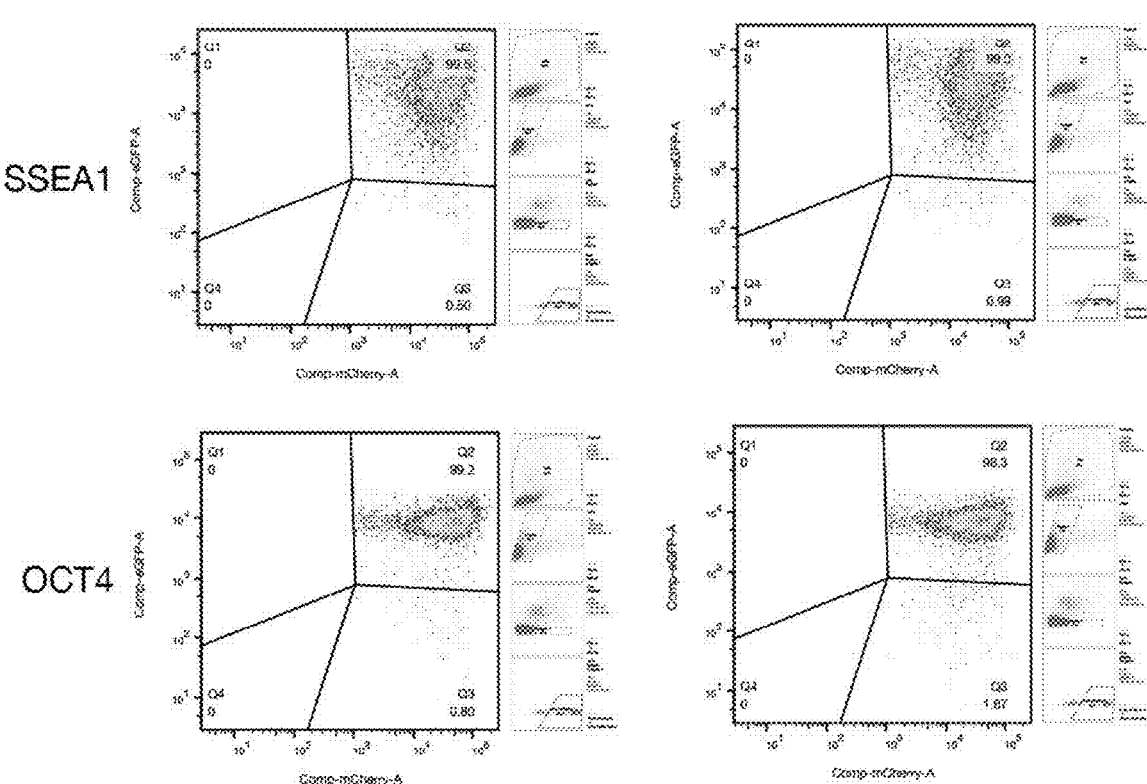

For primed PSCs, we used a culture condition containing bFGF and a canonical WNT inhibitor, IWR1 (FR condition), which supported long term culturing of both human and mouse PSCs. When cultured separately in FR condition, both H9 human embryonic stem cells (hESCs) and mouse epiblast stem cells (mEpiSCs) proliferated well and maintained stable colony morphology, pluripotency marker gene expression, and genome stability over long term passaging (FIG. 5a-c). We labeled H9 hESCs and mEpiSCs with Enhanced Green Fluorescent Protein (EGFP) and monomeric Kusabira Orange (mKO), respectively. Time-lapse confocal microscopy was performed on co-cultured H9 hESCs and mEpiSCs. Interestingly, we observed that, after coming into contact with mEpiSCs, many H9 hESCs underwent apoptotic cell death. Next, we calculated the cell number per $cm^2$ (total cell number divided by surface area) of live H9 hESCs and mEpiSCs in co-culture and separate-culture daily until they grew to confluency. Starting from day 3, significantly lower numbers of H9 hESCs were found in co-cultures than separate-cultures, while the numbers of mEpiSC remained comparable (FIG. 1b). Strikingly, on day 5, few H9 hESCs were present in co-culture (FIG. 1c). Co-cultured H9 hESCs and mEpiSCs maintained pluripotency marker expression profiles similar to separate cultures (FIG. 5e, f). As changes in cell cycle can have dramatic effect on cell growth dynamics, we compared cell cycle profiles of co-cultured with separately cultured H9 hESCs and mEpiSCs, and found no noticeable differences (FIG. 5d). Next, we examined cell apoptosis by active caspase-3 (AC3) and Annexin-V staining and found, when compared to separate-cultures, there was a significant increase in the percentage of $AC3^+$ and Annexin-$V^+$ cells in co-cultured H9 hESCs but not mEpiSCs (FIG. 1d and FIG. 6a,b). Besides H9 hESCs, similar results were obtained when using two other human PSC lines: H1 hESCs and HFF-iPSCs (FIG. 6c-f). Collectively, these results demonstrate competitive interaction between co-cultured human and mouse primed PSCs, and "winner" mouse cells induced the apoptosis of "loser" or less-fit human cells.

Next, the apoptosis status of H9 ESCs and mEpiSCs during separate- and co-culture was examined by active caspase-3 (AC3) staining. While the percentages of AC3+ cells were similar between separate- and co-cultured mEpiSCs, there was a significant increase in the percentage of AC3+ cells in co-cultured versus separate-cultured H9 ESCs (FIG. 1d). In agreement, flow cytometry analysis using another apoptosis marker, Annexin V, revealed significantly more H9 ESCs stained positive for Annexin V in co-culture versus separate-culture (FIG. 6b). In addition to a 4:1 ratio, other plating ratios of human and mouse PSCs (e.g. 1:1) were also tested. H9 ESCs were eliminated in all co-culture conditions tested. Besides H9 ESCs, similar results were obtained when using two other human PSC lines: H1 ESCs and HFF-iPSCs. Collectively, these results demonstrate competitive behavior between co-cultured human and mouse primed PSCs, and "winner" mEpiSCs induced the elimination of "loser" human PSCs.

To evaluate whether human-mouse PSC competition also occurs in naïve pluripotency, we tested several reported human naïve/naïve-like conditions (5iLAF, PXGL, NHSM and LCDM), which could also support long-term culture of mouse ESCs (mESCs) (FIG. 7a-e). In contrast to primed PSC co-culture, we did not observe overt cell competition between human and mouse PSCs in all naïve/naïve-like conditions tested (FIG. 1e, FIG. 7f-i). In addition, we found no apparent cell competition during early co-differentiation of human and mouse primed PSCs (FIG. 1f, FIG. 7j-l). Together, these results indicate that, at whole population level, human-mouse PSC competition is confined within primed pluripotency, which is consistent with the observation that elimination of less-fit pluripotent cells occurs in post-implantation mouse epiblasts in vivo, or following the exit of naïve pluripotency in vitro (FIG. 1g,h).

EXAMPLE 4. This example describes a link between evolutionary distance and primed PSC competition.

Without being limited by theory, genetic diversification has been proposed to be at least partly responsible for the xenogeneic barrier. To examine the link between evolutionary distance and primed PSC competition, a rhesus macaque ESC line (ORMES23) was culture adapted and a rat EpiSC line from E7.5 epiblast in FR condition was derived de novo. Similar to human and mouse, FR-cultured ORMES23 ESCs and rat EpiSCs stably maintained the expression of pluripotency markers SOX2 and OCT4 in long term cultures PSCs from species with different evolutionary distances (timetree-.org) from mouse, rat, human, and rhesus macaque for co-culture experiments were then mixed and matched. Similar to human-mouse (90 MYA), pronounced cell competition was observed during human-rat (90 MYA), rhesus-mouse (90 MYA), rhesus-rat (90 MYA) primed PSC co-cultures. "Loser" human or rhesus cells were eliminated by "winner" mouse or rat cells mostly after 5 days co-culture. In sharp contrast, little to no cell competition was observed in rat-mouse (~21 MYA) and human-rhesus (~29 MYA) PSC co-cultures.

Figure 4:
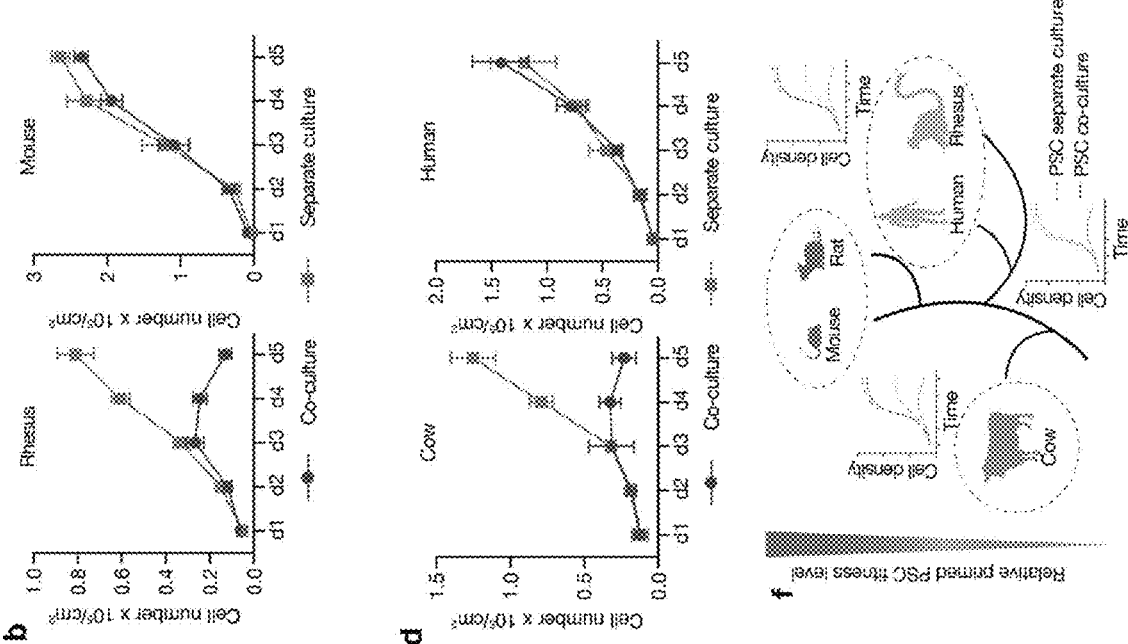
FIG. 4 panels a-f show primed PSC competition among evolutionarily distant species. a, Growth curves of H9 hESCs and rEpiSCs over 5 days in separate (squares) and co-culture (circles). Plating ratio=4:1 (human:rat). n=3, biological replicates, mean±s.e.m. *P<0.05, P<0.01. b, Growth curves of rhESCs (ORMES23) and mEpiSCs over 5 days in separate (squares) and co-culture (circles). Plating ratio=4:1 (rhesus:mouse). n=3, biological replicates, mean±s.e.m. *P<0.001. c, Growth curves of H9 hESCs and ORMES23 rhESCs over 5 days in separate (squares) and co-culture (circles). Plating ratio=1:1 (human:rhesus). n=3, biological replicates, mean±s.e.m. d, Growth curves of H9 hESCs and bESCs over 5 days in separate (squares) and co-culture (circles). Plating ratio=1:1 (cow:human). n=3, biological replicates, mean±s.e.m. *P<0.05, **P<0.01. e, Growth curves of bESCs and mEpiSCs over 5 days in separate (squares) and co-culture (circles). Plating ratio=4:1 (cow:mouse). n=3, biological replicates, mean±s.e.m, *P<0.05. f, A schematic summary showing the hierarchy of "winner" and "loser" species during interspecies primed PSC competition.
Figure 4:
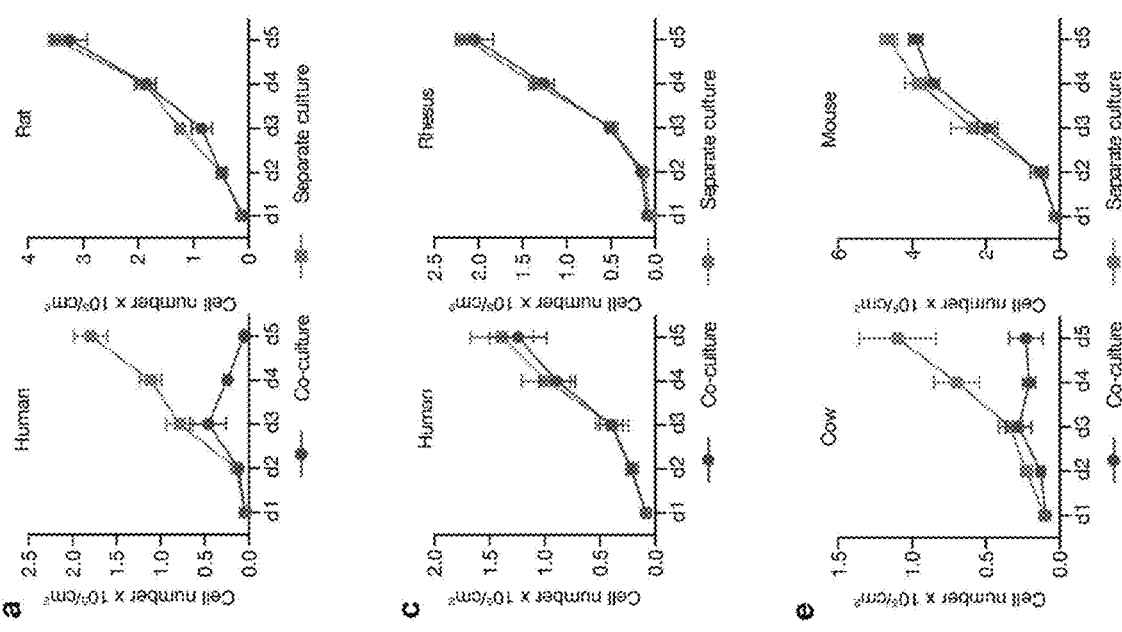

Collectively, these results suggest that cell competition occurs between primed PSCs from evolutionarily distant while not closely related species (FIG. 4f).

EXAMPLE 5. This example describes mechanisms underlying human-mouse primed PSC competition.

Whether cell competition was contact dependent was examined first to determine the mechanisms underlying human-mouse primed PSC competition. H9 ESCs and mEpiSCs were co-cultured using transwells to prevent direct cell-cell contact. Unlike "contact" co-culture, no evidence of cell competition between transwell co-cultured H9 ESCs and mEpiSCs was found (FIG. 2a; FIG. 8d). Therefore, direct cell contact is important for triggering cell competition between human and mouse primed PSCs.

Without being limited by theory, activation of apoptosis in less-fit cells represents the most widespread mechanism for eliminating loser cells in most cell competition models. Downregulation of the anti-apoptotic gene Bcl-2 has been linked to death of loser cells in mice. To test whether blocking loser cell apoptosis can overcome cell competition, human HFF-iPSCs that stably express the anti-apoptotic gene BCL-2 (BCL-2$^{OE}$-hiPSCs) were generated (FIG. 9a,b). BCL-2 overexpression was mostly effective in preventing the elimination of human PSCs during co-culture with mEpiSCs (FIG. 2c; FIG. 9c).

The pro-apoptotic protein P53 encoded by the TP53 gene in humans is emerging as an important player in cell competition in different mammalian systems. To test if P53 is involved in human cell death during interspecies primed PSC competition, shRNA was used to reduce P53 levels in HFF-iPSCs (TP53$^{KD}$-hiPSCs) (FIG. 9d,e). When TP53$^{KD}$-hiPSCs were co-cultured with mEpiSCs, a complete rescue of human cell death was observed (FIG. 9f,g). TP53 knock-out HFF-iPSCs (TP53$^{KO}$-hiPSCs) using CRISPR were also generated (FIG. 9h,i). Similar to TP53$^{KD}$-hiPSCs, abrogation of P53 could also overcome human-mouse primed PSC competition (FIG. 2d; FIG. 9j). mTOR signaling was shown to act downstream of p53 in cell competition in early mouse embryos and upon exit from naive plurpotency. To assess whether activation of mTOR signaling in human PSCs could overcome cell competition, TSC1, an inhibitor of the mTOR pathway, was targeted with CRISPR/Cas9 and a homozygous TSC1 knockout HFF-iPSCs (TSC1$^{KO}$-hiPSCs) was generated (FIG. 9k). The increase in mTOR activity induced by TSC1 deficiency did not rescue human PSC elimination by mEpiSCs (FIG. 9k-m). In sum, we demonstrate either overexpression of anti-apoptotic BCL2 or abrogation of pro-apoptotic TP53 can promote survival of human primed PSCs when co-cultured with mEpiSCs.

Figure 2:
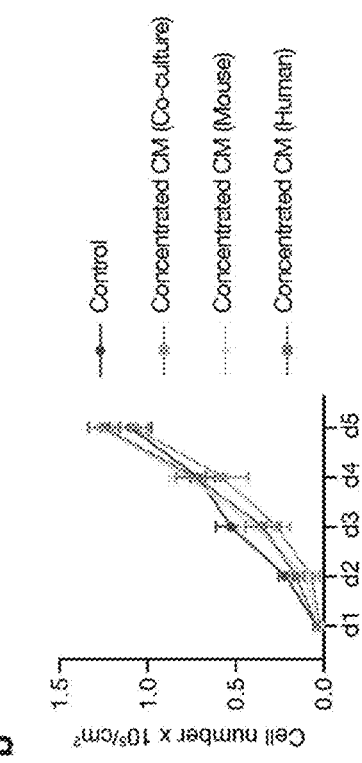
FIG. 2 panels a-h show mechanisms underlying human-mouse primed PSC competition. a, Growth curves of H9 hESCs and mEpiSCs over 5 days in separate (squares) and co-culture (circles) under transwell co-culture condition. n=3, biological replicates, mean±s.e.m. b, Growth curves of H9 hESCs treated with different types of concentrated conditioned medium. c, Growth curves of BCL-2$^{OE}$-hiPSCs (BCL-2$^{OE}$) and mEpiSCs over 5 days in separate (squares) and co-culture (circles). n=5, biological replicates, mean±s.e.m. d, Growth curves of TP53$^{KO}$-hiPSCs and mEpiSCs over 5 days in separate (squares) and co-culture (circles). n=3, biological replicates, mean±s.e.m. e, Schematic of the RNA-seq experimental setup. f, Left, Venn diagram showing the numbers of co-culture up-regulated genes (Co-URGs) in H9 hESCs during the first three days. Only genes with P<0.01, fold change >2 and FPKM>1 were included. Right, top 5 KEGG pathways enriched in day 1 only Co-URGs in H9 hESCs. g, Growth curves of P65$^{KO}$-hiPSCs (Clone #1A3) and mEpiSCs over 5 days in separate (squares) and co-culture (circles). n=3, biological replicates, mean±s.e.m. h, Growth curves of MYD88$^{KO}$-hiPSCs and mEpiSCs over 5 days in separate (squares) and co-culture (circles). n=3, biological replicates, mean±s.e.m.
Figure 2:
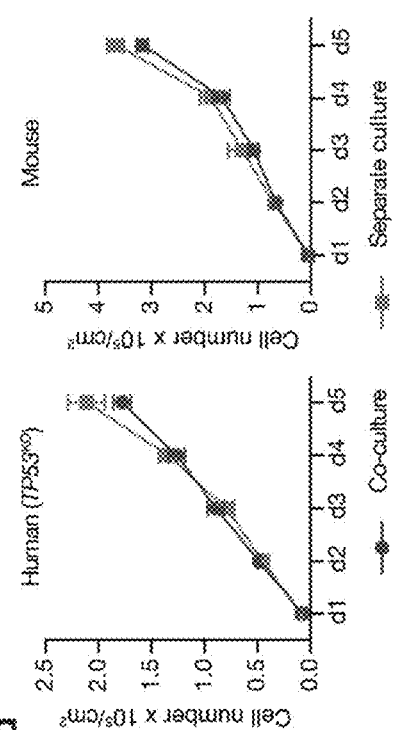
Figure 2:
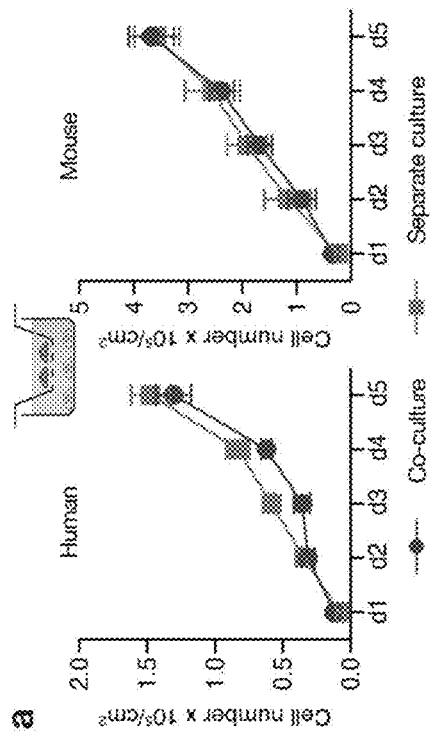
Figure 2:
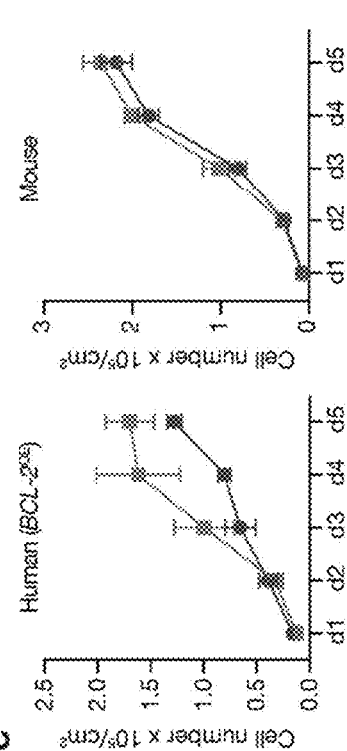
Figure 2:
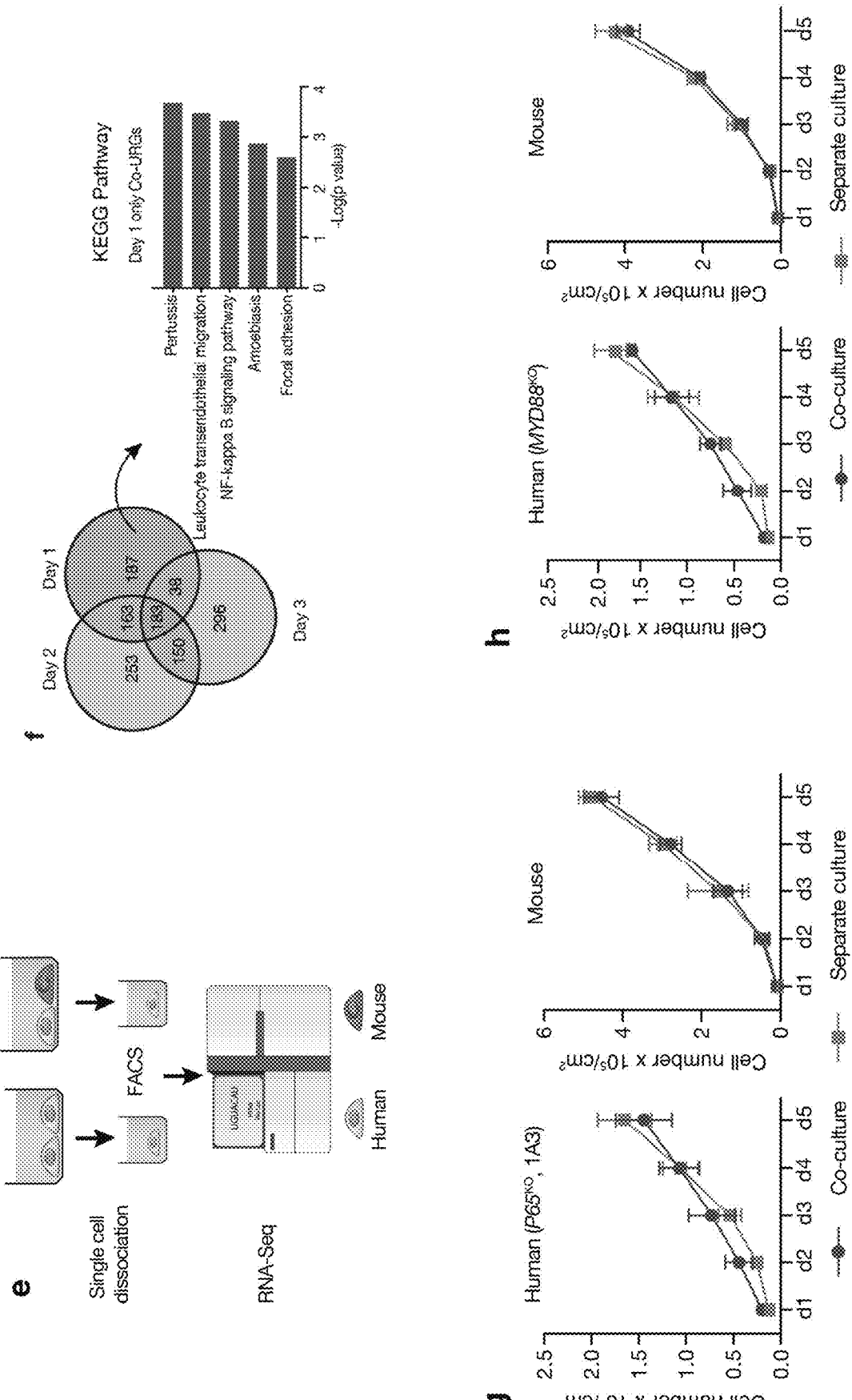

Next, we studied the effects of plating ratios and densities on human-mouse primed PSC competition. Although H9 hESCs were out-competed by mEpiSCs in all tested conditions, death responses varied. A more rapid elimination of human cells was observed when a higher proportion of mEpiSCs were seeded, suggesting cell-cell contact is important (FIG. 8a-c). We also co-cultured H9 hESCs and mEpiSCs on micropatterned coversildes (see Methods) to maximize cell-cell contact, and observed most human cell death occurred between days 2 and 3. To determine whether human-mouse primed PSC competition is contact dependent, we co-cultured H9 hESCs and mEpiSCs using transwell inserts to prevent direct cell-cell contact. Unlike normal "contact" co-culture, we found no evidence of cell competition between transwell co-cultured H9 hESCs and mEpiSCs (FIG. 2a, FIG. 8d and FIG. 11). In addition, we adopted an additional contactless co-culture strategy using ibidi chamber slides, which confirmed lack of cell competition when H9 hESCs and mEpiSCs were spatially kept apart. To examine whether secreted factors are involved, conditioned media (CM) were collected from mEpiSCs and H9 hESCs co-culture and separate-cultures. Different dosages of day 1-5 pooled unconcentrated (50%, 33%, and 10%) or concentrated CMs were used to treat H9 hESCs. In each condition tested, we did not observe pronounced human cell apoptosis (FIG. 2b and FIG. 8e). These results indicate that competition between human and mouse primed PSCs is contact-dependent and likely not through secreted factors.

EXAMPLE 6. This example describes signaling pathways in PSC competition.

While not being limited by theory, the competitive interaction between human and mouse primed PSCs during co-culture is dynamic and involves a multitude of different molecular and cellular processes at different timepoints. To shed light on signaling pathways involved, we performed RNA-sequencing (RNA-seq) using H9 hESCs isolated from separate- and co-cultures from days 1-3 (FIG. 2e). Comparative transcriptome analysis identified 571, 749, and 667 upregulated genes on day 1, 2, and 3, respectively, in co-cultured versus separately cultured H9 ESCs (Co-culture upregulated genes, or Co-URGs) (P<0.01, FPKM>1, and fold change>2) (FIG. 2f). Gene Ontology (GO) and KEGG pathway analyses were performed using Co-URGs from all (days 1, 2, and 3 combined), common (commonly shared among days 1, 2, and 3) and day 1 only. We found many enriched GO-cellular component terms related to the extracellular regions and the plasma membrane, consistent with the finding that human-mouse primed PSC competition is contact-dependent. Enriched GO-biological process terms included "positive regulation of apoptotic process", "inflammatory response", and "regulation of cell motility/migration", among others. KEGG pathway analysis confirmed that the P53 signaling pathway was among the overrepresented pathways in "all" (ranked $21^{st}$) and "common" (ranked $2^{nd}$) Co-URGs, which is consistent with our findings using TP53$^{KD}$- and TP53$^{KO}$-hiPSCs (FIG. 10a,b).

Interestingly, when we performed KEGG pathway analysis using day 1 only Co-URGs (187 genes), the TLR/NF-κB signaling pathway was found to be the top signaling pathway ($3^{rd}$ overall) (FIG. 2f). The TLR/NF-κB pathway was also enriched in all Co-URGs (ranked 9th) and many TLR/NF-κB pathway-related genes were significantly upregulated in co-cultured vs. separately cultured H9 hESCs (FIG. 10a, c-e). TLR/NF-κB represents an early response factor, which can be activated rapidly after stimulation, without the need for de novo protein synthesis. Therefore, we speculated that activation of TLR/NF-κB was among the first signaling cascades to trigger loser cell apoptosis during primed PSC co-culture. Of note, the TLR/NF-κB signaling pathway was recently found to play key roles in Myc-induced and Minute-induced cell competition in *Drosophila* wing discs. To determine if inhibition of TLR/NF-κB signaling could overcome human-mouse primed PSC competition, we disrupted P65 (a key component of the canonical TLR/NF-κB pathway) in HFF-iPSCs using CRISPR and generated several homozygous clones (P65$^{KO}$-hiPSCs) (FIG. 11a,b). P65$^{KO}$-hiPSCs displayed typical undifferentiated colony morphology characteristic of human primed PSCs, expressed core (OCT4 and SOX2) and primed (CD24) pluripotency markers, and maintained a normal diploid karyotype (FIG. 11c,d). In addition, P65$^{KO}$-hiPSCs could generate teratomas comprised of tissues from all three germ lineages when injected into NOD-SCID mice (FIG. 11e). These results demonstrate P65 deficiency did not compromise the self-renewal and pluripotency of HFF-iPSCs.

Next, we labeled P65$^{KO}$-hiPSCs with EGFP and subjected them to co-culture with mKO-mEpiSCs. In contrast to the WT control time-lapse confocal microscopy did not reveal obvious competition between mEpiSCs and P65$^{KO}$-hiPSCs. The total number of P65$^{KO}$-hiPSCs in separate- and co-cultures was comparable throughout the entire culture period (FIG. 2g and FIG. 11f). We obtained the same result using another P65$^{KO}$-hiPSCs clone (1B1) (FIG. 11g,h). Together, our results suggest activation of TLR/NF-κB signaling drives the elimination of loser cells during human-mouse primed PSC competition.

MyD88 is a key signaling adaptor for all mammalian Toll-like receptors (TLRs) (with the exception of TLR3), which has the main role of activating TLR/NF-κB. Next, we generated homozygous MYD88 knockout HFF-iPSCs (MYD88$^{KO}$-hiPSCs), and confirmed MYD88 deficiency did not perturb the self-renewal and primed pluripotency status of HFF-iPSCs (FIG. 11i-l). Similar to P65, MYD88 deficiency rescued HFF-hiPSCs from being out-competed by mEpiSCs (FIG. 2h, FIG. 11m). Next we studied the possible relationship between MYD88, P65 and P53 by examining P53 and TLR/NF-κB pathway activation status in co-cultured versus separately cultured WT-, MyD88$^{KO}$-, P53$^{KO}$- and P65$^{KO}$-hiPSCs. Our results suggest a MyD88-P53-P65 axis in triggering human cell death during human-mouse primed PSC competition (FIG. 11 n,o).

EXAMPLE 7. This example describes improving survival of human PSCs in early mouse embryos.

Figure 3:
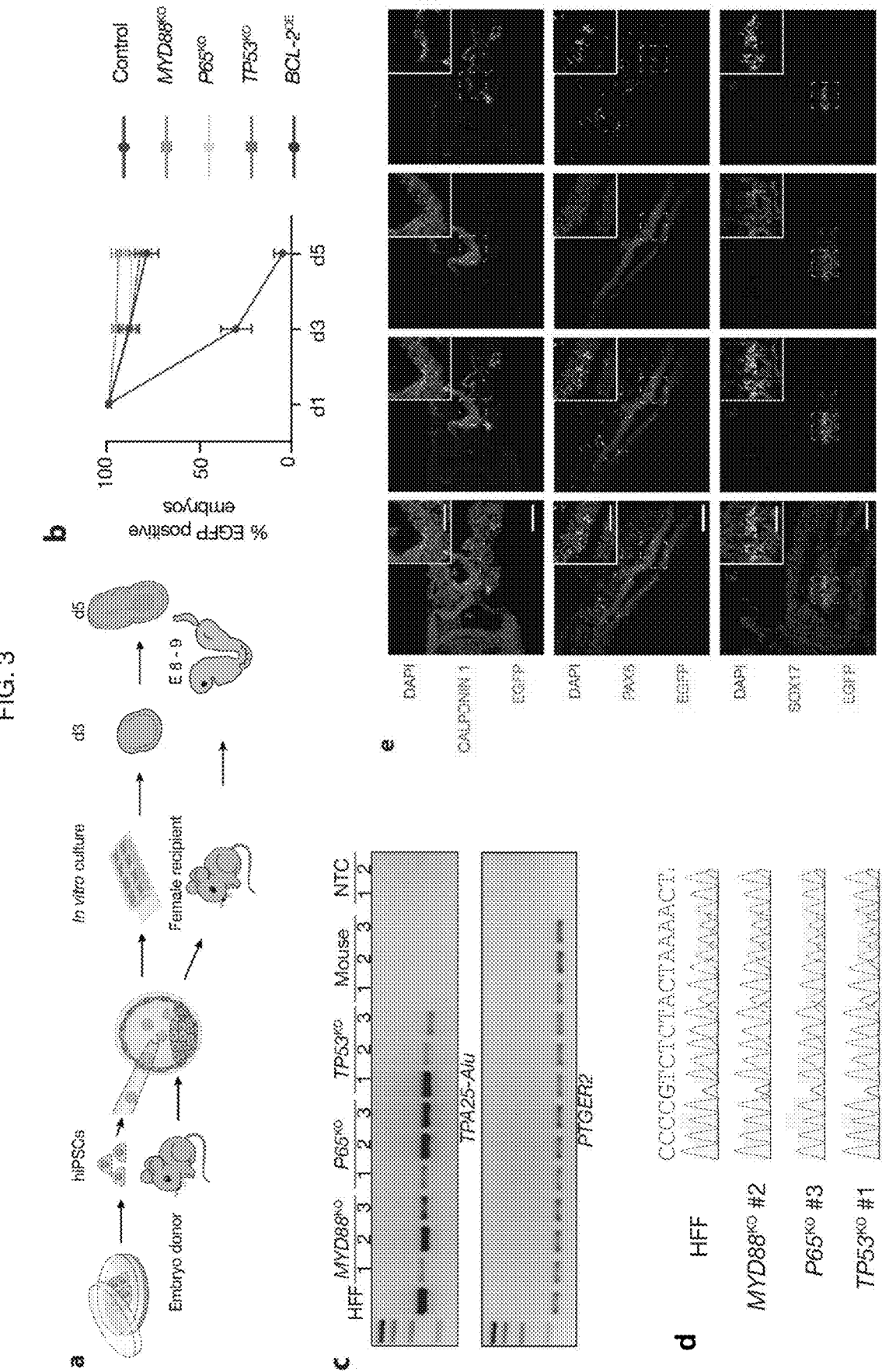
FIG. 3 panels a-e show that overcoming interspecies PSC competition enhances primed human PSCs survival and chimerism in early mouse embryos. a, Schematic of the experimental setup for the generation of ex vivo and in vivo human-mouse chimeric embryos. b, Line graphs showing the percentages of EGFP+ mouse embryos at indicated time points during in vitro embryo culture after blastocyst injection of WT-, MYD88$^{KO}$-, P65$^{KO}$-, TP-53$^{KO}$- and BCL-2$^{OE}$-hiPSCs. n=6, independent injection experiments, mean±s.e.m. ***P<0.001, compared with MYD88$^{KO}$-, P65$^{KO}$-, TP53$^{KO}$- and BCL-2$^{OE}$-hiPSCs. c, Genomic PCR analysis of selected E8-9 mouse embryos derived from blastocyst injection of MYD88$^{KO}$-, P65$^{KO}$- and TP53$^{KO}$-hiPSCs using a human specific Alu primer (TPA25-Alu). PTGER2 primer was used for loading control. E8-9 mouse embryos without injection of HFF-iPSCs were used as negative controls. HFF (HFF-iPSCs) was used as a positive control. NTC, non-template control. d, Sanger sequencing results of representative PCR products generated by human-specific TPA25-Alu primers. A stretch of TPA25-Alu DNA sequences derived from HFF, MYD88 KO (#2), P65 KO (#3) and TP53 KO (#1) from FIG. 3c were shown. CCCCGTCTCTACTAAAACTA is SEQ ID NO:44. e, Representative immunofluorescence images showing contribution and differentiation of MYD88KO-hiPSCs in E8-9 mouse embryos. Embryo sections were stained with antibodies against EGFP and lineage markers including CALPONIN 1 (mesoderm, top), PAX6 (ectoderm, middle) and SOX17 (endoderm, bottom). Scale bars, 100 μm and 50 μm (insets).

To determine whether overcoming interspecies primed PSC competition can help improve the survival of primed human PSCs in early mouse embryos, we performed micro-injections of EGFP labeled BCL-2$^{OE}$-, TP53$^{KO}$-, P65$^{KO}$-, MYD88$^{KO}$-, and WT-hiPSCs cultured in mTeSR1 medium into mouse blastocysts. We adopted an embryo culture system (IVC1 and IVC2 media) that enables the development of mouse blastocysts to post-implantation stages in vitro (FIG. 3a). After 3 days of culturing, EGFP signals could only be detected in 9 out of 36 embryos injected with WT-hiPSCs, while most embryos injected with BCL-2$^{OE}$-(18 out of 20), TP53$^{KO}$-(35 out of 41), P65$^{KO}$-(28 out of 31), and MYD88$^{KO}$-hiPSCs (62 out of 65) still contained EGFP$^+$ cells (FIG. 3b, FIG. 12a and Table 4. On day 5, only 9.52% (2 out of 21) embryos contained WT-hiPSCs. In sharp contrast, 80% (16 out of 20), 76.32% (29 out of 38), 85.19% (23 out of 27), and 95.12% (39 out of 41) embryos still contained BCL-2$^{OE}$-, TP53$^{KO}$-, P65$^{KO}$-, and MYD88$^{KO}$-hiPSCs, respectively (FIG. 3b, FIG. 12a and Table 4). Next, we stained day 5 embryos with antibodies against AC3 and OCT4. Our results confirmed the EGFP signal was from live human cells, and some EGFP$^+$/OCT4$^+$ cells were found inside mouse epiblast (FIG. 12b). These results demonstrate genetic perturbations of TP53, MYD88, and P65, as well as BCL-2 overexpression improve the survival of human primed PSCs in early mouse embryos ex vivo. Next, we performed embryo transfers and investigated whether primed TP53$^{KO}$-, P65$^{KO}$-, and MYD88$^{KO}$-hiPSCs could contribute to chimera formation in vivo. We could detect EGFP signal from a number of E8-9 embryos generated by MYD88$^{KO}$-, P65$^{KO}$-, and TP53$^{KO}$-, but not WT-hiPSCs (FIG. 12c and Table 4). Presence of human cells was independently confirmed by immunofluorescence analysis of embryo sections, genomic PCR using human-specific Alu (TPA25-Alu) primers, and Sanger sequencing (FIG. 3c,d and FIG. 12c-e). Based on fluorescent and immunofluorescent EGFP signal, we determined the percentages of E8-9 mouse embryos containing human cells were 19.39% (19 out of 98), 9.52% (4 out of 42), 8% (4 out of 50) for MYD88$^{KO}$-, P65$^{KO}$-, and TP53$^{KO}$-hiPSCs, respectively, which were in contrast to 0% (0 out of 23) for WT-hiPSCs (FIG. 12c and Table 4). We next performed co-staining of EGFP with different lineage markers: endoderm (SOX17), mesoderm (CALPONIN-1), and ectoderm (PAX6), and found MYD88$^{KO}$-, P65$^{KO}$- and TP53$^{KO}$-hiPSCs differentiated into cells from all three primary germ layers (FIG. 3d and FIG. 12e, f). Taken together, genetic inactivation of either TP53, MYD88, or P65 confers primed HFF-iPSCs with the ability to contribute to chimera formation in early mouse embryos in vivo.

FIG. 13 k,l). Interestingly, bESCs were out-competed by both rodent and primate PSCs. To determine whether MYD88$^{KO}$, TP53$^{KO}$, P65$^{KO}$, or BCL2$^{OE}$ conferred HFF-hiPSCs with the "super competitor" status, we co-cultured them with WT-hiPSCs or -rhESCs and found no obvious cell competition in all tested conditions (FIG. 14). In agreement, Myd88 deficiency did not further improve chimeric contribution of rat ESCs to mouse embryos (FIG. 14i,k). Tp53$^{KO}$-rat ESCs, on the other hand, showed increased chimerism in E10.5 mouse embryos when compared with WT rat ESCs (FIG. 14j,k), albeit at a much lower level than Tp53$^{KD}$-miPSCs reported previously. Collectively, these results extend primed PSC competition beyond human-mouse and suggest it is a more general phenomenon among different species.

EXAMPLE 9. Discussion of Examples 1-8. Studies described in Examples 1-7 uncovered a previously unrecognized mode of cell competition between PSCs of evolutionarily distant species. This interspecies PSC competition occurs within primed pluripotency, representing the time at which the in vivo epiblast begins to undergo gastrulation and

TABLE 4

Human-mouse Chimera Studies

| | | Day 3 | | | | Day 5 | | | | |
|---|---|---|---|---|---|---|---|---|---|---|
| | | Normal appearance | | Retarded | | | Normal appearance | | Retarded | |
| | No. Bl injected | No. Em attached | EGFP+ | EGFP− | EGFP+ | EGFP− | No. Em alive | EGFP+ | EGFP− | EGFP+ | EGFP− |
| WT | 52 | 49 | 9 | 27 | 1 | 12 | 37 | 2 | 19 | 0 | 16 |
| BCL2$^{OE}$ | 45 | 39 | 18 | 2 | 13 | 6 | 38 | 16 | 4 | 10 | 8 |
| TP53$^{KO}$ | 94 | 74 | 35 | 6 | 16 | 17 | 71 | 29 | 9 | 12 | 21 |
| P65$^{KO}$ | 80 | 65 | 28 | 3 | 17 | 17 | 63 | 23 | 4 | 15 | 21 |
| MYD88$^{KO}$ | 95 | 87 | 62 | 3 | 15 | 7 | 82 | 39 | 2 | 29 | 12 |

*Note:
Bl, blastocyst;
Em, embryo

EXAMPLE 8. To examine whether primed PSC competition also occurs between other species, we studied bovine ESCs (bESCs), rhesus macaque ESCs (rhESCs, ORMES23), and rat EpiSCs (rEpiSCs) grown in the FR condition, in addition to human and mouse cells (FIG. 13a,b). FR-cultured bESCs, rhESCs, and rEpiSCs stably maintained expression of pluripotency markers in long term cultures (FIG. 13c). We mixed and matched PSCs from different species in co-culture experiments. Similar to human-mouse, pronounced cell competition was observed in all co-culture combinations between a primate (human or rhesus) and a rodent (mouse or rat) (FIG. 4a,b, FIG. 13 d-f), probably due to differential primed PSC fitness. Less-fit human or rhesus cells were mostly eliminated by fitter mouse or rat cells after 5 days' co-culture. Consistent with the results using mEpiSCs, MYD88 and P65 deficiency also prevented HFF-hiPSCs from being out-competed by rEpiSCs (FIG. 13 g, h). In contrast, little to no cell competition was observed in rat-mouse and human-rhesus primed PSC co-cultures (FIG. 4c, FIG. 13i, j), suggesting comparable cell fitness between these cells. We also observed noticeable cell competition in mouse-cow, rat-cow, human-cow, and rhesus-cow primed PSC co-cultures (FIG. 4 d,e, is accompanied by a wave of cell death. Interspecies primed PSC competition was shown to be contact-dependent, and TLR/NF-κB activation putatively downstream of MyD88 was shown to drive loser cell elimination. Recently, apoptosis was recognized as an initial barrier of interspecies chimerism, and forced expression of anti-apoptotic factors including BCL-2 and BMI1 improved human PSC chimerism in early post-implantation mouse embryos. Without being limited by theory, results of studies described above provide mechanistic insights and discover that human cell death during interspecies chimera formation is due to cell competition during primed pluripotency. In addition, the MyD88/NF-κB pathway, when inactivated in human PSCs, can overcome interspecies PSC competition in culture and improve human cell survival and engraftment in early mouse embryos. Without being limited by theory, the studies described above establish a novel platform to study evolutionarily conserved cell competition mechanisms during early mammalian development, and when combined with other strategies, can overcome the xenogeneic barrier and lead to successful interspecies organogenesis in an evolutionarily distant host.

What is claimed is:

1. A chimeric blastocyst, comprising:

(i) a host blastocyst from a first mammalian species, wherein the host blastocyst is an organogenesis disabled blastocyst comprising a genetic deficiency and wherein the first mammalian species is a rodent; and (ii) donor pluripotent stem cells from a second mammalian species, wherein the donor pluripotent stem cells have a homozygous disruption of one or more of p65 and MYD88, wherein said homozygous disruption leads to reduced expression or reduced biological activity of one or more of p65 and MYD88, and wherein the second mammalian species is a human.

2. The chimeric blastocyst of claim 1, wherein the donor pluripotent stem cells comprise induced pluripotent stem cells.

3. A method of preparing a chimeric blastocyst comprising:

injecting a host blastocyst from a first mammalian species, wherein the first mammalian species is a rodent, with donor pluripotent stem cells from a second mammalian species, wherein the second mammalian species is a human, wherein the host blastocyst is an organogenesis disabled blastocyst comprising a genetic deficiency, wherein the donor pluripotent stem cells have a homozygous disruption of one or more of p65 and MYD88, wherein said homozygous disruption leads to reduced expression or reduced biological activity of one or more of p65 and MYD88.

4. The method of claim 3, wherein the donor pluripotent stem cells comprise primed pluripotent stem cells.

\* \* \* \* \*

SEQUENCE LISTING

<160> NUMBER OF SEQ ID NOS: 53

<210> SEQ ID NO 1
<211> LENGTH: 23
<212> TYPE: DNA
<213> ORGANISM: Artificial Sequence
<220> FEATURE:
<223> OTHER INFORMATION: hP65 gRNA

<400> SEQUENCE: 1
attgagcagc ccaagcagcg ggg                                                          23

<210> SEQ ID NO 2
<211> LENGTH: 23
<212> TYPE: DNA
<213> ORGANISM: Artificial Sequence
<220> FEATURE:
<223> OTHER INFORMATION: hMYd88 gRNA

<400> SEQUENCE: 2
cttgaacgtg cggacacagg tgg                                                          23

<210> SEQ ID NO 3
<211> LENGTH: 23
<212> TYPE: DNA
<213> ORGANISM: Artificial Sequence
<220> FEATURE:
<223> OTHER INFORMATION: hTP53 gRNA

<400> SEQUENCE: 3
accagcagct cctacaccgg cgg                                                          23

<210> SEQ ID NO 4
<211> LENGTH: 23
<212> TYPE: DNA
<213> ORGANISM: Artificial Sequence
<220> FEATURE:
<223> OTHER INFORMATION: hTSC1 gRNA

<400> SEQUENCE: 4
cgagaggatg gataaacgag tgg                                                          23

<210> SEQ ID NO 5
<211> LENGTH: 23
<212> TYPE: DNA
<213> ORGANISM: Artificial Sequence
<220> FEATURE:
<223> OTHER INFORMATION: rP65 gRNA

<400> SEQUENCE: 5
attgagcagc ccaagcagcg ggg                                                          23

<210> SEQ ID NO 6
<211> LENGTH: 23
<212> TYPE: DNA
<213> ORGANISM: Artificial Sequence
<220> FEATURE:
<223> OTHER INFORMATION: rMYD88 gRNA

<400> SEQUENCE: 6
gagcagtgtc ccacagacaa agg                                                          23

<210> SEQ ID NO 7
<211> LENGTH: 23
<212> TYPE: DNA
<213> ORGANISM: Artificial Sequence
<220> FEATURE:
<223> OTHER INFORMATION: rTP53 gRNA

<400> SEQUENCE: 7
gacagggtca cctaattcca tgg                                               23

<210> SEQ ID NO 8
<211> LENGTH: 20
<212> TYPE: DNA
<213> ORGANISM: Artificial Sequence
<220> FEATURE:
<223> OTHER INFORMATION: hP65 F sequencing primer

<400> SEQUENCE: 8
gtgtgctgac cctgatctcc                                                   20

<210> SEQ ID NO 9
<211> LENGTH: 20
<212> TYPE: DNA
<213> ORGANISM: Artificial Sequence
<220> FEATURE:
<223> OTHER INFORMATION: hP65 R sequencing primer

<400> SEQUENCE: 9
tacttcatag cccgcctcct                                                   20

<210> SEQ ID NO 10
<211> LENGTH: 20
<212> TYPE: DNA
<213> ORGANISM: Artificial Sequence
<220> FEATURE:
<223> OTHER INFORMATION: hMYD88  F sequencing primer

<400> SEQUENCE: 10
gctccagatt gtagggcagg                                                   20

<210> SEQ ID NO 11
<211> LENGTH: 20
<212> TYPE: DNA
<213> ORGANISM: Artificial Sequence
<220> FEATURE:
<223> OTHER INFORMATION: hMYD88 R sequencing primer

<400> SEQUENCE: 11
gaaagtcagc ctcctcaccc                                                   20

<210> SEQ ID NO 12
<211> LENGTH: 20
<212> TYPE: DNA
<213> ORGANISM: Artificial Sequence
<220> FEATURE:
<223> OTHER INFORMATION: hTP53 F sequencing primer

<400> SEQUENCE: 12
gagacctgtg ggaagcgaaa                                                   20

<210> SEQ ID NO 13
<211> LENGTH: 20
<212> TYPE: DNA
<213> ORGANISM: Artificial Sequence
<220> FEATURE:
<223> OTHER INFORMATION: hTP53 R sequencing primer

<400> SEQUENCE: 13
gctgccctgg taggttttct                                                   20

-continued

```
<210> SEQ ID NO 14
<211> LENGTH: 20
<212> TYPE: DNA
<213> ORGANISM: Artificial Sequence
<220> FEATURE:
<223> OTHER INFORMATION: hTSC1 F sequencing primer

<400> SEQUENCE: 14
catgagctgc aaactggctg                                                   20

<210> SEQ ID NO 15
<211> LENGTH: 22
<212> TYPE: DNA
<213> ORGANISM: Artificial Sequence
<220> FEATURE:
<223> OTHER INFORMATION: hTSC1 R sequencing primer

<400> SEQUENCE: 15
tgagggaagg ctaaacgatg ac                                                22

<210> SEQ ID NO 16
<211> LENGTH: 20
<212> TYPE: DNA
<213> ORGANISM: Artificial Sequence
<220> FEATURE:
<223> OTHER INFORMATION: rP65 F sequencing primer

<400> SEQUENCE: 16
agtaggtagg ggctgtcctg                                                   20

<210> SEQ ID NO 17
<211> LENGTH: 20
<212> TYPE: DNA
<213> ORGANISM: Artificial Sequence
<220> FEATURE:
<223> OTHER INFORMATION: rP65 R sequencing primer

<400> SEQUENCE: 17
ggacagagca aggactctgg                                                   20

<210> SEQ ID NO 18
<211> LENGTH: 20
<212> TYPE: DNA
<213> ORGANISM: Artificial Sequence
<220> FEATURE:
<223> OTHER INFORMATION: rMYD88 F sequencing primer

<400> SEQUENCE: 18
agggagaggg ttagtccgtc                                                   20

<210> SEQ ID NO 19
<211> LENGTH: 20
<212> TYPE: DNA
<213> ORGANISM: Artificial Sequence
<220> FEATURE:
<223> OTHER INFORMATION: rMYD88 R sequencing primer

<400> SEQUENCE: 19
cttgcccaaa gtccccagat                                                   20

<210> SEQ ID NO 20
<211> LENGTH: 20
<212> TYPE: DNA
<213> ORGANISM: Artificial Sequence
<220> FEATURE:
<223> OTHER INFORMATION: rTP53 F sequencing primer
```

<400> SEQUENCE: 20
gctagcctgg ggtaagtgag                                              20

<210> SEQ ID NO 21
<211> LENGTH: 20
<212> TYPE: DNA
<213> ORGANISM: Artificial Sequence
<220> FEATURE:
<223> OTHER INFORMATION: rTP53 R sequencing primer

<400> SEQUENCE: 21
aaagcaactc ttcaggccca                                              20

<210> SEQ ID NO 22
<211> LENGTH: 20
<212> TYPE: DNA
<213> ORGANISM: Artificial Sequence
<220> FEATURE:
<223> OTHER INFORMATION: hTp53 F qPRC Primer

<400> SEQUENCE: 22
gcgagcactg cccaacaaca                                              20

<210> SEQ ID NO 23
<211> LENGTH: 23
<212> TYPE: DNA
<213> ORGANISM: Artificial Sequence
<220> FEATURE:
<223> OTHER INFORMATION: hTp53 R qPRC Primer

<400> SEQUENCE: 23
ggatctgaag ggtgaaatat tct                                          23

<210> SEQ ID NO 24
<211> LENGTH: 19
<212> TYPE: DNA
<213> ORGANISM: Artificial Sequence
<220> FEATURE:
<223> OTHER INFORMATION: TFCP2L1 F qPRC Primer

<400> SEQUENCE: 24
gctcttcaac gccatcaaa                                               19

<210> SEQ ID NO 25
<211> LENGTH: 18
<212> TYPE: DNA
<213> ORGANISM: Artificial Sequence
<220> FEATURE:
<223> OTHER INFORMATION: TFCP2L1 R qPRC Primer

<400> SEQUENCE: 25
caggggcact cgattctg                                                18

<210> SEQ ID NO 26
<211> LENGTH: 20
<212> TYPE: DNA
<213> ORGANISM: Artificial Sequence
<220> FEATURE:
<223> OTHER INFORMATION: STELLA F qPRC Primer

<400> SEQUENCE: 26
gttactgggc ggagttcgta                                              20

<210> SEQ ID NO 27

```
<211> LENGTH: 20
<212> TYPE: DNA
<213> ORGANISM: Artificial Sequence
<220> FEATURE:
<223> OTHER INFORMATION: STELLA R qPRC Primer

<400> SEQUENCE: 27
tgaagtggct tggtgtcttg                                              20

<210> SEQ ID NO 28
<211> LENGTH: 19
<212> TYPE: DNA
<213> ORGANISM: Artificial Sequence
<220> FEATURE:
<223> OTHER INFORMATION: TBX3 F qPRC Primer

<400> SEQUENCE: 28
gcagctttca actgcttcg                                               19

<210> SEQ ID NO 29
<211> LENGTH: 20
<212> TYPE: DNA
<213> ORGANISM: Artificial Sequence
<220> FEATURE:
<223> OTHER INFORMATION: TBX3 R qPRC Primer

<400> SEQUENCE: 29
accctcgctg ggacataaat                                              20

<210> SEQ ID NO 30
<211> LENGTH: 19
<212> TYPE: DNA
<213> ORGANISM: Artificial Sequence
<220> FEATURE:
<223> OTHER INFORMATION: KLF4 F qPRC Primer

<400> SEQUENCE: 30
gggagaagac actgcgtca                                               19

<210> SEQ ID NO 31
<211> LENGTH: 18
<212> TYPE: DNA
<213> ORGANISM: Artificial Sequence
<220> FEATURE:
<223> OTHER INFORMATION: KLF4 R qPRC Primer

<400> SEQUENCE: 31
ggaagcactg ggggaagt                                                18

<210> SEQ ID NO 32
<211> LENGTH: 20
<212> TYPE: DNA
<213> ORGANISM: Artificial Sequence
<220> FEATURE:
<223> OTHER INFORMATION: KLF17 F qPRC Primer

<400> SEQUENCE: 32
ctcctgctgc tggtccttag                                              20

<210> SEQ ID NO 33
<211> LENGTH: 19
<212> TYPE: DNA
<213> ORGANISM: Artificial Sequence
<220> FEATURE:
<223> OTHER INFORMATION: KLF17 R qPRC Primer

<400> SEQUENCE: 33
```

-continued

```
acagttgcca cgtccagtg                                            19

<210> SEQ ID NO 34
<211> LENGTH: 25
<212> TYPE: DNA
<213> ORGANISM: Artificial Sequence
<220> FEATURE:
<223> OTHER INFORMATION: DPPA3 F qPRC Primer

<400> SEQUENCE: 34
aatgctagaa tagggaatca agaca                                     25

<210> SEQ ID NO 35
<211> LENGTH: 25
<212> TYPE: DNA
<213> ORGANISM: Artificial Sequence
<220> FEATURE:
<223> OTHER INFORMATION: DPPA3 R qPRC Primer

<400> SEQUENCE: 35
agcatagagt agctttctca acctg                                     25

<210> SEQ ID NO 36
<211> LENGTH: 25
<212> TYPE: DNA
<213> ORGANISM: Artificial Sequence
<220> FEATURE:
<223> OTHER INFORMATION: TPA-25 Alu F genomic PCR

<400> SEQUENCE: 36
gtaagagttc cgtaacagga cagct                                     25

<210> SEQ ID NO 37
<211> LENGTH: 25
<212> TYPE: DNA
<213> ORGANISM: Artificial Sequence
<220> FEATURE:
<223> OTHER INFORMATION: TPA-25 Alu R Genomic PCR

<400> SEQUENCE: 37
ccccacccta ggagaacttc tcttt                                     25

<210> SEQ ID NO 38
<211> LENGTH: 20
<212> TYPE: DNA
<213> ORGANISM: Artificial Sequence
<220> FEATURE:
<223> OTHER INFORMATION: PTGER2 F Genomic PCR

<400> SEQUENCE: 38
tacctgcagc tgtacgccac                                           20

<210> SEQ ID NO 39
<211> LENGTH: 20
<212> TYPE: DNA
<213> ORGANISM: Artificial Sequence
<220> FEATURE:
<223> OTHER INFORMATION: PTGER2 R Genomic PCR

<400> SEQUENCE: 39
gccaggagaa tgaggtggtc                                           20

<210> SEQ ID NO 40
<211> LENGTH: 38
<212> TYPE: DNA
```

-continued

```
<213> ORGANISM: Artificial Sequence
<220> FEATURE:
<223> OTHER INFORMATION: Rat specific mtDNA primer F Genomic PCR

<400> SEQUENCE: 40
gacctccccg ccccatctaa catctcatca tgatgaaa                            38

<210> SEQ ID NO 41
<211> LENGTH: 28
<212> TYPE: DNA
<213> ORGANISM: Artificial Sequence
<220> FEATURE:
<223> OTHER INFORMATION: Rat specific mtDNA primer R Genomic PCR

<400> SEQUENCE: 41
gaatgggatt ttgtctgcgt cggagttt                                       28

<210> SEQ ID NO 42
<211> LENGTH: 21
<212> TYPE: DNA
<213> ORGANISM: Artificial Sequence
<220> FEATURE:
<223> OTHER INFORMATION: Rat-mouse conserved mtDNA primer F Genomic PCR

<400> SEQUENCE: 42
gctaagaccc aaactgggat t                                              21

<210> SEQ ID NO 43
<211> LENGTH: 21
<212> TYPE: DNA
<213> ORGANISM: Artificial Sequence
<220> FEATURE:
<223> OTHER INFORMATION: Rat-mouse conserved mtDNA primer R Genomic PCR

<400> SEQUENCE: 43
ggtttgctga agatggcggt a                                              21

<210> SEQ ID NO 44
<211> LENGTH: 20
<212> TYPE: DNA
<213> ORGANISM: Artificial Sequence
<220> FEATURE:
<223> OTHER INFORMATION: Primer for TPA25-Alu

<400> SEQUENCE: 44
ccccgtctct actaaaacta                                                20

<210> SEQ ID NO 45
<211> LENGTH: 23
<212> TYPE: DNA
<213> ORGANISM: Artificial Sequence
<220> FEATURE:
<223> OTHER INFORMATION: 65 bp deletion mutation in TP53 KO hiPSCs

<400> SEQUENCE: 45
accagcagct cctacaccgg cgg                                            23

<210> SEQ ID NO 46
<211> LENGTH: 23
<212> TYPE: DNA
<213> ORGANISM: Homo sapiens

<400> SEQUENCE: 46
attgagcagc ccaagcagcg ggg                                            23
```

-continued

```
<210> SEQ ID NO 47
<211> LENGTH: 24
<212> TYPE: DNA
<213> ORGANISM: Artificial Sequence
<220> FEATURE:
<223> OTHER INFORMATION: 1BB insertion mutations

<400> SEQUENCE: 47
attgagcagc ccaagcaagc gggg                                           24

<210> SEQ ID NO 48
<211> LENGTH: 37
<212> TYPE: DNA
<213> ORGANISM: Homo sapiens

<400> SEQUENCE: 48
ctctgttctt gaacgtgcgg acacaggtgg cggccga                             37

<210> SEQ ID NO 49
<211> LENGTH: 24
<212> TYPE: DNA
<213> ORGANISM: Artificial Sequence
<220> FEATURE:
<223> OTHER INFORMATION: 13 bp deletion mutation in human MYD88 gene

<400> SEQUENCE: 49
ctctgttctt gaacgtgcgg acga                                           24

<210> SEQ ID NO 50
<211> LENGTH: 37
<212> TYPE: DNA
<213> ORGANISM: Rat

<400> SEQUENCE: 50
gagtggagag cagtgtccca cagacaaagg aactggg                             37

<210> SEQ ID NO 51
<211> LENGTH: 15
<212> TYPE: DNA
<213> ORGANISM: Artificial Sequence
<220> FEATURE:
<223> OTHER INFORMATION: 22bp deletion mutation in MYD88 KO rat ESCs

<400> SEQUENCE: 51
gagtggagaa ctggg                                                     15

<210> SEQ ID NO 52
<211> LENGTH: 37
<212> TYPE: DNA
<213> ORGANISM: Rat

<400> SEQUENCE: 52
ccacagcgac agggtcacct aattccatgg aagatct                             37

<210> SEQ ID NO 53
<211> LENGTH: 36
<212> TYPE: DNA
<213> ORGANISM: Artificial Sequence
<220> FEATURE:
<223> OTHER INFORMATION: 1bp deletion mutation in Tp53 KO rat ESCs.

<400> SEQUENCE: 53
ccacagcgac agggtcacct aatccatgga agatct                              36
```